US008734780B2

(12) United States Patent
Sharma et al.

(10) Patent No.: US 8,734,780 B2
(45) Date of Patent: May 27, 2014

(54) METHODS FOR TREATING CARDIAC PACING CONDITIONS

(75) Inventors: Vinod Sharma, Maple Grove, MN (US); Xiaohong Qiu, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 151 days.

(21) Appl. No.: 13/096,135

(22) Filed: Apr. 28, 2011

(65) Prior Publication Data
US 2011/0300107 A1 Dec. 8, 2011

Related U.S. Application Data

(60) Provisional application No. 61/351,836, filed on Jun. 4, 2010.

(51) Int. Cl.
| A61K 31/7088 | (2006.01) |
| A61K 35/00 | (2006.01) |
| A61P 9/00 | (2006.01) |
| C12N 5/10 | (2006.01) |

(52) U.S. Cl.
USPC .................. 424/93.2; 514/44 R; 435/325

(58) Field of Classification Search
CPC ... A61K 38/00; A61K 48/0005; C07K 14/705
See application file for complete search history.

(56) References Cited

U.S. PATENT DOCUMENTS

| 4,703,004 | A | 10/1987 | Hopp et al. |
| 4,782,137 | A | 11/1988 | Hopp et al. |
| 5,594,115 | A | 1/1997 | Sharma |
| 5,935,824 | A | 8/1999 | Sgarlato |
| 6,214,620 | B1 | 4/2001 | Johns et al. |
| 6,376,471 | B1 | 4/2002 | Lawrence, III et al. |
| 6,506,379 | B1 | 1/2003 | Clackson et al. |
| 6,703,485 | B2 | 3/2004 | Kandel et al. |
| 7,103,418 | B2 | 9/2006 | Laske et al. |
| 7,187,971 | B2 | 3/2007 | Sommer et al. |
| 7,274,966 | B2 | 9/2007 | Sommer et al. |
| 7,740,623 | B2 | 6/2010 | Nayak et al. |
| 8,076,305 | B2 | 12/2011 | Sigg |
| 2002/0022259 | A1 | 2/2002 | Lee et al. |
| 2003/0204206 | A1 | 10/2003 | Padua et al. |
| 2004/0267326 | A1 | 12/2004 | Ocel et al. |
| 2006/0247697 | A1 | 11/2006 | Sharma et al. |
| 2007/0218034 | A1* | 9/2007 | Sigg et al. ............... 424/93.2 |
| 2008/0103537 | A1 | 5/2008 | Sigg et al. |
| 2009/0054943 | A1 | 2/2009 | Qu et al. |
| 2009/0093026 | A1 | 4/2009 | Dowdy et al. |
| 2009/0099611 | A1 | 4/2009 | Sigg et al. |
| 2009/0203071 | A1 | 8/2009 | Chen |
| 2009/0233990 | A1 | 9/2009 | Cho et al. |
| 2009/0233991 | A1 | 9/2009 | Cho et al. |
| 2010/0137976 | A1 | 6/2010 | Sullivan et al. |
| 2011/0144028 | A1 | 6/2011 | Sharma et al. |
| 2011/0300107 | A1 | 12/2011 | Sharma et al. |
| 2011/0301568 | A1* | 12/2011 | Sharma et al. ............. 604/503 |
| 2011/0319478 | A1* | 12/2011 | Sharma et al. ............. 514/44 R |

FOREIGN PATENT DOCUMENTS

| WO | 9208796 A1 | 5/1992 | |
| WO | 9428143 A1 | 12/1994 | |
| WO | 9802150 A1 | 1/1998 | |
| WO | 02087419 A2 | 11/2002 | |
| WO | 02098286 A2 | 12/2002 | |
| WO | WO 2004/093969 A1 | 11/2004 | |
| WO | 2005062890 A2 | 7/2005 | |
| WO | 2005062958 A2 | 7/2005 | |
| WO | WO 2005/062958 A3 | 5/2007 | |
| WO | 2008024998 A2 | 2/2008 | |
| WO | 2008055001 A1 | 5/2008 | |
| WO | WO2008/067279 | * 5/2008 | ............. A61K 48/00 |
| WO | 2008067279 A2 | 6/2008 | |
| WO | WO 2008/024998 A3 | 11/2008 | |

OTHER PUBLICATIONS

Ishii et al (Biochemical and Biophysical Research Communications 2007; 359(3): 592-698).*
McCarty et al. (Gene Therapy. 2001; 8:1248-1254).*
Alignment—human HCN4 v rabbit HCN4 (2013).*
U.S. Appl. No. 12/917,062, filed Nov. 1, 2010, Sharma et al.
U.S. Appl. No. 13/109,151, filed May 17, 2011, Sharma.
Baruscotti et al., "Physiology and pharmacology of the cardiac pacemaker ("funny") current" *Pharmacology & Therapeutics,* 2005; 107:59-79.
Bell et al. "Changes in local S4 environment provide a voltage-sensing mechanism for mammalian hyperpolarization-activated HCN channels" *J. Gen. Physiol.,* Jan. 2004; 123:5-19.
Bucchi et al., "Wild-type and mutant HCN channels in a tandem biological-electronic cardiac pacemaker" *Circulation,* Sep. 5, 2006; 114(10):992-9, published online Aug. 21, 2006.
Chen et al., "The S4-S5 linker couples voltage sensing and activation of pacemaker channels" *PNAS,* Sep. 25, 2001, 98(20):11277-11282.
DiFrancesco, "Pacemaker Mechanisms in Cardiac Tissue", *Annu. Rev. Physiol.,* 1993, 55:455-472.
Edelberg, et al., Enhancement of Murine Cardiac Chronotropy by the Molecular Transfer of the Human β2 Adrenergic Receptor cDNA, *J. Clin. Invest.,* 1998, 101:337-343.
Edelberg, et al., "Molecular Enhancement of Porcine Cardiac Chronotropy", *Heart,* 2001; 86:559-562.
Henrikson et al., "Identification of a surface charged residue in the S3-S4 linker of the pacemaker (HCN) channel that influences activation gating" *J. Biol. Chem.,* 2003;278(16):13647-13654.
Ishii et al., "Determinant of activation kinetics in mammalian hyperpolarization-activated cation channels" *Journal of Physiology,* 2001; 537(Pt.1):93-100.

(Continued)

*Primary Examiner* — Scott Long

(57) ABSTRACT

The method may include administering to a subject in need thereof an effective amount of an HCN polynucleotide. The HCN polynucleotide includes a nucleotide sequence encoding an HCN polypeptide having channel activity. The amino acid sequence of the HCN polypeptide and the amino acid sequence of a reference polypeptide have at least 80% identity, where the reference polypeptide begins with an amino acid selected from amino acids 92-214 and ends with an amino acid selected from amino acids 723-1188 of SEQ ID NO:8. An example of a reference polypeptide is amino acids 214-723 of SEQ ID NO:8. The HCN polynucleotide may be DNA or RNA.

20 Claims, 22 Drawing Sheets

(56) References Cited

OTHER PUBLICATIONS

Ishii et al., "Tryptophan-scanning mutagenesis in the S1 domain of mammalian HCN channel reveals residues critical for voltage-gated activation" *J. Physiol.*, 2007; 579(Pt.2):291-301.

Kashiwakura et al., "Gene transfer of a synthetic pacemaker channel into the heart: A novel strategy for biological pacing" *Circulation*, Oct. 17, 2006, 114(16):1682-1686, published online Oct. 9, 2006.

Ludwig et al., "A Family of Hyperpolarization-Activated Mammalian Cation Channels", *Nature*, 1998; 393:587-591.

Miake et al., "Biological Pacemaker Created by Gene Transfer", *Nature*, 2002; 419:132-133.

Moroni et al., "Kinetic and Ionic Properties of the Human HCN2 Pacemaker Channel", *Pflugers Archiv*; 2000; 439:618-626.

Plotnikov et al., "Biological Pacemaker Implanted in Canine Left Bundle Branch Provides Ventricular Escape Rhythms that Have Physiologically Acceptable Rates", *Circulation*, 2004; 109(4):506-512.

Potapova et al., "Human Mesenchymal Stem Cells as a Gene Delivery System to Create Cardiac Pacemakers", *Circulation Research*, 94:952-959 (Epub ahead of print Feb. 26, 2004).

Qu et al., Expression and function of a biological pacemaker in canine heart *Circulation*, Mar. 4, 2003; 107:1106-1109, published online Feb. 24, 2003.

Rosen et al., "Recreating the Biological Pacemaker", *The Anatomical Record Part A*, 2004, 280(2); 1046-1052.

Rychlik et al., "Optimization of the Annealing Temperature for DNA Amplification in vitro", *Nucleic Acids Research*, 1990; 18:6409-6412.

Skolnick et al., "From Genes to Protein Structure and Function: Novel Applications of Computational Approaches in the Genomic era", *Trends in Biotechnology*, 2000; 18:34-39.

Tsang et al., Dissecting the structural and functional roles of the S3-S4 linker of pacemaker (hyperpolarization-activated cyclic nucleotide-modulated) channels by systematic length alterations, *J. Biol. Chem.*, Oct. 15, 2004; 279(42):43752-43759.

Tse et al., Bioartificial Sinus Node Constructed via in vivo gene transfer of an engineered pacemaker HCN channel reduces the dependence on electronic pacemaker in a sick-sinus syndrome model, *Circulation*, Sep. 5, 2006; 114(10):1000-11, published online Aug. 21, 2006.

Xiao et al., "Biological approaches to generating cardiac biopacemaker for bradycardia" *Acta Physiologica Sinica*, Oct. 25, 2007, 59(5):562-570.

Biel et al., Hyperpolarization-Activated Cation Channels: A Multi-Gene Family, *Review of Physiology, Biochemistry and Pharmacology*, 1999, 165-181.

Ishii et al., Peripheral N- and C-Terminal Domains Determine Activation Kinetcis of HCN Channels, *Biochemical and Biphysical Research Communications*, 359 (2007) 592-598.

Marten et al., The N-Terminus of the K Channel KAT1 Controls its Voltage-Dependent Gating by Altering the Membrane Electric Field, *Biophysical Journal*, vol. 74, (1998), 2953-2962.

(PCT/US2011/038779) PCT Notification of Transmittal of the International Search Report and the Written Opinion of the International Searching Authority, Mailed Oct. 4, 2011, 10 pages.

Tatusova, et al., FEMS Microbiol. Lett., 1999, 174:247-250 and located on the World Wide Web at http://www.ncbi.nlm.nih.gov/pubmed/10339815 maintained by the National Center for Biotechnology Information, National Institutes of Health.

3 Abmayr, et al., Current Protocols in Molecular Biology (2006).

Much et al., "Role of Subunit Heteromerization and N-Linked Glycosylation in the Formation of Functional Hyperpolarization-activated Cyclic Nucleotide-gated Channels", vol. 278, No. 44, Issue of Oct. 31, 2003, pp. 43781-43786.

Vaca et al., "Mutations in the S4 Domain of a Pacemaker Channel Alter Its Voltage Dependence", FEBS Letters, 2000, vol. 479, pp. 35-40.

Chen et al., "Functional Roles of Charged Residues in the Putative Voltage Sensor of the HCN2 Pacemaker Channel", The Journal of Biological Chemistry, vol. 275, No. 46, Nov. 17, 2000, pp. 36465-36471.

Long et al., "Voltage Sensor of Kv1.2: Structural Basis of Electromechanical Coupling", Science, 2005, vol. 309, pp. 903-908.

Decher et al., "Voltage-Dependent Gating of Hyperpolarization-Activated, Cyclic Nucleotide-Gated Pacemaker Channels", The Journal of Biological Chemistry, Apr. 2, 2004, vol. 279, No. 14, pp. 13859-13865.

Zagotta et al., "Structural Basis for Modulation and Agonist Specificity of HCN Pacemaker Channels", Nature, vol. 425, Sep. 11, 2003, pp. 200-205.

Hamill et al., "Improved Patch-Clamp Techniques for High-Resolution Current Recording from Cells and Cell-Free Membrane Patches", Pflugers Arch., 1981, vol. 391 No. 2, pp. 85-100.

Bowie, et al., "Deciphering the Message in Protein Sequences: Tolerance to Amino Acid Substitutions", Science, 1990, vol. 247, pp. 1306-1310.

McCarty, Self-Complementary AAV Vectors; Advances and Applications, The American Society of Gene Therapy, vol. 16, No. 10, Oct. 2008, pp. 1648-1656.

Eguchi et al., "Efficient siRNA Delivery into Primary Cells by a Peptide Transduction Domain-dsRNA Binding Domain Fusion Protein", Nature Biotechnology, vol. 27, No. 6, Jun. 2009, pp. 567-572.

Wahl-Schott et al., "HCN Channels: Structure, Cellular Regulation and Physiological Function", Cellular and Molecular Life Sciences, vol. 66, 2009, pp. 470-494.

Discher et al., "Hypoxia Regulates B-Enolase and Pyruvate Kinase-M Promoters by Modulating Sp1/Sp3 Binding to a Conserved GC Element*", The Journal of Biological Chemistry, vol. 273, No. 40, Issue of Oct. 2, 1998, pp. 26087-26093, also available on line at http://www.jbc.org.

Zafarullah, et al., "Molecular Mechanisms of N-Acetylcysteine Actions", CMLS Cellular and Molecular Life Sciences, vol. 60, 2003, pp. 6-20.

Wadia et al., "Protein Transduction Technology", Analytical Biotechnology, 2002, vol. 13, pp. 52-56.

Prentice et al., "Regulated Expression of a Foreign Gene Targeted to the Ischamic Myocardium", Cardiovascular Research, vol. 35, 1997, pp. 567-574.

Prole et al., "Reversal of HCN Channel Voltage Dependence via Bridging of the S4-S5 Linker and Post S6", The Journal of General Physiology, vol. 128, No. 3, Sep. 2006, pp. 273-282.

\* cited by examiner

```
HCN3  ------------------------------------------------------------
HCN4  MDKLPPSMRKRLYSLPQQVGAKAWIMDEEEDAEEEGAGGRQDPSRRSIRLRPLPSPSPSA  60
HCN2  -----------------------MDARGGGGRPGESPGATPAPGPPPPPPPAPPQQQP   35
HCN1  ------------------------------------------------------------

HCN3  ------------------------------------------------------------
HCN4  AAGGTESRSSALGAADSEGPARGAGKSSTNGDCRRFRGSLASLGSRGGGSGGTGSGSSHG  120
HCN2  PPPPPPAPPPGPGPAPPQHPPRAEALPPEAADEGGPRGRLRSRDSSCGRPGTPGAASTAK   95
HCN1  ------------------------------MEGGGKPNSSSNSRDDGNSVFPAKASATG   29

HCN3  ----MEAEQR------------------PAAGASEGATP-------------GLEAVPPVAPPPATA   32
HCN4  HLHDSAEERRLIAEGDASPGEDRTPPGLAAEPERP-----------GASAQPAASPPPPQQ  170
HCN2  GSPNGECGRG----------EPQCSPAGPEGPARGPK----VSFSCRGAASGPAPGPGPAEE  143
HCN1  AGPAAAEKRLG---------------TPPGGGGAGAKEHGNSVCFKVDGGGGGGGGGGEEP   77
                        *..  .

HCN3  ASGPIPKSGPEP---------------------------------KRRHLGTLLQPTVNKFS   61
HCN4  PPQPASASCEQPSVDTAIKVEGGAAAGDQILPEAEVRLGQAGFMQRQFGAMLQPGVNKFS  230
HCN2  AGSEEAGPAGEP----------------------------RGSQASFMQRQFGALLQPGVNKFS  179
HCN1  AGGFEDAEGPRR------------------------------QYGFMQRQFTSMLQPGVNKFS  110
                                                  :*::  ::***  *****

HCN3  LRVFGSHKAVEIEQERVKSAGAWIIHPYSDFRFYWDLIMLLLMVGNLIVLPVGITFFKEE  121
HCN4  LRMFGSQKAVEREQERVKSAGFWIIHPYSDFRFYWDLTMLLLMVGNLIIIPVGITFFKDE  290
HCN2  LRMFGSQKAVEREQERVKSAGAWIIHPYSDFRFYWDFTMLLFMVGNLIIIPVGITFFKDE  239
HCN1  LRMFGSQKAVEKEQERVKTAGFWIIHPYSDFRFYWDLIMLIMMVGNLVIIPVGITFFTEQ  170
      **:***:****  ******:****************: **:;*****:::*******.::

HCN3  NSPPWIVFNVLSDTFFLLDLVLNFRTGIVVEEGAEILLAPRAIRTRYLRTWFLVDLISSI  181
HCN4  NTTPWIVFNVVSDTFFLIDLVLNFRTGIVVEDNTEIILDPQRIKMKYLKSWFMVDFISSI  350
HCN2  TTAPWIVFNVVSDTFFLMDLVLNFRTGIVIEDNTEIILDPEKIKKKYLRTWFVVDFVSSI  299
HCN1  TTTPWIIFNVASDTVFLLDLIMNFRTGTVNEDSSEIILDPKVIKMNYLKSWFVVDFISSI  230
      .:.***:***  ***.**:**::******  *  *:.:**:*  *:  ,**:;**:**::***

HCN3  PVDYIFLVVELEPRLDAEVYKTARALRIVRFTKILSLLRLLRLSRLIRYIHQWEEIFHMT  241
HCN4  PVDYIFLIVETR--IDSEVYKTARALRIVRFTKILSLLRLLRLSRLIRYIHQWEEIFHMT  408
HCN2  PVDYIFLIVEKG--IDSEVYKTARALRIVRFTKILSLLRLLRLSRLIRYIHQWEEIFHMT  357
HCN1  PVDYIFLIVEKG--MDSEVYKTARALRIVRFTKILSLLRLLRLSRLIRYIHQWEEIFHMT  288
      *******:**    : *:*****************************************

HCN3  YDLASAVVRIFNLIGMMLLLCHWDGCLQFLVPMLQDFPPDCWVSINHMVNHSWGRQYSHA  301
HCN4  YDLASAVVRIVNLIGMMLLLCHWDGCLQFLVPMLQDFPDDCWVSINNMVNNSWGKQYSYA  468
HCN2  YDLASAVMRICNLISMMLLLCHWDGCLQFLVPMLQDFPRNCWVSINGMVNHSWSELYSFA  417
HCN1  YDLASAVVRIFNLIGMMLLLCHWDGCLQFLVPLLQDFPPDCWVSINEMVNDSWGKQYSYA  348
      *******:**  ***.*****************:*****  :****** ***. **.*

HCN3  LFKAMSHMLCIGYGQQAPVGMPDVWLTMLSMIVGATCYAMFIGHATALIQSLDSSRRQYQ  361
HCN4  LFKAMSHMLCIGYGRQAPVGMSDVWLTMLSMIVGATCYAMFIGHATALIQSLDSSRRQYQ  528
HCN2  LFKAMSHMLCIGYGRQAPESMTDIWLTMLSMIVGATCYAMFIGHATALIQSLDSSRRQYQ  477
HCN1  LFKAMSHMLCIGYGAQAPVSMSDLWITMLSMIVGATCYAMFVGHATALIQSLDSSRRQYQ  408
      **************  ***  .*.*:*:****************::****.**:.  **.*
```

FIG. 1

```
HCN3   EKYKQVEQYMSFHKLPADTRQRIHEYYEHRYQGKMFDEESILGELSEPLREEIINFNCRG  421
HCN4   EKYKQVEQYMSFHKLPADTRQRIHDYYEHRYQGKMFDEESILGELSEPLREEIINFNCRK  588
HCN2   EKYKQVEQYMSFHKLPADFRQKIHDYYEHRYQGKMFDEDSILGELNGPLREEIVNFNCRK  537
HCN1   EKYKQVEQYMSFHKLPADMRQKIHDYYEHRYQGKIFDEENILNELNDPLREEIVNFNCRK  468
       *************.*.**:**:*********:***:.**.**. ******:**.**

HCN3   LVAHMPLFAHADPSFVTAVLTKLRFEVFQPGDLVVREGSVGRKMYFIQHGLLSVLARGAR  481
HCN4   LVASMPLFANADPNFVTSMLTKLRFEVFQPGDYIIREGTIGKKMYFIQHGVVSVLTKGNK  648
HCN2   LVASMPLFANADPNFVTAMLTKLKFEVFQPGDYIIREGTIGKKMYFIQHGVVSVLTKGNK  597
HCN1   LVATMPLFANADPNFVTAMLSKLRFEVFQPGDYIIREGAVGKKMYFIQHGVAGVITKSSK  528
       *** *****:***.***:::*:**:********* ::***::*:*********:  .*::.  :

HCN3   DTRLTDGSYFGEICLLTRGRRTASVRADTYCRLYSLSVDHFNAVLEEFPMMRRAFETVAM  541
HCN4   ETKLADGSYFGEICLLTRGRRTASVRADTYCRLYSLSVDNFNEVLEEYPMMRRAFETVAL  708
HCN2   EMKLSDGSYFGEICLLTRGRRTASVRADTYCRLYSLSVDNFNEVLEEYPMMRRAFETVAI  657
HCN1   EMKLTDGSYFGEICLLTKGRRTASVRADTYCRLYSLSVDNFNEVLEEYPMMRRAFETVAI  588
       : :*:************:*****************:** **** :***********:

HCN3   DRLLRIGKKNSILQRKRSEPSPG----SSGGIMEQHLVQHDRDMARGYRGRAPSTGAQLS  597
HCN4   DRLDRIGKKNSILLHKVQHDLNSGVFNYQENEIIQQIVQHDREMAHCAHRVQAAASATPT  768
HCN2   DRLDRIGKKNSILLHKVQHDLNSGVFNNQENAIIQEIVKYDREMVQQAELGQRVGLFPPP  717
HCN1   DRLDRIGKKNSILLQKFQKDLNTGVFNNQENEILKQIVKHDREMVQAIAPINYPQMTTLN  648
       *** ********* :* ..      . : :.:*::**:*.:

HCN3   GKPVLWEPLMHAPLQAAAVTSNVAIALTHQ---------RGP-----------------  630
HCN4   PTPVIWTPLIQAPLQAAAATTSVAIALTHHPRLPAAIFRPPPGSGLGNLGAGQTPRHLKR  828
HCN2   PPPPQVTSAIATLQQAAAMSFCPQVARPLVG-----------------------------  748
HCN1   STSSTTTPTSRMRTQSPPVYTATSLSHSNLHS----------------------------  680
       *  .     .    *:..    :: .

HCN3   ------------------------------------------LPLSPDSP--------  638
HCN4   LQSLIPSALGSASPASSPSQVDTPSSSSFHIQQLAGFSAPAGLSPLLPSSSSSPPPGACG  888
HCN2   ------------------------------------------PLALGSP--------  755
HCN1   ------------------------------------------PSPSTQTPQP-----  690
                                                  . :  :*

HCN3   ----------------ATLLA----------------------RSAWRSAGSPASP--  656
HCN4   SPSAPTPSAGVAATTIAGFGHFHKALGGSLSSSDSPLLTPLQPGARSPQAAQPSPAPPGA  948
HCN2   --------------RLVR------------------------RPPPGPAPAAASPG-  773
HCN1   --------------SAILS-----------------------PCSYTTAVCSPPV  708
                     :                                .  :  ..*

HCN3   -----------LVPVRAGPWASTS---------------------RLPAPP----  675
HCN4   RGGLGLPEHFLPPPPSSRSPSSSPGQLGQPPGELSLGLATGPLSTPETPPRQPEPPSLVA 1008
HCN2   --------------PPPPASPP-----------------------GAPASP------  787
HCN1   QSPLAARTFHYASPTASQLSLMQ---------------------QQPQQQ------  737
        . :.                                           *

HCN3   -----------------------ARTLHASLSRAGRSQVSLLGPPPGGGGRRLGP--  707
HCN4   GASGGASPMGFTPRGGLSPPGHSPGPPRTFPSAPPRASGSHGSLLLPPASSPPPPQVPQR 1068
HCN2   -------------------------RAPRTSPYGGLPAAPLAGP---ALPARRLSR--  815
HCN1   ------------------------VQQSQPPQTQPQQPSPQPQTPGSSTPKNEVH  768
                                :       .   .      *

HCN3   RGRP--------LSASQPSLPQR-----------------ATG  725
HCN4   RGTPPLTPGRLTQDLKLISASQPALPQDGAQTLRRASPHSSGESMAAFPLFPRAGGGSGG 1128
HCN2   ASRP--------LSASQPSLPHG-----------------APG  833
```

FIG. 1A

```
HCN1    KSTQALHNTNLTREVRPLSASQPSLPHEVSTLISRPHPTVG-----ESLASIPQPVTAVPG  824
            ;*****;**;                                              *

HCN3    DGSPG              RKGSGSERLPPSGLLAK        PPRTAQPPRPP  758
HCN4    SGSSGGLGPPGRPYGAIPGQHVTLPRKTSSGSLPPPLSLFGARATSSGGPPLTAGPQREP  1188
HCN2    PAAST              RPASSSTPRLGPTPAARAAAPSPDRRDSASPGAAG  873
HCN1    TGLQAG       GRSTVPQRVTLFRQMSSGAIPPNRGVPPAPPPPAAALPRESSSVLNT  877
                          *  *..                              :  .

HCN3    VPEPATPRGLQLSANM  774
HCN4    GARPEPVR-SKLPSNL  1203
HCN2    GLDPQDSARSRLSSNL  889
HCN1    DPDAEKPR---FASNL  890
            .        :.:*:
```

Consensus symbols

"*" means that the residues in that column are identical in all sequences in the alignment.

":" means that conserved substitutions have been observed, accordingly to the table below.

| AVFPMILW | Small (small+hydrophobic (incl.aromatic-Y)) |
| DE | Acidic |
| RK | Basic-H |
| STYHCNGQ | Hydroxyl + sulfhydryl + amine + G |
| Others | Unusual amino/imino acids etc |

"." means that semi-conserved substitutions are observed.

FIG. 1B

> HCN1 NM_021072 mRNA (SEQ ID NO:1)
ATGGAAGGAGGCGGCAAGCCCAACTCTTCGTCTAACAGCCGGGACGATGGCAACAGCGTCTTCCCCGCCA
AGGCGTCCGCGACGGGCGCGGGGCCGGCCGCGGCCGAGAAGCGCCTGGGCACCCCGCCGGGGGGCGGCGG
GGCCGGCGCGAAGGAGCACGGCAACTCCGTGTGCTTCAAGGTGGACGGCGGTGGCGGCGGTGGCGGCGGC
GGCGGCGGCGGCGAGGAGCCGGCGGGGGGCTTCGAAGACGCCGAGGGGCCCCGGCGGCAGTACGGCTTCA
TGCAGAGGCAGTTCACCTCCATGCTGCAGCCCGGGGTCAACAAATTCTCCCTCCGCATGTTTGGGAGCCA
GAAGGCGGTGGAAAAGGAGCAGGAAAGGGTTAAAACTGCAGGCTTCTGGATTATCCACCCTTACAGTGAT
TTCAGGTTTTACTGGGATTTAATAATGCTTATAATGATGGTTGGAAATCTAGTCATCATACCAGTTGGAA
TCACATTCTTTACAGAGCAAACAACAACACCATGGATTATTTTCAATGTGGCATCAGATACAGTTTTCCT
ATTGGACCTGATCATGAATTTTAGGACTGGGACTGTCAATGAAGACAGTTCTGAAATCATCCTGGACCCC
AAAGTGATCAAGATGAATTATTTAAAAAGCTGGTTTGTGGTTGACTTCATCTCATCCATCCCAGTGGATT
ATATCTTTCTTATTGTAGAAAAAGGAATGGATTCTGAAGTTTACAAGACAGCCAGGGCACTTCGCATTGT
GAGGTTTACAAAAATTCTCAGTCTCTTGCGTTTATTACGACTTTCAAGGTTAATTAGATACATACATCAA
TGGGAAGAGATATTCCACATGACATATGATCTCGCCAGTGCAGTGGTGAGAATTTTTAATCTCATCGGCA
TGATGCTGCTCCTGTGCCACTGGGATGGTTGTCTTCAGTTCTTAGTACCACTACTGCAGGACTTCCCACC
AGATTGCTGGGTGTCTTTAAATGAAATGGTTAATGATTCTTGGGGAAAGCAGTATTCATACGCACTCTTC
AAAGCTATGAGTCACATGCTGTGCATTGGGTATGGAGCCCAAGCCCCAGTCAGCATGTCTGACCTCTGGA
TTACCATGCTGAGCATGATCGTCGGGGCCACCTGCTATGCCATGTTTGTCGGCCATGCCACCGCTTTAAT
CCAGTCTCTGGATTCTTCGAGGCGGCAGTATCAAGAGAAGTATAAGCAAGTGGAACAATACATGTCATTC
CATAAGTTACCAGCTGATATGCGTCAGAAGATACATGATTACTATGAACACAGATACCAAGGCAAAATCT
TTGATGAGGAAAATATTCTCAATGAACTCAATGATCCTCTGAGAGAGGAGATAGTCAACTTCAACTGTCG
GAAACTGGTGGCTACAATGCCTTTATTTGCTAATGCGGATCCTAATTTTGTGACTGCCATGCTGAGCAAG
TTGAGATTTGAGGTGTTTCAACCTGGAGATTATATCATACGAGAAGGAGCCGTGGGTAAAAAAATGTATT
TCATTCAACACGGTGTTGCTGGTGTCATTACAAAATCCAGTAAAGAAATGAAGCTGACAGATGGCTCTTA
CTTTGGAGAGATTTGCCTGCTGACCAAAGGACGTCGTACTGCCAGTGTTCGAGCTGATACATATTGTCGT
CTTTACTCACTTTCCGTGGACAATTTCAACGAGGTCCTGGAGGAATATCCAATGATGAGGAGAGCCTTTG
AGACAGTTGCCATTGACCGACTAGATCGAATAGGAAAGAAAAATTCAATTCTTCTGCAAAAGTTCCAGAA
GGATCTGAACACTGGTGTTTTCAACAATCAGGAGAACGAAATCCTCAAGCAGATTGTGAAACATGACAGG
GAGATGGTGCAGGCAATCGCTCCCATCAATTATCCTCAAATGACAACCCTGAATTCCACATCGTCTACTA
CGACCCCGACCTCCCGCATGAGGACACAATCTCCACCGGTGTACACAGCGACCAGCCTGTCTCACAGCAA
CCTGCACTCCCCCAGTCCCAGCACACAGACCCCCCAGCCATCAGCCATCCTGTCACCCTGCTCCTACACC
ACCGCGGTCTGCAGCCCTCCTGTACAGAGCCCTCTGGCCGCTCGAACTTTCCACTATGCCTCCCCCACCG
CCTCCCAGCTGTCACTCATGCAACAGCAGCCGCAGCAGCAGGTACAGCAGTCCCAGCCGCCGCAGACTCA
GCCACAGCAGCCGTCCCCGCAGCCACAGACACCTGGCAGCTCCACGCCGAAAAATGAAGTGCACAAGAGC
ACGCAGGCGCTTCACAACACCAACCTGACCCGGGAAGTCAGGCCACTCTCCGCCTCGCAGCCCTCGCTGC
CCCATGAGGTGTCCACTCTGATTTCCAGACCTCATCCCACTGTGGGCGAGTCCCTGGCCTCCATCCCTCA
ACCCGTGACGGCGGTCCCCGGAACGGGCCTTCAGGCAGGGGCAGGAGCACTGTCCCGCAGCGCGTCACC
CTCTTCCGACAGATGTCGTCGGGAGCCATCCCCCCGAACCGAGGAGTCCCTCCAGCACCCCCTCCACCAG
CAGCTGCTCTTCCAAGAGAATCTTCCTCAGTCTTAAACACAGACCCAGACGCAGAAAAGCCACGATTTGC
TTCAAATTTATGA
> HCN1 NP_066550.2 (SEQ ID NO:2)
MEGGGKPNSSSNSRDDGNSVFPAKASATGAGPAAAEKRLGTPPGGGGAGAKEHGNSVCFKVDGGGGGGGG
GGGGEEPAGGFEDAEGPRRQYGFMQRQFTSMLQPGVNKFSLRMFGSQKAVEKEQERVKTAGFWIIHPYSD
FRFYWDLIMLIMMVGNLVIIPVGITFFTEQTTTPWIIFNVASDTVFLLDLIMNFRTGTVNEDSSEIILDP
KVIKMNYLKSWFVVDFISSIPVDYIFLIVEKGMDSEVYKTARALRIVRFTKILSLLRLLRLSRLIRYIHQ
WEEIFHMTYDLASAVVRIFNLIGMMLLLCHWDGCLQFLVPLLQDFPPDCWVSLNEMVNDSWGKQYSYALF
KAMSHMLCIGYGAQAPVSMSDLWITMLSMIVGATCYAMFVGHATALIQSLDSSRRQYQEKYKQVEQYMSF
HKLPADMRQKIHDYYEHRYQGKIFDEENILNELNDPLREEIVNFNCRKLVATMPLFANADPNFVTAMLSK
LRFEVFQPGDYIIREGAVGKKMYFIQHGVAGVITKSSKEMKLTDGSYFGEICLLTKGRRTASVRADTYCR
LYSLSVDNFNEVLEEYPMMRRAFETVAIDRLDRIGKKNSILLQKFQKDLNTGVFNNQENEILKQIVKHDR
EMVQAIAPINYPQMTTLNSTSSTTTPTSRMRTQSPPVYTATSLSHSNLHSPSPSTQTPQPSAILSPCSYT
TAVCSPPVQSPLAARTFHYASPTASQLSLMQQQPQQQVQQSQPPQYQPQQPSPQPQTPGSSTPKNEVHKS
TQALHNTNLTREVRPLSASQPSLPHEVSTLISRPHPTVGESLASIPQPVTAVPGTGLQAGGRSTVPQRVT
LFRQMSSGAIPPNRGVPPAPPPPAAALPRESSSVLNTDPDAEKPRFASNL //

FIG. 2

> HCN2 XM_001194 mRNA (SEQ ID NO: 3)
ATGGACGCGCGCGGGGCGGCGGGCGGCCCGGGGAGAGCCCGGGCGCGACCCCCGCGCCGGGGCCGCCGC
CGCCGCCGCCGCCCGCCCCCCCCAACAGCAGCCGCCGCCGCCGCCGCCGCCGCCCCCCGGGCCC
CGGGCCCGCGCCCCCCAGCACCCGCCCCGGGCCGAGGCGTTGCCCCGGAGGCGGCGGATGAGGGCGGC
CCGCGGGGCCGGCTCCCGCAGCCGGCACAGCTCGTGCGGCCGCCCCGGCACCCCGGCGCGGGCCAGCACGG
CCAAGGGCAGCCCGAACGGCGAGTGCGGGCGCGGCGAGCCGCAGTGCAGCCCCGCGGGGCCCGAGGGCCC
GGCGGGCGGCGCCCAAGGCTGTCGTTCTCGTGCCGGCGGCGCGCCTCCGGCCCTCGCCGGGGCCGGGCCG
GCGGAGGAGGCGGGCAGCGAGGAGGCGGGCCCGGCGGGGGAGCCGCGCGGCAGCCAGGCCAGCTTCATGC
AGCGCCAGTTCGGCGCGCTCCTGCAGCCGGGCGTCAACAAGTTCTCGCTGCGGATGTTCGGCAGCCAGAA
GGCCGTGGAGCGCGAGCAGGAGCGCGTCAAGTCGGCGGGGGCCTGGATCATCCACCCGTACAGCGACTTC
AGGTTCTACTGGGACTTCACCATGCTGCTGTTCATGGTGGGAAACCTCATCATCATCCCAGTGGGCATCA
CCTTCTTCAAGGATGAGACCACTGCCCCGTGGATCGTGTTCAACGTGGTCTCGGACACCTTCTTCCTCAT
GGACCTGGTGTTGAACTTCCGCACCGGCATTGTGATCGAGGACAACACGGAGATCATCCTGGACCCCGAG
AAGATCAAGAAGAAGTATCTGCGCACGTGGTTCGTGGTGGACTTCGTGTCCTCCATCCCGGTGGACTACA
TCTTCCTTATCGTGGAGAAGGGCATTGACTCCGAGGTCTACAAGACGGCACGCGCCCTGCGCATCGTGCG
CTTCACCAAGATCCTCAGCCTCCTGCGGCTGCTGCGCCTCTCACGCCTGATCCGCTACATCCATCAGTGG
GAGGAGATCTTCCACATGACCTATGACCTGGCCAGCGCGGTGATGAGGATCTGCAATCTCATCAGCATGA
TGCTGCTGCTCTGCCACTGGGACGGCTGCCTGCAGTTCCTGGTGCCTATGCTGCAGGACTTCCCGCGCAA
CTGCTGGGTGTCCATCAATGGCATGGTGAACCACTCGTGGAGTGAACTGTACTCCTTCGCACTCTTCAAG
GCCATGAGCCACATGCTGTGCATCGGGTACGGCCGGCAGGCGCCCGAGAGCATGACGGACATCTGGCTGA
CCATGCTCAGCATGATTGTGGGTGCCACCTGCTACGCCATGTTCATCGGCCACGCCACTGCCCTCATCCA
GTCGCTGGACTCCTCGCGGCGCCAGTACCAGGAGAAGTACAAGCAGGTGGAGCAGTACATGTCCTTCCAC
AAGCTGCCAGCTGACTTCCGGCAGAAGATCCACGACTACTATGAGCACCGGTACCAGGGCAAGATGTTTG
ACGAGGACAGCATCCTGGGCGAGCTCAACGGGCCCCTGCGGGAGGAGATCGTCAACTTCAACTGCCGGAA
GCTGGTGGCCTCCATGCCGCTGTTCGCCAACGCCGACCCCAACTTCGTCACGGCCATGCTGACCAAGCTC
AAGTTCGAGGTCTTCCAGCCGGGTGACTACATCATCCGCGAAGGCACCATCGGGAAGAAGATGTACTTCA
TCCAGCACGGCGTGGTCAGCGTGCTCACTAAGGGCAACAAGGAGATGAAGCTGTCCGATGGCTCCTACTT
CGGGGAGATCTGCCTGCTCACCCGGGGCCGCCGCACGGCGAGCGTGCGGGCTGACACCTACTGCCGCCTC
TATTCGCTGAGCGTGGACAACTTCAACGAGGTGCTGGAGGAGTACCCCATGATGCGGCGCGCCTTCGAGA
CGGTGGCCATCGACCGCCTGGACCGCATCGGCAAGAAGAATTCCATCCTCCTGCACAAGGTGCAGCATGA
CCTCAACTCGGGCGTATTCAACAACCAGGAGAACGCCATCATCCAGGAGATCGTCAAGTACGACCGCGAG
ATGGTGCAGCAGGCCGAGCTGGGTCAGCGCGTGGGCCTCTTCCCGCCGCCGCCGCCGCCGCCGCAGGTCA
CCTCGGCCATCGCCACGCTGCAGCAGGCGGCGGCCATGAGCTTCTGCCCGCAGGTGGCGCGGCCGCTCGT
GGGGCCGCTGGCCCTCGGCTCCCCGCGCCTCGTGCGCCGCCCGCCCCGGGCGCCGCACCTGCCGCCGCC
TCACCCGGGCCCCCGGGCCCCCCGCCAGCCCCCCGGGCGCGGCCGCCAGCCCCTGGGCACGGCGGACCTCGC
CCTACGGCGGCCTGCCCGCCGCGCCCCTTGCTGGGCCCGCCCTGCCCGCGCGCCGCCTGAGCCGCGCTC
GCGCCCACTGTCCGCCTCGCAGCCCTCGCTGCCCTCACGGCGCCCCCGGCCCCGCGCCCTCCACACGCCCG
GCCAGCAGCTCCACACCGCGCTTGGGCCCACGCCCGCTGCCCGGCCGCCGCGCCCAGCCCGGACCGCA
GGGACTCGGCCTCACCCGGCCGCCGCCCCGGCGGCCTGGACCCCAGGACTCCGCCGCGTTGGCGCCTCTCGTC
CAACTTGTGA
> HCN2 NP_001185.3 (SEQ ID NO: 4)
MDARGGGGRPGESPGATPAPGPPPPPPPAPPQQQPPPPPPAPPPGPGPAPPQHPPRAEALPPEAADEGG
PRGRLRSRDSSCGRPGTPGAASTAKGSPNGECGRGEPQCSPAGPEGPARGPKVSFSCRGAASGPAPGPGP
AEEAGSEEAGPAGEPRGSQASFMQRQFGALLQPGVNKFSLRMFGSQKAVEREQERVKSAGAWIIHPYSDF
RFYWDFTMLLFMVGNLIIIPVGITFFKDETTAPWIVFNVVSDTFFLMDLVLNFRTGIVIEDNTEIILDPE
KIKKKYLRTWFVVDFVSSIPVDYIFLIVEKGIDSEVYKTARALRIVRFTKILSLLRLLRLSRLIRYIHQW
EEIFHMTYDLASAVMRICNLISMMLLLCHWDGCLQFLVPMLQDFPRNCWVSINGMVNHSWSELYSFALFK
AMSHMLCIGYGRQAPESMTDIWLTMLSMIVGATCYAMFIGHATALIQSLDSSRRQYQEKYKQVEQYMSFH
KLPADFRQKIHDYYEHRYQGKMFDEDSILGELNGPLREEIVNFNCRKLVASMPLFANADPNFVTAMLTKL
KFEVFQPGDYIIREGTIGKKMYFIQHGVVSVLTKGNKEMKLSDGSYFGEICLLTRGRRTASVRADTYCRL
YSLSVDNFNEVLEEYPMMRRAFETVAIDRLDRIGKKNSILLHKVQHDLNSGVFNNQENAIIQEIVKYDRE
MVQQAELGQRVGLFPPPPPPPQVTSAIATLQQAAAMSFCPQVARPLVGPLALGSPRLVRKPPPGPAPAAA
SPGPPPPASPPGAPASPRAPRTSPYGGLPAAPLAGPALPARRLSRASRPLSASQPSLPHGAPGPAASTRP
ASSSTPRLGPTPAARAAAPSPDRRDSASPGAAGGLDPQDSARSRLSSNL //

FIG. 2A

> HCN3 NM_020897 mRNA (SEQ ID NO:5)
ATGGAGGCAGAGCAGCGGCCGGCCGCGGGGGCCAGCGAAGGGGCGACCCCTGGACTGGAGGCGGTGCCTC
CCGTTGCTCCCCCGCCTGCGACCGCGGCCTCAGGTCCGATCCCCAAATCTGGGCCTCAGCCTAAGAGGAG
GCACCTTGGGACGCTGCTCCAGCCTACGGTCAACAAGTTCTCCCTTCGGGTGTTCGGCAGCCACAAAGCA
GTGGAAATCGAGCAGGAGCGGGTGAAGTCAGCGGGGGCCTGGATCATCCACCCCTACAGCGACTTCCGGT
TTTACTGGGACCTGATCATGCTGCTGCTGATGGTGGGGAACCTCATCGTCCTGCCTGTGGGCATCACCTT
CTTCAAGGAGGAGAACTCCCCGCCTTGGATCGTCTTCAACGTATTGTCTGATACTTTCTTCCTACTGGAT
CTGGTGCTCAACTTCCGAACGGGCATCGTGGTGGAGGAGGGTGCTGAGATCCTGCTGGCACCGCGGGCCA
TCCGCACGCGCTACCTGCGCACCTGGTTCCTGGTTGACCTCATCTCTTCTATCCCTGTGGATTACATCTT
CCTAGTGGTGGAGCTGGAGCCACGTTGGACGCTGAGGTCTACAAAACGGCACGGGCCCTACGCATCGTT
CGCTTCACCAAGATCCTAAGCCTGCTGAGGCTGCTCCGCCTCTCCCGCCTCATCCGCTACATACACCAGT
GGGAGGAGATCTTTCACATGACCTATGACCTGGCCAGTGCTGTGGTTCGCATCTTCAACCTCATTGGGAT
GATGCTGCTGCTATGTCACTGGGATGGCTGTCTGCAGTTCCTGGTGCCCATGCTGCAGGACTTCCCTCCC
GACTGCTGGGTCTCCATCAACCACATGGTGAACCACTCGTGGGGCCGCCAGTATTCCCATGCCCTGTTCA
AGGCCATGAGCCACATGCTGTGCATTGGCTATGGGCAGCAGGCACCTGTAGGCATGCCCGACGTCTGGCT
CACCATGCTCAGCATGATCGTAGGTGCCACATGCTACGCCATGTTCATCGGCCATGCCACGGCACTCATC
CAGTCCCTGGACTCTTCCCGGCGTCAGTACCAGGAGAAGTACAAGCAGGTGGAGCAGTACATGTCCTTCC
ACAAGCTGCCAGCAGACACGCGGCAGCGCATCCACGAGTACTATGAGCACCGCTACCAGGGCAAGATGTT
CGATGAGGAAAGCATCCTGGGCGAGCTGAGCGAGCCGCTTCGCGAGGAGATCATTAACTTCACCTGTCGG
GGCCTGGTGGCCCACATGCCGCTGTTTGCCCATGCCGACCCCAGCTTCGTCACTGCAGTTCTCACCAAGC
TGCGCTTTGAGGTCTTCCAGCCGGGGGATCTCGTGGTGCGTGAGGGCTCCGTGGGGAGGAAGATGTACTT
CATCCAGCATGGGCTGCTCAGTGTGCTGGCCCGCGGCGCCCGGGACACACGCCTCACCGATGGATCCTAC
TTTGGGGAGATCTGCCTGCTAACTAGGGGCCGGCGCACAGCCAGTGTTCGGGCTGACACCTACTGCCGCC
TTTACTCACTCAGCGTGGACCATTTCAATGCTGTGCTTGAGGAGTTCCCCATGATGCGCCGGGCCTTTGA
GACTGTGGCCATGGATCGGCTGCTCCGCATCGGCAAGAAGAATTCCATACTGCAGCGGAAGCGCTCCGAG
CCAAGTCCAGGCAGCAGTGGTGGCATCATGGAGCAGCACTTGGTGCAACATGACAGAGACATGGCTCGGG
GTGTTCGGGGTCGGGCCCCGAGCACAGGAGCTCAGCTTAGTGGAAAGCCAGTACTGTGGGAGCCACTGGT
ACATGCGCCCCTTCAGGCAGCTGCTGTGACCTCCAATGTGGCCATTGCCCTGACTCATCAGCGGGGCCCT
CTGCCCCTCTCCCCTGACTCTCCAGCCACCCTCCTTGCTCGCTCTGCTTGGCGCTCAGCAGGCTCTCCAG
CTTCCCCGCTGGTGCCCGTCCGAGCTGGCCCATGGGCATCCACCTCCCGCCTGCCCGCCCCACCTGCCCG
AACCCTGCACGCCAGCCTATCCCGGGCAGGGCGCTCCCAGGTCTCCCTGCTGGGTCCCCCTCCAGGAGGA
GGTGGACGGCGGCTAGGACCTCGGGGCCGCCCACTCTCAGCCTCCCAACCCTCTCTGCCTCAGCGGGCAA
CAGGCGATGGCTCTCCTGGGCGTAAGGGATCAGGAAGTGAGCGGCTGCCTCCCTCAGGGCTCCTGGCCAA
ACCTCCAAGGACAGCCCAGCCCCCAGGCCACCAGTGCCTGAGCCAGCCACACCCCGGGGTCTCCAGCTT
TCTGCCAACATGTAA

> HCN3 NP_065948.1 (SEQ ID NO:6)
MEAEQRPAAGASEGATPGLEAVPPVAPPPATAASGPIPKSGPEPKRRHLGTLLQPTVNKFSLRVFGSHKA
VEIEQERVKSAGAWIIHPYSDFRFYWDLIMLLLMVGNLIVLPVGITFFKEENSPPWIVFNVLSDTFFLLD
LVLNFRTGIVVEEGAEILLAPRAIRTRYLRTWFLVDLISSIPVDYIFLVVELEPRLDAEVYKTARALRIV
RFTKILSLIRLLRLSRLIRYIHQWEEIFHNTYDLASAVVRIFNLIGMMLLLCHWDGCLQFLVPMLQDFPP
DCWVSINHMVNHSWGRQYSHALFKAMSHMLCIGYGQQAPVGMPDVWLTMLSMIVGATCYAMFIQHATALI
QSLDSSRRQYQEKYKQVEQYMSFHKLPADTRQRIHEYYEHRYQGKMFDEESILGELSEPLREEIINFTCR
GLVAHMPLFAHADPSFVTAVLTKLRFEVFQPGDLVVREGSVGRKMYFIQHGLLSVLARGARDTRLIDGSY
FGEICLLTRGRRTASVRADTYCRLYSLSVDHFNAVLEEFPMMRRAFETVAMDRLLRIGKKNSILQRKRSE
PSPGSSGGIMEQHLVQHDRDMARGVRGRAPSTQAQLSGKPVLWEPLVHAPLQAAAVTSNVAIALTHQRGP
LPLSPDSPATLLARSAWRSAGSPASPLVPVRACPWASTSRLPAPPARTLHASLSRAGRSQVSLLGPPPGG
GGRRLGPRGRPLSASQPSLPQRATGDGSPGRKCSGSERLPPSGLLAKPPRTAQPPRPPVPEPATPRGLQL
SANM  //

FIG. 2B

> HCN4 NM_005477 (SEQ ID NO:7)
ATGGACAAGCTGCCGCCGTCCATGCGCAAGCGGCTCTACAGCCTCCCGCAGCAGGTGGGGGCCAAGGCGT
GGATCATGGACGAGGAAGAGGACGCCGAGGAGGAGGGGGCCGGGGGCCGCCAAGACCCCAGCCGCAGGAG
CATCCGGCTGCGGCCACTGCCCTCGCCCTCCCCCTCGGCGGCCGCGGGTGGCACGGAGTCCCGGAGCTCG
GCCCTCGGGGCAGCGGACAGCGAAGGGCCGGCCCGCGGCGCGGGCAAGTCCAGCACGAACGGCGACTGCA
GGCGCTTCCGCGGGAGCCTGGCCCTCGCTGGGCAGCCGGGCGGCGGCAGCGGCGGCACGGGAGCGGCAG
CAGTCACGGACACCTGCATGACTCCGCGGAGGAGCGGCGGCTCATCGCCGAGGGCGACGCGTCCCCCGGC
GAGGACAGGACGCCCCAGGCCTGGCGGCCGAGCCCGAGCGCCCCGGCGCCTCGGCGCAGCCCGCAGCCT
CGCCGCCGCCGCCCCAGCAGCCACCGCAGCCGGCCTCCGCCTCCTGCGAGCAGCCCTCGGTGGACACCGC
TATCAAAGTGGAGGGAGGCGCGGCTGCCGGCGACCAGATCCTCCCGGAGGCCGAGGTGCGCCTGGGCCAG
GCCGGCTTCATGCAGCGCCAGTTCGGGGCCATGCTCCAACCCGGGGTCAACAAATTCTCCCTAAGGATGT
TCGGCAGCCAGAAAGCCGTGGAGCGCGAACAGGAGAGGGTCAAGTCGGCCCGATTTTGGATTATCCACCC
CTACAGTGACTTCAGATTTTACTGGGACCTGACCATGCTGCTGCTGATGGTGGGAAACCTGATTATCATT
CCTGTGGGCATCACCTTCTTCAAGGATGAGAACACCACACCCTGGATTGTCTTCAATGTGGTGTCAGACA
CATTCTTCCTCATCGACTTGGTCCTCAACTTCCGCACAGGGATCGTGGTGGAGGACAACACAGAGATCAT
CCTGGACCCCGCAGCGGATTAAAATGAAGTACCTGAAAAGCTGGTTCATGGTAGATTTCATTTCCTCCAT
CCCCGTGGACTACATCTTCCTCATTGTGGAGACACGCATCGACTCGGAGGTCTACAAGACTGCCCGGGCC
TGCGGCATTGTCCGCTTCACGAAGATCCTCAGCCTCTTACGCCTGTTACGCCTCTCCCGCCTCATTCGATA
TATTCACCAGTGGGAAGAGATCTTCCACATGACCTACGACCTGGCCAGCGCCGTGGTGCGCATCGTGAAC
CTCATCGGCATGATGCTCCTGCTCTGCCACTGGGACGGCTGCCTGCAGTTCCTGGTACCCATGCTACAGG
ACTTCCCTGACGACTGCTGGGTGTCCATCAACAACATGGTGAACAACTCCTGGGGGAAGCAGTACTCCTA
CGCGCTCTTTCAAGGCCATGAGCCACATGCTGTGCATCGGCTACGGCGGCAGGCGCCCGTGGGCATGTCC
GACGTCTGGCTCACCATGCTCAGCATGATCGTGGGTGCCACCTGCTACGCCATGTTCATTGGCCACGCCA
CTGCCCTCATCCAGTCCCTGGACTCCTCCCGGCGCCAGTACCAGGAAAAGTACAAGCAGGTGGAGCAGTA
CATGTCCTTTCACAAGCTCCCGCCCGACACCCGGCAGCGCATCCACGACTACTACGAGCACCGCTACCAG
GGCAAGATGTTCGACGAGGAGAGCATCCTGGGCGAGCTAAGCGAGCCCCTGCGGGAGGAGATCATCAACT
TTAACTGTCGGAAGCTGGTGGCCTCCATGCCACTGTTTGCCAATGCGGACCCCAACTTCGTGACGTCCAT
GCTGACCAAGCTGCGTTTCGAGGTCTTCCAGCCTGGGGACTACATCATCCGGGAAGGCACCATTGGCAAG
AAGATGTACTTCATCCAGCATGGCGTGGTCAGCGTGCTCACCAAGGGCAACAAGGAGACCAAGCTGGCCG
ACGGCTCCTACTTTGGAGAGATCTGCCTGCTGACCCGGGGCCGGCGCACAGCCAGCGTGAGGGCCGACAC
CTACTGCCGCCTCTACTCGCTGAGCGTGGACAACTTCAATGAGGTGCTGGAGGAGTACCCCATGATGCGA
AGGGCCTTCGAGACCGTGGCGCTGGACCGCCTGGACCGCATTGGCAAGAAGAACTCCATCCTCCTCCACA
AAGTCCAGCACGACCTCAACTCCGGCGTCTTCAACTACCAGGAGAATGAGATCATCCAGCAGATTGTGCA
GCATGACCGGGAGATGGCCCACTGCGCGCACCGCGTCCAGGCTGCTGCCTCTGCCACCCCAACCCCCACG
CCCGTCATCTGGACCCCGCTGATCCAGGCACCACTGCAGGCTGCCGCTGCCACCACTTCTGTGGCCATAG
CCCTCACCCACCACCCTCGCCTGCCTGCTGCCATCTTCCGCCCTCCCCCAGGATCTGGGCTGGGCAACCT
CGGTGCCGGGCAGACGCCAAGGCACCTGAAACGGCTGCAGTCCCTGATCCCTTCTGCGCTGGGCTCCGCC
TCGCCCGCCAGCAGCCCGTCCCAGGTGGACACACCGTCTTCATCCTCCTTCCACATCCAACAGCTGGCTG
GATTCTCTGCCCCCGCTGGACTGAGCCCACTCCTGCCCTCATCCAGCTCCTCCCCACCCCCCGGGGCCTG
TGGCTCCCCCTCGGCTCCCACACCATCAGCTGGCGTAGCCGCCACCACCATAGCCGGGTTTGGCCACTTC
CACAAGGCGCTGGGTGGCTCCCTGTCCTCCTCCGACTCTCCCCTGCTCACCCCGCTGCAGCCAGGCGCCC
GCTCCCCGCAGGCTGCCCAGCCATCTCCCGCGCCACCCGGGGCCCGGGGAGGCCTGGGACTCCGGAGCA
CTTCCTGCCACCCCCACCCTCATCCAGATCCCCGTCATCTAGCCCCGGGCAGCTGGGCCAGCCTCCCGGG
GAGTTGTCCCTAGGTCTGGCCACTGGCCCACTGAGCACGCCAGAGACACCCCACGGCAGCCTGAGCCGC
CGTCCCTTGTGGCAGGGGCCTCTGGGGGGGCTTCCCCTGTAGGCTTTACTCCCCGAGGAGGTCTCAGCCC
CCCTGGCCACAGCCCAGGCCCCCAAGAACCTTCCCGAGTGCCCCGCCCCGGGCCTCTGGCTCCCACGGA
TCCTTGCTCCTGCCACCTGCATCCAGCCCCCACCACCCCAGGTCCCCCAGCGCCGGGGCACACCCCGC
TCACCCCCGGCCGCCTCACCCAGGACCCTCAAGCTCATCTCCGCGTCTCAGCCAGCCCTGCCTCAGGACGG
GCGCAGACTCTCCGCAGAGCCTCCCCGCACTCCTCAGGGGAGTCCATGGCTGCCTTCCCGCTCTTCCCC
AGGGCTGGGGTGGCAGCGGGGCAGTGGGAGCAGCGGGGCCTCGGTCCCCTGGGAGGCCCTATGGTG
CCATCCCCGGCCAGCACGTCACTCTGCCTCGGAAGACATCCTCAGGTTCTTTGCCACCCCCTCTGTCTTT
GTTTGGGGCAAGAGCCACCTCTTCTGGGGGGCCCCTCTGACTGCTGGACCCCAGAGGGAACCTGGGGCC
AGGCCTGAGCCAGTGCGCTCCAAACTGCCATCCAATCTATGA

FIG. 2C

> HCN4 NP_005468.1 (SEQ ID NO:8)
MDKLPPSMRKRLYSLPQQVGAKAWIMDEEEDAEEEGAGGRQDPSRRSIRLRPLPSPSPSAAAGGTESRSS
ALGAADSEGPARGAGKSSTNGDCRPFRGSLASLGSRGGGSGGTGSGSSHGHLHDSAEERRLIAEGDASPG
EDRTPPGLAAEPERPGASAQPAASPPPPQQPPQPASASCEQPSVDTAIKVEGGAAAGDQILPEAEVRLGQ
AGFMQRQFGAMLQPGVNKFSLRMFGSQRAVEREQERVKSAGFWIIHPYSDFRFYWDLTMLLLMVGNLIII
PVGITFFKDENTTPWIVFNVVSDIFFLIDLVLNFRTGIVVEDNTEIILDPQRIKMKYLKSWFMVDFISSI
PVDYIFLIVETRIDSEVYKTARALRIVRFTKILSLLRLLRLSRLIRYIHQWEEIFHMTYDLASAVVRIVN
LIGMMLLLCHWDGCLQFLVPMLQDFPDDCWVSINNMVNNSWGKQYSYALFKAMSHMLCIGYGRQAPVGMS
DVWLTMLSMIVGATCYAMFIGHATALIQSLDSSRRQYQEKYKQVEQYMSFHKLPPDTRQRIHDYYEHRYQ
GKMFDEESILGELSEPLREEIINFNCRKLVASMPLFANADPNFVTSMLTKLRFEVFQPGDYIIREGTIGK
KMYFIQHGVVSVLTKGNKETKLADGSYFGEICLLTRGRRTASVRADTYCRLYSLSVDNFNEVLEEYPMMR
RAFETVALDRLDRIGKKNSILLHKVQHDLNSGVFNYQENEIIQQIVQHDREMAHCAHRVQAAASATPTPT
PVIWTPLIQAPLQAAAATTSVAIALTHHPRLPAAIFRPPPGSGLGNLGAGQTPKHLKRLQSLIPSALGSA
SPASSPSQVDTPSSSSFHIQQLAGFSAPAGLSPLLPSSSSSPPPGACGSPSAPTPSAGVAATTIAGFGHF
HKALGGSLSSSDSPLLTPLQPGARSPQAAQPSPAPPGARGGLGLPEHFLPPPPSSRSPSSSPGQLGQPPG
ELSLGLATGPLSTPETPPRQPEPPSLVAGASGGASPVGFTPRGGLSPPGHSPGPPRTFPSAPPRASGSHG
SLLLPPASSPPPPQVPQRRGTPPLTPGRLTQDLKLISASQPALPQDGAQTLRRASPHSSGESMAAFPLFP
RAGGGSGGSGSSGGLGPPGRPYGAIPGQHVTLPRKTSSGSLPPPLSLFGARATSSGGPPLTAGPQREPGA
RPEPVRSKLPSNL

FIG. 2D hHCN4wt  3612 bp    N'[                              ]C'
hHCN4t   2214 bp    N'[                ]C'
hHCN4st1 1575 bp         N'[         ]C'
hHCN4st2 1554 bp         N'[         ]C'
hHCN4st3 1518 bp           N'[       ]C'

FIG. 6

```
         10         20         30         40         50         60
          |          |          |          |          |          |
AGTCGACGGTACCGCGGGCCCAGCTTGGTACCGAGCTCGGATCCACTAGTAACGGCCGCC

S  R  R  Y  R  G  P  S  L  V  P  S  S  D  P  L  V  T  A  A 70         80         90        100        110        120
          |          |          |          |          |          |
                                 Start
AGTGTGCTGGAATTCGCCTCGCCATGGACAAGCTGCCGCCGTCCATGCGCAAGCGGCTC

S  V  L  E  F  R  L  A  M  D  K  L  P  P  S  M  R  K  R  L 130        140        150        160        170        180
          |          |          |          |          |          |
TACAGCCTCCCGCAGCAGGTGGGGGCCAAGGCGTGGATCATGGACGAGGAAGAGGACGCC

Y  S  L  P  Q  Q  V  G  A  K  A  W  I  M  D  E  E  E  D  A 190        200        210        220        230        240
          |          |          |          |          |          |
GAGGAGGAGGGGGCCGGGGGCCGCCAAGACCCCAGCCGCAGGAGCATCCGGCTGCGGCCA

E  E  E  G  A  G  G  R  Q  D  P  S  R  R  S  I  R  L  R  P 250        260        270        280        290        300
          |          |          |          |          |          |
CTGCCCTCGCCCTCCCCCTCGGCGGCCGCGGGTGGCACGGAGTCCCGGAGCTCGGCCCTC

L  P  S  P  S  P  S  A  A  A  G  G  T  E  S  R  S  S  A  L 310        320        330        340        350        360
          |          |          |          |          |          |
GGGGCAGCGGACAGCGAAGGGCCGGCCCGCGGCGCGGGCAAGTCCAGCACGAACGGCGAC

G  A  A  D  S  E  G  P  A  R  G  A  G  K  S  S  T  N  G  D 370        380        390        400        410        420
          |          |          |          |          |          |
TGCAGGCGCTTCCGCGGGAGCCTGGCCTCGCTGGGCAGCCGGGGCGGCGGCAGCGGCGGC

```
          430       440       450       460       470       480
           |         |         |         |         |         |
         ACGGGGAGCGGCAGCAGTCACGGACACCTGCATGACTCCGCGGAGGAGCGGCGGCTCATC
           T  G  S  G  S  S  H  G  H  L  H  D  S  A  E  E  R  R  L  I
          490       500       510       520       530       540
           |         |         |         |         |         |
         GCCGAGGGCGACGCGTCCCCCGGCGAGGACAGGACGCCCCCAGGCCTGGCGGCCGAGCCC
           A  E  G  D  A  S  P  G  E  D  R  T  P  P  G  L  A  A  E  P
          550       560       570       580       590       600
           |         |         |         |         |         |
         GAGCGCCCCGGCGCCTCGGCGCAGCCCGCAGCCTCGCCGCCGCCGCCCCAGCAGCCACCG
           E  R  P  G  A  S  A  Q  P  A  A  S  P  P  P  P  Q  Q  P  P
          610       620       630       640       650       660
           |         |         |         |         |         |
         CAGCCGGCCTCCGCCTCCTGCGAGCAGCCCTCGGTGGACACCGCTATCAAAGTGGAGGGA
           Q  P  A  S  A  S  C  E  Q  P  S  V  D  T  A  I  K  V  E  G
          670       680       690       700       710       720
           |         |         |         |         |         |
         GGCGCGGCTGCCGGCGACCAGATCCTCCCGGAGGCCGAGGTGCGCCTGGGCCAGGCCGGC
           G  A  A  A  G  D  Q  I  L  P  E  A  E  V  R  L  G  Q  A  G
          730       740       750       760       770       780
           |         |         |         |         |         |
         TTCATGCAGCGCCAGTTCGGGGCCATGCTCCAACCCGGGGTCAACAAATTCTCCCTAAGG
           F  M  Q  R  Q  F  G  A  M  L  Q  P  G  V  N  K  F  S  L  R
          790       800       810       820       830       840
           |         |         |         |         |         |
         ATGTTCGGCAGCCAGAAAGCCGTGGAGCGCGAACAGGAGAGGGTCAAGTCGGCCGGATTT
           M  F  G  S  Q  K  A  V  E  R  E  Q  E  R  V  K  S  A  G  F
          850       860       870       880       890       900
           |         |         |         |         |         |
         TGGATTATCCACCCCTACAGTGACTTCAGATTTTACTGGGACCTGACCATGCTGCTGCTG
           W  I  I  H  P  Y  S  D  F  R  F  Y  W  D  L  T  M  L  L  L
          910       920       930       940       950       960
           |         |         |         |         |         |
         ATGGTGGGAAACCTGATTATCATTCCTGTGGGCATCACCTTCTTCAAGGATGAGAACACC
           M  V  G  N  L  I  I  I  P  V  G  I  T  F  F  K  D  E  N  T
```

FIG. 15A

```
              970       980       990      1000      1010      1020
               |         |         |         |         |         |
         ACACCCTGGATTGTCTTCAATGTGGTGTCAGACACATTCTTCCTCATCGACTTGGTCCTC
           T  P  W  I  V  F  N  V  V  S  D  T  F  F  L  I  D  L  V  L 1030      1040      1050      1060      1070      1080
               |         |         |         |         |         |
         AACTTCCGCACAGGGATCGTGGTGGAGGACAACACAGAGATCATCCTGGACCCGCAGCGG
           N  F  R  T  G  I  V  V  E  D  N  T  E  I  I  L  D  P  Q  R 1090      1100      1110      1120      1130      1140
               |         |         |         |         |         |
         ATTAAAATGAAGTACCTGAAAAGCTGGTTCATGGTAGATTTCATTTCCTCCATCCCCGTG
           I  K  M  K  Y  L  K  S  W  F  M  V  D  F  I  S  S  I  P  V 1150      1160      1170      1180      1190      1200
               |         |         |         |         |         |
         GACTACATCTTCCTCATTGTGGAGACACGCATCGACTCGGAGGTCTACAAGACTGCCCGG
                                   ┌─S3-S3-linker: wildtype─┐
           D  Y  I  F  L  I  V  │  E  T  R  I  D  S  E  V  Y │ K  T  A  R
                                   └─────────────────────────┘

1210      1220      1230      1240      1250      1260
               |         |         |         |         |         |
         GCCCTGCGCATTGTCCGCTTCACGAAGATCCTCAGCCTCTTACGCCTGTTACGCCTCTCC
           A  L  R  I  V  R  F  T  K  I  L  S  L  L  R  L  L  R  L  S 1270      1280      1290      1300      1310      1320
               |         |         |         |         |         |
         CGCCTCATTCGATATATTCACCAGTGGGAAGAGATCTTCCACATGACCTACGACCTGGCC
           R  L  I  R  Y  I  H  Q  W  E  E  I  F  H  M  T  Y  D  L  A 1330      1340      1350      1360      1370      1380
               |         |         |         |         |         |
         AGCGCCGTGGTGCGCATCGTGAACCTCATCGGCATGATGCTCCTGCTCTGCCACTGGGAC
           S  A  V  V  R  I  V  N  L  I  G  M  M  L  L  L  C  H  W  D 1390      1400      1410      1420      1430      1440
               |         |         |         |         |         |
         GGCTGCCTGCAGTTCCTGGTACCCATGCTACAGGACTTCCCTGACGACTGCTGGGTGTCC
           G  C  L  Q  F  L  V  P  M  L  Q  D  F  P  D  D  C  W  V  S 1450      1460      1470      1480      1490      1500
               |         |         |         |         |         |
         ATCAACAACATGGTGAACAACTCCTGGGGGAAGCAGTACTCCTACGCGCTCTTCAAGGCC
           I  N  N  M  V  N  N  S  W  G  K  Q  Y  S  Y  A  L  F  K  A
```

FIG. 15B

```
          1510      1520      1530      1540      1550      1560
            |         |         |         |         |         |
ATGAGCCACATGCTGTGCATCGGCTACGGGCGGCAGGCGCCCGTGGGCATGTCCGACGTC
 M  S  H  M  L  C  I  G  Y  G  R  Q  A  P  V  G  M  S  D  V 1570      1580      1590      1600      1610      1620
            |         |         |         |         |         |
TGGCTCACCATGCTCAGCATGATCGTGGGTGCCACCTGCTACGCCATGTTCATTGGCCAC
 W  L  T  M  L  S  M  I  V  G  A  T  C  Y  A  M  F  I  G  H 1630      1640      1650      1660      1670      1680
            |         |         |         |         |         |
GCCACTGCCCTCATCCAGTCCCTGGACTCCTCCCGGCGCCAGTACCAGGAAAAGTACAAG
 A  T  A  L  I  Q  S  L  D  S  S  R  R  Q  Y  Q  E  K  Y  K 1690      1700      1710      1720      1730      1740
            |         |         |         |         |         |
CAGGTGGAGCAGTACATGTCCTTTCACAAGCTCCCGCCCGACACCCGGCAGCGCATCCAC
 Q  V  E  Q  Y  M  S  F  H  K  L  P  P  D  T  R  Q  R  I  H 1750      1760      1770      1780      1790      1800
            |         |         |         |         |         |
GACTACTACGAGCACCGCTACCAGGGCAAGATGTTCGACGAGGAGAGCATCCTGGGCGAG
 D  Y  Y  E  H  R  Y  Q  G  K  M  F  D  E  E  S  I  L  G  E 1810      1820      1830      1840      1850      1860
            |         |         |         |         |         |
CTAAGCGAGCCCCTGCGGGAGGAGATCATCAACTTTAACTGTCGGAAGCTGGTGGCCTCC
 L  S  E  P  L  R  E  E  I  I  N  F  N  C  R  K  L  V  A  S 1870      1880      1890      1900      1910      1920
            |         |         |         |         |         |
ATGCCACTGTTTGCCAATGCGGACCCCAACTTCGTGACGTCCATGCTGACCAAGCTGCGT
 M  P  L  F  A  N  A  D  P  N  F  V  T  S  M  L  T  K  L  R 1930      1940      1950      1960      1970      1980
            |         |         |         |         |         |
TTCGAGGTCTTCCAGCCTGGGGACTACATCATCCGGGAAGGCACCATTGGCAAGAAGATG
 F  E  V  F  Q  P  G  D  Y  I  I  R  E  G  T  I  G  K  K  M 1990      2000      2010      2020      2030      2040
            |         |         |         |         |         |
TACTTCATCCAGCATGGCGTGGTCAGCGTGCTCACCAAGGGCAACAAGGAGACCAAGCTG
 Y  F  I  Q  H  G  V  V  S  V  L  T  K  G  N  K  E  T  K  L
```

FIG. 15C

```
          2050        2060        2070        2080        2090        2100
            |           |           |           |           |           |
GCCGACGGCTCCTACTTTGGAGAGATCTGCCTGCTGACCCGGGGCCGGCGCACAGCCAGC

A   D   G   S   Y   F   G   E   I   C   L   L   T   R   G   R   R   T   A   S 2110        2120        2130        2140        2150        2160
            |           |           |           |           |           |
GTGAGGGCCGACACCTACTGCCGCCTCTACTCGCTGAGCGTGGACAACTTCAATGAGGTG

V   R   A   D   T   Y   C   R   L   Y   S   L   S   V   D   N   F   N   E   V 2170        2180        2190        2200        2210        2220
            |           |           |           |           |           |
CTGGAGGAGTACCCCATGATGCGAAGGGCCTTCGAGACCGTGGCGCTGGACCGCCTGGAC

L   E   E   Y   P   M   M   R   R   A   F   E   T   V   A   L   D   R   L   D 2230        2240        2250        2260        2270        2280
            |           |           |           |           |           |
CGCATTGGCAAGAAGAACTCCATCCTCCTCCACAAAGTCCAGCACGACCTCAACTCCGGC

R   I   G   K   K   N   S   I   L   L   H   K   V   Q   H   D   L   N   S   G 2290        2300        2310        2320        2330        2340
            |           |           |           |           |           Stop
GTCTTCAACTACCAGGAGCAGAAGCTGATCTCAGAGGAGGACCTGCTTTGAGCCTGATAT
                     Myc-Tag
  V   F   N   Y   Q   E   Q   K   L   I   S   E   E   D   L   -   A   -   Y

2350
            |
CTCTAGGGGATCCGCCCC

METHODS FOR TREATING CARDIAC PACING CONDITIONS

CROSS REFERENCE TO RELATED APPLICATIONS

This application claims the benefit of U.S. Provisional Application No. 61/351,836 filed Jun. 4, 2010 and cross reference is hereby made to the commonly assigned related U.S. application Ser. No. 13/096,164, entitled "Systems and Methods to Treat Cardiac Pacing Conditions" and U.S. application Ser. No. 13/096,193 entitled "Compositions to Treat Cardiac Pacing Conditions", filed concurrently herewith all of which are incorporated herein by reference in its their entirety.

BACKGROUND

Cardiac contraction in a healthy human heart is initiated by spontaneous excitation of the sinoatrial ("SA") node, which is located in the right atrium. The electric impulse generated by the SA node travels to the atrioventricular ("AV") node where it is transmitted to the bundle of His and to the Purkinje network. The fibers in the Purkinje network branch out in many directions to facilitate coordinated contraction of the left and right ventricles. In some disease states, the heart loses some of its natural capacity to pace properly. Such dysfunction is commonly treated by implanting a pacemaker.

While effectively improving the lives of many patients, implantable pacemakers have certain technical limitations. For example, implantable pacemakers rely on a self-contained power source such as a battery and consequently have a limited lifetime before the power source is in need of replacement. Implantable pacemakers also require pacing leads, which may fail and result in loss of therapy. Hence, an otherwise healthy patient may require multiple surgeries to replace the power source, leads, or the entire implantable pacemaker. Also, implantable pacemakers may not directly respond to physiological signals similar to the way the SA node responds to such signals.

Recently, biological methods of influencing a patient's cardiac cells have been developed, some of which include administering biopharmaceutical compositions that affect cardiac pacing. Developments in genetic engineering have produced methods for genetically modifying cardiac cells to modify non-pacemaking cardiac cells to pacemaker-like cardiac cells or regenerate the pacing capabilities of cells in the conduction system of the heart. For example, Johns and Marban (U.S. Pat. No. 6,214,620) describes a method for modulating the excitability of ventricular cells by controlling the regulation of the expression of certain ion channels (e.g. $K^+$ channels). Marban and Li (PCT Publication No. WO 02/087419) and Sigg et al. (PCT Publication No. WO 05/062890A3) describe methods and systems for modulating electrophysiological behavior of cardiac cells by genetic modification of inwardly rectifying $K^+$ channels ($I_{K1}$) in quiescent ventricular cells.

Another recent biological approach for modulating cardiac pacing involves implanting into the SA node or other suitable heart regions cells having particular ion channels that are commonly referred to as hyperpolarization-activated and cyclic nucleotide-gated (HCN) channels. For example, see Rosen and Robinson (PCT Publication No. WO 02/098286) and Sigg et al. (PCT Publication No. WO 05/062958A2). Physiologically originating in the SA node, the HCN channels play a prominent role in the control of rhythmic electrical heart activity. Cyclic nucleotides modulate the HCN channel activity, and channel activation occurs upon hyperpolarization rather than depolarization. There are four isoforms of HCN channels (HCN1-4), and each has greater or lesser prevalence in different heart regions. Because the HCN isoforms are directly involved in pacemaker current modulation and activation, implantation of HCN-expressing cells into cardiac tissue that is diseased or experiencing conduction blockage is a viable method for regulating cardiac pacemaker function.

SUMMARY OF THE INVENTION

The present invention provides methods for treating a cardiac pacing condition. The method may include administering to a subject in need thereof an effective amount of an HCN polynucleotide. The HCN polynucleotide includes a nucleotide sequence encoding an HCN polypeptide having channel activity. The amino acid sequence of the HCN polypeptide and the amino acid sequence of a reference polypeptide have at least 80% identity, where the reference polypeptide begins with an amino acid selected from amino acids 92-214 and ends with an amino acid selected from amino acids 723-1188 of SEQ ID NO:8. An example of a reference polypeptide is amino acids 214-723 of SEQ ID NO:8. The HCN polynucleotide may be DNA or RNA. The HCN polynucleotide may be present in a vector, such as a viral vector (including, for instance, a single strand adeno-associated virus or a self complementary adeno-associated virus), a transposon vector, or a plasmid vector.

The HCN polynucleotide administered to the subject may be present in a genetically modified cell, and the HCN polynucleotide may be integrated in the genomic DNA of the genetically modified cell, or may be present as part of an extra-chromosomal vector in the cell. The method may further include administering to the subject a second HCN polynucleotide.

The HCN polynucleotide may be administered by introduction of the HCN polynucleotide into cardiac atrium cells or cardiac ventricle cells. Various methods may be used to introduce the HCN polynucleotide, including, for instance, a syringe or a catheter.

The present invention also provides a composition that includes an HCN polynucleotide present in a vector. Preferably, the HCN polynucleotide includes a nucleotide sequence encoding an HCN polypeptide having channel activity, wherein the amino acid sequence of the HCN polypeptide and the amino acid sequence of a reference polypeptide have at least 80% identity, and where the reference polypeptide begins with an amino acid selected from amino acids 92-214 and ends with an amino acid selected from amino acids 723-1188 of SEQ ID NO:8. The composition may further include a pharmaceutically acceptable carrier. The vector may be a viral vector (including, for instance, a single strand adeno-associated virus or a self complementary adeno-associated virus), a transposon vector, or a plasmid vector.

Further provided by the invention is a genetically modified cell that includes an HCN polynucleotide. Preferably, the HCN polynucleotide includes a nucleotide sequence encoding an HCN polypeptide having channel activity, wherein the amino acid sequence of the HCN polypeptide and the amino acid sequence of a reference polypeptide have at least 80% identity, and where the reference polypeptide begins with an amino acid selected from amino acids 92-214 and ends with an amino acid selected from amino acids 723-1188 of SEQ ID NO:8. The HCN polynucleotide may be integrated in the genomic DNA of the genetically modified cell, or may be present as part of an extra-chromosomal vector in the cell.

The genetically modified cell may be part of a composition, and the composition may include a pharmaceutically acceptable carrier.

The present invention is also directed to methods that include identifying a distal end of a catheter at a tissue site of a patient and delivering a fluid or polymer that contains an HCN polynucleotide to the tissue site of the patient via the catheter. The identifying may include an electrically sensing contact between a distal end of a catheter and the tissue site of the patient.

The method may further include delivering an electrical stimulus to the cardiac tissue site of the patient to enhance transfer of the HCN polynucleotide to the tissue site via electroporation. The electrical stimulus may be delivered to the tissue site via the catheter, for instance, via an electrode coupled to the catheter and an electrode coupled to a distal tip of a probe extending from the catheter. An example of delivering the the electrical stimulus to the tissue site via the catheter may include delivering the electrical stimulus to the tissue site via an electrode coupled to the catheter and a distal tip of a probe extending from the catheter, the distal tip of the probe is formed from an electrically conductive material. The electrical stimulus may be delivered to the tissue site via an implanted medical device. The electrical stimulus delivered to the tissue site may include a stimulation pulse, or a series of stimulation pulses. The delivering fluid to the tissue site of the patient via the catheter may include delivering fluid to the tissue site of the patient via one or more exit ports of a distal tip of a probe extending from the catheter. The distal tip of the probe may include a needle or may be a helix shaped distal tip. The distal tip of the probe may extend from a body of the catheter upon sensing contact between the tissue site of the patient and the catheter.

Also provided by the present invention is a system that includes a fluid supply, a catheter, and a power supply to generate an electrical stimulus that is delivered to the tissue site. The system may include a pump to drive fluid from the fluid supply through the catheter, and/or the power supply may include an implanted medical device that delivers the electrical stimulus to the tissue site. The implanted medical device may include one of an implantable pulse generator, an implantable cardioverter/defibrillator, and an implantable pacemaker/cardioverter/defibrillator. The fluid supply may include an implanted fluid reservoir. The power supply may be coupled to the catheter, and the catheter may deliver the electrical stimulus to the tissue site.

The catheter of the system may include a catheter body that defines an inner lumen, a probe within the inner lumen that delivers fluid from the fluid supply to a tissue site of a patient, and at least one electrode coupled to the catheter to detect contact between the catheter and the tissue site, wherein the fluid comprises an HCN polynucleotide described herein. The probe may include a distal tip made from an electrically conductive material, and the electrode may be coupled to the catheter body, where the catheter delivers the electrical stimulus to the tissue site via the electrode coupled to the catheter body and the distal tip of the probe. The catheter may include a pair of electrodes, a first electrode coupled to the probe and a second electrode coupled to the catheter body, where the catheter delivers the electrical stimulus to the tissue site via the electrode coupled to the catheter body and the electrode coupled to the probe. The electrical stimulus delivered to the tissue site may include a stimulation pulse or a series of stimulation pulses. The fluid may include a polymer.

As used herein, an "isolated" substance is one that has been removed from its natural environment, produced using recombinant techniques, or chemically or enzymatically synthesized. For instance, a polypeptide, a polynucleotide, or a cell can be isolated. Preferably, a substance is purified, i.e., is at least 60% free, preferably at least 75% free, and most preferably at least 90% free from other components with which they are naturally associated.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region" and "coding sequence" are used interchangeably and refer to a nucleotide sequence that encodes a polypeptide and, when placed under the control of appropriate regulatory sequences, expresses the encoded polypeptide. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner A regulatory sequence is "operably linked" to a coding region when it is joined in such a way that expression of the coding region is achieved under conditions compatible with the regulatory sequence.

A polynucleotide that includes a coding region may include heterologous nucleotides that flank one or both sides of the coding region. As used herein, "heterologous nucleotides" refer to nucleotides that are not normally present flanking a coding region that is present in a wild-type cell. For instance, a coding region present in a wild-type cell and encoding an HCN polypeptide is flanked by homologous sequences, and any other nucleotide sequence flanking the coding region is considered to be heterologous. Examples of heterologous nucleotides include, but are not limited to regulatory sequences. Typically, heterologous nucleotides are present in a polynucleotide of the present invention through the use of standard genetic and/or recombinant methodologies well known to one skilled in the art. A polynucleotide of the present invention may be included in a suitable vector.

As used herein, an "exogenous polynucleotide" refers to a polynucleotide that has been introduced into a cell by artificial means. As used herein, the term "endogenous polynucleotide" refers to a polynucleotide that is normally or naturally found in a cell. An "endogenous polynucleotide" is also referred to as a "native polynucleotide."

The terms "complement" and "complementary" as used herein, refer to the ability of two single stranded polynucleotides to base pair with each other, where an adenine on one strand of a polynucleotide will base pair to a thymine or uracil on a strand of a second polynucleotide, and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary. The term "substantial complement" and cognates thereof as used herein, refer to a polynucleotide that is capable of selectively hybridizing to a specified polynucleotide under stringent hybridization conditions. Stringent hybridization can take place under a number of pH, salt and temperature conditions. The pH can vary from 6 to 9, preferably 6.8 to 8.5. The salt concentration can vary from 0.15 M sodium to 0.9 M sodium, and other cations can be used as long as the ionic strength is equivalent to that specified for sodium. The temperature of the hybridization reaction can vary from 30° C. to 80° C., preferably from 45° C. to 70° C. Additionally, other compounds can be added to a hybridization reaction to promote specific hybridization at lower temperatures, such as at or approaching room temperature. Among the compounds contemplated for lowering the temperature requirements is formamide. Thus, a polynucleotide is typically substantially complementary to a second polynucleotide if hybridization occurs between the polynucleotide and the second polynucleotide. As used herein, "specific hybridization" refers to hybridization between two polynucleotides under stringent hybridization conditions.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, enzyme, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

As used herein, "identity" refers to sequence similarity between two polypeptides or two polynucleotides. The sequence similarity between two polypeptides is determined by aligning the residues of the two polypeptides (e.g., a candidate amino acid sequence and a reference amino acid sequence, such as SEQ ID NO:2, 4, 6, or 8, or a portion thereof) to optimize the number of identical amino acids along the lengths of their sequences; gaps in either or both sequences are permitted in making the alignment in order to optimize the number of shared amino acids, although the amino acids in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as the BESTFIT algorithm in the GCG package (Madison, Wis.), or the Blastp program of the BLAST 2 search algorithm, as described by Tatusova, et al. (*FEMS Microbiol Lett* 1999, 174:247-250), and available through the World Wide Web, for instance at the internet site maintained by the National Center for Biotechnology Information, National Institutes of Health. Preferably, sequence similarity between two amino acid sequences is determined using the Blastp program of the BLAST 2 search algorithm. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, structural similarity is referred to as "identities."

The sequence similarity between two polynucleotides is determined by aligning the residues of the two polynucleotides (e.g., a candidate nucleotide sequence and a reference nucleotide sequence, such as SEQ ID NO:1, 3, 5, 7, or a portion thereof) to optimize the number of identical nucleotides along the lengths of their sequences; gaps in either or both sequences are permitted in making the alignment in order to optimize the number of shared nucleotides, although the nucleotides in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as GCG FastA (Genetics Computer Group, Madison, Wis.), MacVector 4.5 (Kodak/IBI software package) or other suitable sequencing programs or methods known in the art. Preferably, sequence similarity between two nucleotide sequences is determined using the Blastn program of the BLAST 2 search algorithm, as described by Tatusova, et al. (1999, *FEMS Microbiol Leu.*, 174:247-250), and available through the World Wide Web, for instance at the internet site maintained by the National Center for Biotechnology Information, National Institutes of Health. Preferably, the default values for all BLAST 2 search parameters are used, including reward for match=1, penalty for mismatch=−2, open gap penalty=5, extension gap penalty=2, gap x_dropoff=50, expect=10, wordsize=11, and optionally, filter on. In the comparison of two nucleotide sequences using the BLAST search algorithm, sequence similarity is referred to as "identities."

Conditions that "allow" an event to occur or conditions that are "suitable" for an event to occur, such as an enzymatic reaction, or "suitable" conditions are conditions that do not prevent such events from occurring. Thus, these conditions permit, enhance, facilitate, and/or are conducive to the event.

As used herein, "genetically modified cell" refers to a cell into which has been introduced an exogenous polynucleotide, e.g., an expression vector. For example, a cell is a genetically modified cell by virtue of introduction into a suitable cell of an exogenous polynucleotide that is foreign to the cell, or an exogenous polynucleotide that encodes a polypeptide that is normally present in the cell. "Genetically modified cell" also refers to a cell that has been genetically manipulated such that endogenous nucleotides have been altered. For example, a cell is a genetically modified cell by virtue of introduction into a suitable cell of an alteration of endogenous nucleotides. For instance, an endogenous coding region could be mutagenized. Such mutations may result in a polypeptide having a different amino acid sequence than was encoded by the endogenous polynucleotide. Another example of a genetically modified cell is one having an altered regulatory sequence, such as a promoter, to result in increased or decreased expression of an operably linked endogenous coding region.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 1, 1A and 1B. Multiple sequence alignment of a human HCN1 (SEQ ID NO:2), a human HCN2 (SEQ ID NO:4), a human HCN3 (SEQ ID NO:6), and a human HCN4 (SEQ ID NO:8). The six α-helical segments (S1-S6), the pore helix (PoreH), the selectivity filter (SF), and the cyclic-nucleotide binding domain (CNBD) are depicted.

FIGS. 2, 2A, 2B, 2C and 2D. Nucleotide sequence encoding a human HCN1 (SEQ ID NO:1), a human HCN2 (SEQ ID NO:3), a human HCN3 (SEQ ID NO:5), and a human HCN4 (SEQ ID NO:7), and the corresponding amino acid sequences of the HCN1 (SEQ ID NO:2), the HCN2 (SEQ ID NO:4), the HCN3 (SEQ ID NO:6), and the HCN4 (SEQ ID NO:8) polypeptides.

FIG. 6. Three different super-truncated versions of HCN4 (HCN4st) in comparison with HCN4wt and HCN4t.

FIGS. 15, 15A, 15B, 15C and 15D. Nucleotide sequence (SEQ ID NO:30) and corresponding amino acid sequence (SEQ ID NO: 31) of HCN4 with MyC fusion.

DETAILED DESCRIPTION OF ILLUSTRATIVE EMBODIMENTS

Polypeptides

Figure 3:
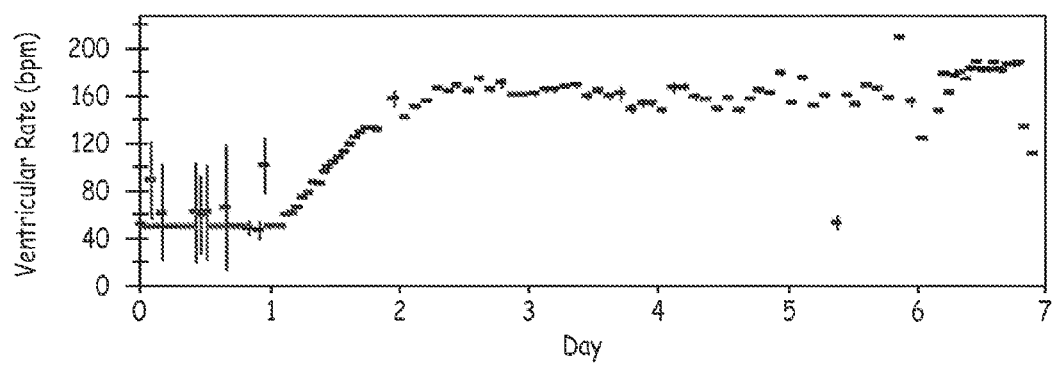
FIG. 3. Biological pacemaker from AV node ablated canine injected with the hHCN4t coding region carried by adenovirus vector. A significant increase in ventricular heart rate was observed following Adv-hHCN4t administration. Biological pacemaker reached a peak on day 2 and maintained a rate at peak level through termination at one week.

The present invention includes isolated polypeptides having hyperpolarization-activated and cyclic nucleotide-gated channel activity, also referred to herein as channel activity. A polypeptide having channel activity is referred to herein as an HCN polypeptide. An HCN polypeptide includes at least three domains, the transmembrane core, the cytosolic N-terminal domain, and the cytosolic C-terminal domain (Wahl-Schott and Biel, 2009, Coll. Mol. Life Sci., 66:470-494). The transmembrane core includes six α-helical segments (S1-S6) and an ion conducting pore loop between S5 and S6 (see FIG. 6). A highly conserved asparagine residue is typically present in the extracellular loop between S5 and the pore loop (Much et al., 2003, J. Biol. Chem. 278:43781-43786). The pore loop typically includes a glycine-tyrosine-glycine (GYG) motif The voltage sensor of HCN polypeptides is formed by a charged S4-helix carrying a series of arginine or lysine residues regularly spaced at every third position (Vaca et al., 2000, FEBS Lett., 479:35-40), optionally including a serine residue (Chen et al., 2000, J. Biol. Chem., 275:36465-36471). There is evidence suggesting that the loop connecting the S4 with the S5 segment plays a role in conferring the differential response to voltage (Long et al., 2005, Science, 309:903-908, Decher et al., 2004, J. Biol. Chem., 279:13859-13865, and Prole et al., 2006, J. Gen. Physiol. 128:273-282). The proximal portion of the cytosolic C-terminus mediates the sensitivity of HCN polypeptides to cAMP (Zagotta et al., 2003, Nature, 425:200-205). This part of an HCN polypeptide includes a cyclic nucleotide-binding domain of about 120 amino acids (CNBD) and an 80 amino acid long linker region that connects the CNBD with the S6 segment.

Examples of HCN polypeptides useful in the methods described herein are depicted at SEQ ID NO:2, SEQ ID NO:4, SEQ ID NO:6, and SEQ ID NO:8. In some embodiments an HCN polypeptide useful in the methods disclosed herein is truncated at the amino terminal end. Typically, such a truncation may result in the deletion of amino acids up to, but not including, amino acids corresponding to the S1 α-helical segment. For instance, with reference to the HCN polypeptide depicted at SEQ ID NO:8, the truncation may be from amino acid 1 to amino acid 258, 257, 256, 255, 254, 253, 252, 251, 250, 249, 248, 247, 246, 245, 244, 243, 242, 241, 240, 239, 238, 237, 236, 235, 234, 233, 232, 231, 230, 229, 228, 227, 226, 225, 224, 223, 222, 221, 220, 219, 218, 217, 216, 215, 214, 213, 212, 211, or 210, and so on up to the second amino acid of SEQ ID NO:8. In some embodiments an HCN polypeptide is truncated at the carboxy terminal end. Typically, such a truncation may result in the deletion of amino acids from the carboxy terminal end up to the amino acids that make up the CNBD domain. For instance, with reference to the HCN polypeptide depicted at SEQ ID NO:8, the truncation may begin at amino acid 723 (i.e., amino acids 723 to the last amino acid, 1203, are not present), 724, 725, 726, 727, 728, 729, 730, 731, 732, 733, 734, 735, 736, 737, 738, 739, or 741, and so on up to amino acid 1202 of SEQ ID NO:8.

In some embodiments, an HCN polypeptide useful in the methods described herein includes a truncation at both the amino terminal and carboxy terminal ends. Accordingly, an HCN polypeptide of the present invention may include an amino acid sequence corresponding to a core region selected from the amino acid sequence of SEQ ID NO:2, SEQ ID NO:4, SEQ ID NO:6, or SEQ ID NO:8. The core region may be, for instance, amino acids 139-603 of SEQ ID NO:2, 208-672 of SEQ ID NO:4, 80-545 of SEQ ID NO:6, or 214-723 of SEQ ID NO:8, and may optionally include additional amino acids located on the amino terminal end and/or the carboxy terminal end. Such additional amino acids may be selected from the corresponding regions of SEQ ID NO:2, SEQ ID NO:4, SEQ ID NO:6, or SEQ ID NO:8, or may be other amino acid sequences as discussed herein. For instance, in one aspect an HCN polypeptide may have an amino acid sequence beginning with an amino acid selected from amino acids 92-214 of SEQ ID NO:8 and ending with an amino acid selected from amino acids 723-1188 of SEQ ID NO:8. Specific examples of HCN polypeptides include, but are not limited to, a core region from SEQ ID NO:8 beginning at amino acid 213, 214, 221, or 226, and ending at amino acid 723, 738, or 753.

Other examples of HCN polypeptides include those having sequence similarity with a region selected from the amino acid sequence of SEQ ID NO:2, SEQ ID NO:4, SEQ ID NO:6, or SEQ ID NO:8. An HCN polypeptide having sequence similarity with the region selected from the amino acid sequence of SEQ ID NO:2, SEQ ID NO:4, SEQ ID NO:6, or SEQ ID NO:8 has channel activity. An HCN polypeptide may be isolated from a eukaryotic cell, such as a vertebrate cell or an invertebrate cell. Examples of suitable vertebrate cells include, but are not limited to, cells obtained from members of the Family Canidae (such as dogs), members of the Family Suidae (such as pigs), members of the Family Muridae (such as rats and mice), members of the genus *Ovis* (such as sheep), non-human primates, and human cells. An HCN polypeptide may be produced using recombinant techniques, or chemically or enzymatically synthesized using routine methods.

HCN polypeptides form channels that are unique among vertebrate voltage-gated ion channels: they have a reverse voltage dependence that leads to activation upon hyperpolarization. In addition, voltage-dependent opening of these channels is directly regulated by the binding of cAMP. HCN polypeptides activate upon hyperpolarization with a characteristic sigmoidal time course. An HCN polypeptide having channel activity will display a reverse voltage dependence that leads to activation upon hyperpolarization under suitable conditions. Suitable conditions typically include the expression of an HCN polypeptide in a cell such that it can form channels, and then assaying for activation upon hyperpolarization. Suitable assays include whole cell patch clamp analysis and microelectrode array. Preferably, whole cell patch clamp analysis is used. Methods for whole cell patch clamp analysis are known and routine in the art (Hamill, 1981, Pflugers Arch., 391(2):85-100). An example of a whole cell patch clamp assay is described in Example 1. A polypeptide that leads to functional HCN4 current under suitable conditions is considered to have channel activity and to be an HCN polypeptide, while a polypeptide that does not lead to functional HCN4 current under suitable conditions is considered to not have channel activity and is not an HCN polypeptide.

The amino acid sequence of an HCN polypeptide having sequence similarity to a region of SEQ ID NO:2, SEQ ID NO:4, SEQ ID NO:6, or SEQ ID NO:8 may include conservative substitutions. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) may generally be substituted for another amino acid without substantially altering the secondary and/or tertiary structure of a polypeptide. For the purposes of this invention, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, but also include artificial amino acids, such as beta or gamma amino acids and those containing non-natural side chains, and/or other similar monomers such as hydroxyacids. SEQ ID NOs:2, 4, 6, and 8 are shown in FIG. 1 in a multiple protein alignment. Identical and conserved amino acids are marked. Also depicted are those regions corresponding to the six α-helical segments, the PoreH, the SF, and the CNBD domains. This information, and other information regarding conserved regions of HCN polypeptides described herein, permit the skilled person to predict whether alterations to the amino acid sequence of SEQ ID NO:2, SEQ ID NO:4, SEQ ID NO:6, or SEQ ID NO:8 are likely to result in an HCN polypeptide having channel activity.

Guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a polypeptide sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

In some aspects an HCN polypeptide may include specific mutations in the region linking the S3 and S4 segments (e.g., amino acids 360-367 of SEQ ID NO:8). Such mutations are depicted in Table 1 (see Sigg et al., U.S. Patent Application Publication 2009/0099611.

TABLE 1

| SEQ ID NO: | Mutant | S3-S4 linker (amino acids 360-368) |
|---|---|---|
| 9 | Wild-type HCN4 | ETRIDSEVY |
| 10 | T360A | EARIDSEVY |
| 11 | Δ363-367 | ETRI |
| 12 | T360A, Δ363-367 | EARI |
| 13 | TRI360-362AGM | EAGMDSEVY |
| 14 | TRI360-362KGM | EKGMDSEVY |
| 15 | T360A, I362M | EARMDSEVY |
| 16 | T360A, Δ365-367 | EARIDS |
| 17 | E365G | ETRIDSGVY |
| 18 | E365A | ETRIDSAVY |
| 19 | R361G | ETGIDSEVY |
| 20 | TR360-361AA | EAAIDSEVY |
| 21 | I362C | ETRCDSEVY |
| 22 | I362S | ETRSDSEVY |
| 23 | I362T | ETRTDSEVY |
| 24 | TRI360-362AGM, Δ363-367 | EAGM |

An HCN polypeptide may be expressed as a fusion polypeptide that includes an HCN polypeptide and an additional amino acid sequence. For instance, the additional amino acid sequence may be useful for purification of the fusion polypeptide by affinity chromatography. Various methods are available for the addition of such affinity purification moieties to proteins. Examples of affinity tags include a polyhistidine-tag and a MyC-tag (see, for instance, Hopp et al. (U.S. Pat. No. 4,703,004), Hopp et al. (U.S. Pat. No. 4,782,137), Sgarlato (U.S. Pat. No. 5,935,824), and Sharma Sgarlato (U.S. Pat. No. 5,594,115)). In another example, the additional amino acid sequence may be useful for tagging the fusion polypeptide to aid in identification of the polypeptide in various conditions, including in a tissue or in a cell.

Polynucleotides

The present invention also includes isolated polynucleotides encoding an HCN polypeptide described herein. A polynucleotide encoding a polypeptide having channel activity is referred to herein as an HCN polynucleotide. HCN polynucleotides may have a nucleotide sequence encoding a polypeptide having the amino acid sequence shown in SEQ ID NO:2, SEQ ID NO:4, SEQ ID NO:6, or SEQ ID NO:8, or region of one of those amino acid sequences, as described herein. An example of the class of nucleotide sequences encoding a region of a polypeptide disclosed at SEQ ID NO:2, 4, 6, or 8 is the corresponding region of SEQ ID NO:1, 3, 5, or 7, respectively. It should be understood that a polynucleotide encoding an HCN polypeptide represented by, for instance, SEQ ID NO:8, or a portion thereof, is not limited to the nucleotide sequence disclosed at SEQ ID NO:7, but also includes the class of polynucleotides encoding such polypeptides as a result of the degeneracy of the genetic code. For example, the naturally occurring nucleotide sequence SEQ ID NO:7 is but one member of the class of nucleotide sequences encoding a polypeptide having the amino acid sequence SEQ ID NO:8. The class of nucleotide sequences encoding a selected polypeptide sequence is large but finite, and the nucleotide sequence of each member of the class may be readily determined by one skilled in the art by reference to the standard genetic code, wherein different nucleotide triplets (codons) are known to encode the same amino acid. It should be understood that any nucleotide sequence taught herein also includes the complement thereof, and the corresponding RNA sequences.

An HCN polynucleotide of the present invention may have sequence similarity with the nucleotide sequence of SEQ ID NO:1, 3, 5, or 7. HCN polynucleotides having sequence similarity with the nucleotide sequence of SEQ ID NO:3 encode an HCN polypeptide. An HCN polynucleotide may be isolated from a vertebrate cell or an invertebrate cell, or may be produced using recombinant techniques, or chemically or enzymatically synthesized. An HCN polynucleotide may further include heterologous nucleotides flanking the open reading frame encoding the HCN polypeptide. Typically, heterologous nucleotides may be at the 5' end of the coding region, at the 3' end of the coding region, or the combination thereof The number of heterologous nucleotides may be, for instance, at least 10, at least 100, or at least 1000.

HCN polynucleotides may be obtained from a eukaryotic cell, such as a vertebrate cell or an invertebrate cell. Examples of suitable vertebrate cells include, but are not limited to, cells obtained from members of the Family Canidae, and human cells. HCN polynucleotides may be produced in vitro or in vivo. For instance, methods for in vitro synthesis include, but are not limited to, chemical synthesis with a conventional DNA/RNA synthesizer. Commercial suppliers of synthetic polynucleotides and reagents for such synthesis are well known.

An HCN polynucleotide may be present in a vector. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, Molecular Cloning: A Laboratory Manual, Cold Spring Harbor Laboratory Press (1989). A vector may provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, and artificial chromosome vectors. In some aspects preferred vectors include those useful for gene therapy, e.g., vectors that can be administered to a subject to result in transient or sustained expression of a coding region to result in a beneficial polypeptide. A large variety of such vectors are known in the art and are readily available. Examples of vectors useful in gene therapy include isolated nucleic acid, e.g., plasmid-based vectors which may be extrachromosomally maintained, including minicircle vectors; viral vectors, e.g., recombinant adenovirus, retrovirus, lentivirus, herpesvirus, poxvirus, papilloma virus, or adeno-associated virus; and transposons, e.g., recombinant transposons such as Sleeping Beauty and piggyBac. Preferred examples of vectors include single strand adeno-associated virus (ssAAV) and self complementary AAV (scAAV), a modified adeno-associated virus that bypasses the required second-strand DNA synthesis to achieve transcription of the coding region (McCarty, 2008, Mol Ther., 16:1648-1656).

Useful ssAAV vectors and scAAV vectors are commercially available from, for instance, Virovek, Hayward, Calif.

Selection of a vector depends upon a variety of desired characteristics in the resulting construct, such as a selection marker, vector replication rate, and the like. In some aspects, suitable host cells for cloning or expressing the vectors herein include eukaryotic cells. Suitable eukaryotic cells include fungi and mammalian cells. In other aspects, suitable host cells for cloning or expressing the vectors herein include prokaryotic cells. Suitable prokaryotic cells include eubacteria, such as gram-negative microbes, for example, E. coli. Vectors may be introduced into a host cell using methods that are known and used routinely by the skilled person. For example, calcium phosphate precipitation, electroporation, heat shock, lipofection, microinjection, and viral-mediated nucleic acid transfer are common methods for introducing nucleic acids into host cells.

An expression vector optionally includes regulatory sequences operably linked to the coding region. An example of a regulatory sequence includes a promoter. The invention is not limited by the use of any particular promoter, and a wide variety of promoters are known. Promoters act as regulatory signals that bind RNA polymerase in a cell to initiate transcription of a downstream (3' direction) coding region. The promoter used may be a constitutive or an inducible promoter. It may be, but need not be, heterologous with respect to the host cell.

In some aspects, tissue-specific promoters may be used. Tissue-specific expression may enhance the safety of a therapy described herein as expression in non-target tissue becomes less likely. For example, cardiac tissue specific promoters allow cardiac myocyte specific expression of the coding region of interest (including expression in stem cells with cardiac phenotype). Examples of cardiac tissue specific promoters include, but are not limited to, promoters from the following coding regions: an α-myosin heavy chain coding region, e.g., a ventricular α-myosin heavy chain coding region, β-myosin heavy chain coding region, e.g., a ventricular β-myosin heavy chain coding region, myosin light chain 2v coding region, e.g., a ventricular myosin light chain 2 coding region, myosin light chain 2a coding region, e.g., a ventricular myosin light chain 2 coding region, cardiomyocyte-restricted cardiac ankyrin repeat protein (CARP) coding region, cardiac α-actin coding region, cardiac m2 muscarinic acetylcholine coding region, ANP coding region, BNP coding region, cardiac troponin C coding region, cardiac troponin I coding region, cardiac troponin T coding region, cardiac sarcoplasmic reticulum Ca-ATPase coding region, and skeletal α-actin coding region. Further, chamber-specific promoters or enhancers may also be employed, e.g., for atrial-specific expression, the quail slow myosin chain type 3 (MyHC3) or ANP promoter may be used. Examples of ventricular myocyte-specific promoters include a ventricular myosin light chain 2 promoter and a ventricular myosin heavy chain promoter.

Other useful promoters, for example, would be sensitive to electrical stimulus that could be provided from, for example, an implantable device. Electrical stimulation can promote gene expression (Padua et al., U.S. Patent Application No. 2003/0204206 A1).

Other regulatory regions include drug-sensitive elements (e.g., a drug-inducible suppressor or promoter). Drug-responsive promoters may induce or suppress expression of an operably linked coding region. For example, a tetracycline responsive element (TRE) that binds doxycycline may present within a promoter construct. When doxycycline is removed, transcripton from the TRE is turned off in a dose-dependent manner. Examples of inducible drug-responsive promoters are the ecdysone-inducible promoter (Johns and Marban, U.S. Pat. No. 6,214,620) and rapamycin-dependent expression (Clackson et al., U.S. Pat. No. 6,506,379, see also Discher et al., 1998, J. Biol. Chem., 273:26087-26093; Prentice et al., 1997, Cardiovascular Res., 35: 567-576).

Further examples of regulatory regions include enhancers, such as cardiac enhancers, to increase the expression of an operably linked coding region in cardiac tissue, such as regions of the cardiac conduction system. Such enhancer elements may include the cardiac specific enhancer elements derived from Csx/Nkx2.5 regulatory regions (Lee and Izumo, U.S. Patent Application 2002/0022259) or the cGATA-6 enhancer.

An expression vector may optionally include a ribosome binding site and a start site (e.g., the codon ATG) to initiate translation of the transcribed message to produce the polypeptide. It may also include a termination sequence to end translation. A termination sequence is typically a codon for which there exists no corresponding aminoacetyl-tRNA, thus ending polypeptide synthesis. The polynucleotide used to transform the host cell may optionally further include a transcription termination sequence.

A vector introduced into a host cell optionally includes one or more marker sequences, which typically encode a molecule that inactivates or otherwise detects or is detected by a compound in the growth medium. For example, the inclusion of a marker sequence may render the transformed cell resistant to an antibiotic, or it may confer compound-specific metabolism on the transformed cell. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, PCT Publication Nos. WO 92/08796 and WO 94/28143). Such marker genes can provide an added measure of control that can be advantageous in gene therapy contexts.

Polypeptides useful in the present invention may be produced using recombinant DNA techniques, such as an expression vector present in a cell. Such methods are routine and known in the art. The polypeptides may also be synthesized in vitro, e.g., by solid phase peptide synthetic methods. The solid phase peptide synthetic methods are routine and known in the art. A polypeptide produced using recombinant techniques or by solid phase peptide synthetic methods may be further purified by routine methods, such as fractionation on immunoaffinity or ion-exchange columns, ethanol precipitation, reverse phase HPLC, chromatography on silica or on an anion-exchange resin such as DEAE, chromatofocusing, SDS-PAGE, ammonium sulfate precipitation, gel filtration using, for example, Sephadex G-75, or ligand affinity.

The present invention also includes genetically modified cells that have an HCN polynucleotide encoding an HCN polypeptide. Compared to a control cell that is not genetically modified according to the present invention, a genetically modified cell may exhibit production of an HCN polypeptide. A polynucleotide encoding an HCN polypeptide may be present in the cell as an extrachromosomal vector or integrated into a chromosome. Examples of cells include, but are not limited to, excitable cells, such as cardiomyocytes and HL-5 cells; and non-excitable cells, such as stem cells, fibroblasts, mesenchymal cells, and HEK293 cells. In some aspects the cells may also be modified to express connexions or gap junctions. The coding regions encoding connexion polypeptides are readily available to the skilled person.

A genetically modified cell may be ex vivo or in vivo. "Ex vivo" refers to a cell that has been removed from the body of an animal. Ex vivo cells include, for instance, primary cells (e.g., cells that have recently been removed from a animal and are capable of limited growth in tissue culture medium), and cultured cells (e.g., cells that are capable of long term culture in tissue culture medium). "In vivo" refers to cells that are present within the body of an animal.

Compositions

The present invention is also directed to compositions including an HCN polynucleotide, HCN polypeptide, or genetically modified cell. Such compositions typically include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration. Additional active compounds can also be incorporated into the compositions.

A composition may be prepared by methods well known in the art of pharmacy. In general, a composition can be formulated to be compatible with its intended route of administration. Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in ampoules, disposable syringes or multiple dose vials made of glass or plastic.

Compositions can include sterile aqueous solutions or dispersions and sterile powders for the extemporaneous preparation of sterile solutions or dispersions. For intravenous administration, suitable carriers include physiological saline, bacteriostatic water, Cremophor EL™ (BASF, Parsippany, N.J.) or phosphate buffered saline. A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (e.g., an HCN polynucleotide, or, in some aspects, an HCN polypeptide or genetically modified cell) in the required amount in an appropriate solvent with one or a combination of ingredients enumerated above, as required, followed by filtered sterilization. Generally, dispersions are prepared by incorporating the active compound into a sterile vehicle, which contains a dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

An active compound may be administered by any route including, but not limited to, intramuscular, buccal, rectal, intravenous or intracoronary administration, and transfer to cells may be enhanced using electroporation and/or iontophoresis. Administration may be systemic or local. In some aspects local administration may have advantages for site-specific, targeted disease management. Local therapies may provide high, clinically effective concentrations directly to the treatment site, without causing systemic side effects. Examples of locations to which an active compound can be targeted include, but are not limited to, the right or left atrium, including the sinoatrial node, the right or left ventricle, including the atrioventricular node. For instance, endocardial or myocardial cells of an atrium or a ventricle may be targeted. In some aspects, an HCN polynucleotide can be implanted in, or downstream from, the conduction pathway, in a heart region that is experiencing or may experience poor conduction. For example, if cardiac contraction is not being properly initiated by the SA node but the AV node conduction is intact, an HCN polynucleotide may be implanted in the myocardium of the SA node or the right atrium to cause the targeted region to depolarize and create electric impulses that will travel to the AV node. Alternatively, if cardiac contraction is not being properly conducted by the AV node then an HCN polynucleotide may be implanted downstream in the conduction pathway from the right atrium, i.e. in the bundle of His, the Purkinje network, or one of the ventricles. Other delivery sites include, but are not limited to, left ventricular epicardium.

Examples of routes of administration include the use of a delivery tool, such as a syringe for direct injection into cardiac tissue (for instance, during open heart surgery) or by catheter. For instance, one type of catheter useful in the methods described herein has electric sensing capabilities, which permits introduction of an active compound directly into the targeted cardiac tissue. The delivery tool may include electrodes for sensing electric activity and delivering pacing stimuli in order to determine the desired location for the biological pacemakers. Once the location is determined, an active compound is delivered to the cardiac tissue. The delivery tool may include an injection device that injects the active compound into cardiac tissue. One suitable method for injecting a genetic construct directly into the myocardium is described by Guzman et al., 1993, Circ. Res., 73:1202-1207. Furthermore, a delivery system for delivering genetic material to a targeted heart region is described in Laske et al. (U.S. Pat. No. 7,103,418) and Stokes et al. (PCT Publication No. WO 98/02150). Systems for myocardial, endocardial, subepicardial and epicardial delivery are described in Sullivan and Hezi-Yamit (U.S. Published Patent Application 20100137976), Hiniduma-Lokuge et al. (PCT Publication No. WO/2008/055001), and Sommer et al., (U.S. Pat. No. 7,274,966 and U.S. Pat. No. 7,187,971). Alternatively, genetically engineered cells may be cultured and proliferated on a solid scaffold, and then surgically delivered to the selected heart region together with the scaffold. The scaffold may also be directly injected into cardiac tissue.

Perfusion protocols that are useful are often sufficiently capable of delivering a genetic construct to at least about 10% of cardiac myocytes. Infusion volumes of between 0.01 ml and 3 ml are useful for direct intramyocardial injection. Also, suitable methods for targeting non-viral vector genetic constructs to the heart are described in Lawrence (U.S. Pat. No. 6,376,471).

When a polynucleotide is introduced into cardiac cells using any suitable technique, the polynucleotide is delivered into the cells by, for example, transfection or transduction procedures. Transfection and transduction refer to the acquisition by a cell of new genetic material by incorporation of added polynucleotides. Transfection can occur by physical or chemical methods. Many transfection techniques are known to those of ordinary skill in the art including, without limitation, calcium phosphate DNA co-precipitation, DEAE-dextrin DNA transfection, electroporation, naked plasmid adsorption, and cationic liposome-mediated transfection (commonly known as lipofection). Transduction refers to the process of transferring nucleic acid into a cell using a DNA or RNA virus.

A polynucleotide described herein may be used in combination with other agents assisting the cellular uptake of polynucleotides, or assisting the release of polynucleotides from endosomes or intracellular compartments into the cytoplasm or cell nuclei by, for instance, conjugation of those to the polynucleotide. The agents may be, but are not limited to, peptides, especially cell-penetrating peptides, protein transduction domains, and/or dsRNA-binding domains which enhance the cellular uptake of polynucleotides (Dowdy et al., US Published Patent Application 2009/0093026, Eguchi et al., 2009, *Nature Biotechnology* 27:567-571, Lindsay et al., 2002, Curr. Opin. Pharmacol., 2:587-594, Wadia and Dowdy, 2002, Curr. Opin. Biotechnol. 13:52-56. Gait, 2003, Cell. Mol. Life Sci., 60:1-10). The conjugations can be performed at an internal position at the oligonucleotide or at a terminal positions either the 5'-end or the 3'-end.

A polynucleotide described herein may be present in liposomes, including neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes or polyethyleneimine (PEI). An active compound may be present in a polymer matrix, for instance, a polymer matrix may be formed of any physiologically compatible material which generally retains a polynucleotide (which is a charged molecule) or optionally other agents including other agents under physiological conditions for a sustained period of time. The polymer matrix may extrude (release) the polynucleotide in response to an external stimulus, such as an electric field created by an electrical signal, or the matrix may provide for passive delivery.

Toxicity and therapeutic efficacy of such active compounds can be determined by standard pharmaceutical procedures in cell cultures or experimental animals, e.g., for determining the $ED_{50}$ (the dose therapeutically effective in 50% of the population). The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For a compound used in the methods of the invention, the therapeutically effective dose can be estimated initially from cell culture assays. In those aspects where a viral vector is used, such as an AAV-based vector, a dosage may be at least $10^9$, $10^{10}$, $10^{11}$, $10^{12}$, $10^{13}$, or $10^{14}$ viral particles.

Administration of an HCN polynucleotide, an HCN polypeptide, or a genetically modified cell described herein may be continuous or intermittent, depending, for example, upon the recipient's physiological condition, whether the purpose of the administration is therapeutic or prophylactic, and other factors known to a person skilled in the art. The administration may be essentially continuous over a preselected period of time or may be in a series of spaced doses.

Methods of Use

The present invention also includes methods of using the HCN polynucleotides, HCN polypeptides, and genetically modified cells described herein. The methods include, for instance, methods of treating a cardiac pacing condition. Examples of cardiac pacing conditions include, but are not limited to, patients with atrioventricular (AV) node dysfunction and/or sinoatrial (SA) node dysfunction. Such patients may have bradyarrhythmia, such as those with the clinical syndrome sick sinus syndrome. Cardiac pacing conditions may also occur in patients undergoing surgery (such as coronary artery bypass surgery or insertion of an artificial heart valve), or having endocarditis. Signs and symptoms associated with cardiac pacing conditions and the evaluation of such signs and symptoms are routine and known in the art. As used herein, the term "symptom" refers to subjective evidence of a cardiac pacing condition experienced by a subject. As used herein, the term "clinical sign" or, simply, "sign" refers to objective evidence of a cardiac pacing condition.

Treatment may be prophylactic or, alternatively, may be initiated after a cardiac pacing condition is evident. Treatment that is prophylactic, for instance, initiated before an animal manifests symptoms of a cardiac pacing condition, is referred to herein as treatment of a patient that is "at risk" of developing a cardiac pacing condition. Treatment initiated after development of symptoms of a cardiac pacing condition may result in decreasing the severity of the symptoms, or completely removing the symptoms. An "effective amount" is an amount effective to prevent the manifestation of symptoms of a cardiac pacing condition, decrease the severity of the symptoms of cardiac pacing condition, and/or completely remove the symptoms. It is not required that any composition of the present invention completely remove or cure all symptoms of a cardiac pacing condition.

Treatment may result in increasing the intrinsic pacing rate of cardiac cells, preferably to the normal physiological range for the subject. In some aspects, the intrinsic pacing rate is increased to 60-80 beats per minute (bpm) at rest and 90-115 bpm during moderate exercise.

The methods may include administering a composition of the present invention to a subject in need thereof. The subject may be human, or an animal, such as an animal typically used as a model in the study and evaluation of treatments for a cardiac pacing condition, such as a dog or pig, sheep, or non-human primate.

The present invention is illustrated by the following examples. It is to be understood that the particular examples, materials, amounts, and procedures are to be interpreted broadly in accordance with the scope and spirit of the invention as set forth herein.

Example 1

This example describes the development a super-truncated HCN4 construct in order to be packaged in size limited scAAV vector and to be applicable across species and between human without inducing an immune response. Further, an AAV1 vector carrying this super-truncated HCN4 was to be generated by exploring an alternative AAV generation technology. The pace maker function was confirmed by ex vivo evaluation.

Background

Previously we had demonstrated biological pacemaker function using both human full length HCN4 polypeptide (wtHCN4) and a human C-terminal truncated HCN4 version (HCN4t) having amino acids 1-738 of SEQ ID NO:8, packaged in an adenovirus vector (Adv). We used Adv as a carrier to deliver human hyperpolarization-activated cyclic-nucleotide-gated (HCN) ion channel 4 and established proof of concept that HCN4t, along with the full length HCN4, are capable of generating a ventricular biological pacemaker in an AV blocked canine model (FIG. 3).

Although Adv has shown remarkable efficacy in gene transfer, we developed a clinically relevant vector, traditional adeno-associated virus vector (AAV), to carry a biological pacemaker coding region, HCN4. In comparison with Adv, traditional AAV, also referred to as single-stranded AAV (ssAAV), is a very attractive vector for cardiac gene therapy because of lack of pathogenicity, very low immunogenicity, and long-term gene transfer potential with decreased risk of malignant transformation in small and large animal models.

However, the problems associated with ssAAV vector include a latent period from 10 days to 1 month before ssAAV mediated gene expression peaks. While a 3-4 week waiting period required for ssAAV to reach the steady state may be acceptable for one-time life-saving therapy such as a biological pacemaker, a faster expressing system would certainly be most applicable clinically since it would minimize the time a patient is on electronic pacing as a bridge, and would also provide much quicker feedback to the physician if the biological pacemaker were to need any intervention (e.g., to adjust pacing rate). Therefore, it is desirable to determine whether a different type of AAV vector system, the self-complementary AAV vector system (scAAV) will function.

The traditional AAV system contains single stranded DNA and requires host cell synthesis of the complementary strand. Therefore there is a lag period, when the expression is generally quite slow with the peak function occurring 3-4 weeks after the gene administration. In contrast, scAAV system contains double strand DNA and therefore eliminates the rate-limiting step of second-strand DNA synthesis. Thus, scAAV can attain peak expression in a matter of days. This fast ramp-up feature makes scAAV a very promising vector for clinical applications.

ssAAV can package a coding region and regulatory sequences (including two ITR regions, promoter, transgene, and poly-A signal) roughly the size of 4.8 kilo-base pairs (kb) and allows packaging of HCN4t (2,214 base pairs (bp) for HCN4t versus 3,612 bp for wtHCN4). As for scAAV, it can only package ~2.5 kb of coding region and regulatory sequences. While much shorter than in its wild-type counterpart, the coding region encoding HCN4t is still longer than the packaging capacity of scAAV. We developed an even shorter version of HCN4 construct, so that the packaging in scAAV vector system is feasible. The shorter version was designated super truncated HCN4 (HCN4st).

Figures 4, 5:
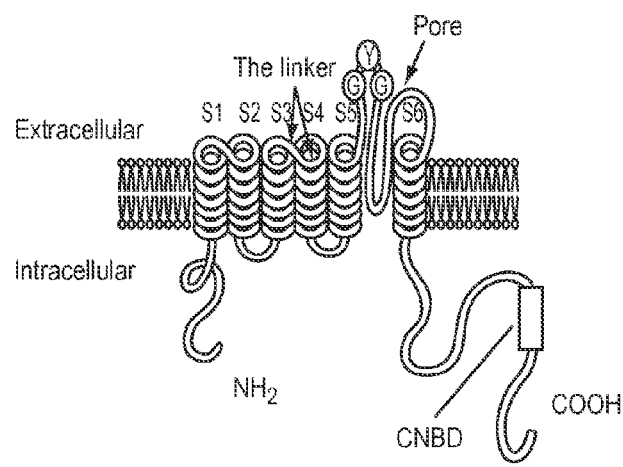
FIG. 4. Sequence homology between canine and human HCN4 coding regions. In comparison with each other, human and canine share high similarity in RNA sequence blocks of I, II and III (92, 95%, and 91% respectively). Other areas (in front of I block, between I to II and II to III blocks, and after block III) display significant distinctive sequences within these two species.
FIG. 5. Schematic diagram of proposed membrane topology of a HCN channel subunit.

In addition to the limitation related to their large sizes, another limitation of the wtHCN4 and HCN4t genes is that they have regions that show inter-species variability. For example, between canine and human genes, there is a considerable lack of homology in the 5' region of the HCN4 gene (FIG. 4). The HCN4st removes all the regions that exhibit inter-species variability and this would imply that the risk of generating an immune response and loss of pacemaker function would be minimized with an HCN4st gene. There are greater than 98% identical residues between human and canine HCN4st1 sequence.

HCN4 channels (FIG. 5) consist of 6 transmembrane domains, with a pore region between S5 and S6 and a cyclic nucleotide-binding domain (CNBD) in the cytoplasmic C-terminal region. While HCN4t deleted nucleotides after the CNBD region, HCN4st was designed to delete regions from the amino terminal end, but not extend into the S1 region. It is within block III of FIG. 4.

In an effort to generate scalable production of AAV vectors, as well as to overcome the toxicity of HCN4 in routine host cells, such as HEK293, a "BAC-to-AAV" technology (Chen U.S. Published Patent Application 20090203071) that uses a baculovirus expression system to produce AAV vectors in insect cells under serum-free condition was used. BAC-to-AAV technology enhances the packaging of much more VP1 proteins into the virions than other systems and therefore greatly increases the performance of AAV vectors.

Methods:

Generating Super-Truncated Version of HCN4 (HCN4st).

HCN4t construct was generated by truncating 1,398 base pairs (bp) nucleotides that encode the C-terminus of wild type HCN4. The truncation site was chosen such that a cyclic nucleotide-binding domain (CNBD) was preserved in the C-terminus region of HCN4t. HCN4st constructs included a series of deletions on the N-terminus of the HCN4t, in front of the six transmembrane domains (FIG. 6).

Figure 7:
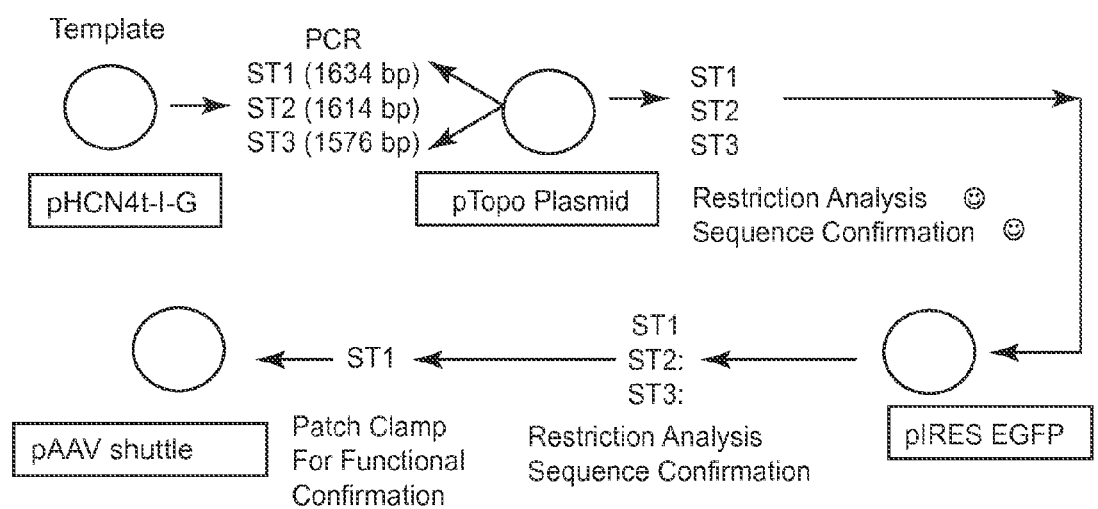
FIG. 7. Schematic diagram of generating super-truncated HCN4 plasmids for biological pacemaker gene therapy.

Each individual HCN4st gene was generated via PCR amplification by using HCN4t as template. Sequence specific primers were designed using the nucleotide sequence available at Genbank accession NM_005477.2. Upstream primers HCN4st were 5' ata gcg cga att ccc gcc atg cag cgc cag ttc ggg (SEQ ID NO:25), 5' ata gcg cga att ccc gcc atg ctc caa ccc ggg g (SEQ ID NO:26) and 5' ata gcg cga att ccc gcc atg ttc ggc agc cag aaa g (SEQ ID NO:27) respectively for HCN4st1, st2 and st3. The coding sequence encoding HCN4st1 encodes a polypeptide corresponding to amino acids 214-719 of SEQ ID NO:8 (FIG. 1), the coding sequence encoding HCN4st2 encodes a polypeptide corresponding to amino acids 221-719 of SEQ ID NO:8, and the coding sequence encoding HCN4st3 encodes a polypeptide corresponding to amino acids 233-719 of SEQ ID NO:8. The downstream primer for each HCN4st was 5' cggcggatcccctagagatat (SEQ ID NO:28). MyC sequence (AGCAGAAGCTGATCTCAGAGGAG-GACCTGCTT, SEQ ID NO:29) was attached at the C-terminal of different HCN4t modifications. Three HCN4st genes were cloned into a pTopo sequence plasmid (Invitrogen, Carlsbad, Calif., USA) and verified by restriction enzyme analysis (New England Biolabs, Ipswich, Mass., USA) and the nucleotide sequence was confirmed (Eurofins MWG Operon, Huntsville, Ala. USA). HCN4st genes were subsequently subcloned into the expression plasmid pIRES-EGFP (Clonetech, Mountain View, Calif., USA) for functional testing by patch clamp. Selected HCN4st genes were further subcloned into an AAV shuttle plasmid (ViroVek, Hayward, Calif., USA) for making B-AAV-HCN4st1 vector (FIG. 7, and described below).

Patch Clamp

HEK 293 Cell Transfection

Human embryonic kidney (HEK293, ATCC) cells were split on 12 well plate one day before transfection. Three pHCN4st-IRES-EGFP plasmids were transfected into 70% confluent HEK293 cells with Fugene 6 (Roche) transfection reagents, along with pHCN4t-IRES-EGFP. The transfected cells were replated on gelatin-fibronectin coated glass coverslips 24 hours after transfection.

Whole Cell Patch Clamp

One day after reculture, the cells plated on a coverslip were transported to a chamber mounted on the stage of a Nikon microscope. The chamber was continuously superfused (~0.5 ml/min) with the Tyrode solution. The whole-cell configuration of the patch-clamp technique (Hamill et al., 1981, Pflugers Arch. 391(2):85-100) was applied. Briefly, glass electrodes (World Precision Instruments, Sarasota, Fla., USA) with 3 to 5 MΩ resistance were connected via an Ag—AgCl wire to an Axopatch 200A amplifier interfaced with a DigiData-1322 acquisition system. After forming a conventional "gigaohm" seal, electrode capacitance was compensated. Additional suction ruptured the patched membrane and formed the whole-cell configuration. Cell membrane capacitance ($C_m$) was measured in each patched cells with the pCLAMP program (version 9.2, Axon Instruments, Foster City, Calif., USA).

The hyperpolarization-activated cyclic nucleotide-gated inward current ($I_h$) was measured with the modified Tyrode bath solution. $I_h$ was evoked by 5 s hyperpolarizing steps to potentials ranging from 0 to −140 mV from a holding potential of −40 mV. The reversal potential of $I_h$ was evaluated by tail currents recorded by 3 s 'tail' steps to membrane potentials ranging from −80 to 20 mV in 10 mV increments followed by a 5 s conditioning potential step to −130 mV every 15 s. The holding potential was set at −40 mV. The activation of $I_h$ was elicited by 3 s 'tail' pulses to −130 mV followed 5 s conditioning pulses from 0 mV to −140 mV in 10 mV increments. The pulse rate was every 30 s.

Data Analysis

Data were collected with the pCLAMP software (version 9.02). $I_h$ was evaluated at a point near the end of each test pulse unless stated otherwise (tail-current measurements). The current amplitudes were normalized with respect to the corresponding values of $C_m$ to minimize the current difference due to cell size. A single-exponential fit (Axon-Clampfit 9.02) of current traces allowed derivation of time constants (τ) of current activation and deactivation. Some data were fitted by a Boltzmann equation $\{1/[1+\exp(V_{1/2}-V)/k]$, where $V_{1/2}$ is the half-inactivation potential, V is the voltage potential, and k is the slope factor (in mV/e-fold change in current)$\}$. The best-fit procedure was performed with a commercial software program (Origin 7.0, Microcal™ Software Inc., Northampton, Mass., USA). All data are presented as mean±standard error of the mean unless otherwise stated. Unpaired Student's t-test was applied for statistical analysis as appropriate. Differences were considered significant if $P \leq 0.05$.

B-AAV1-HCN4st1 Generation

Following patch clamp, functional HCN4st gene was further subcloned and the polynucleotide sequence depicted in FIG. 15 was used as a template for PCR using the primers 5' ata gcg cga att ccc gcc atg cag cgc cag ttc ggg (SEQ ID NO:25) and 5' cggcggatccctagagatat (SEQ ID NO:28), and the amplification product was used by ViroVek to produce an AAV1 vector that encoded an HCN4st1 polypeptide that included a MyC sequence fused to the amino terminal end of the polypeptide. The methods used by ViroVek include cloning gene of interest into an pFB-AAV shuttle plasmid, generation of Bacmid and purification of Bacmid DNA, transfection of Sf9 cells to generate baculovirus, amplification of baculovirus and titration, production of AAV and CsCl purification, and desalting, filter sterilization, and AAV titration (see Chen, U.S. Published Patent Application 20090203071, U.S. Provisional Patent Application 60/839,761, and International Application PCT/US07/76799, and http://www.virovek.com/AAV_Production.html. Together with AAV rep component and vp component, this shuttle vector were co-transfected into SF9 insect cells for generation of recombinant baculovirus and production of a virus vector containing a coding region encoding HCN4st1, designated B-AAV1-HCN4st1, where the "B" refers to generation using the baculovirus system. Following purification of the virus vector through buffer exchange and sterile filtration, virus titer was determined by qPCR. The resulting B-AAV1-HCN4st1 was dissolved in PBS with 0.001% Pluronic F-68 buffer at concentration of 1.03E+13 vg/mL. Endotoxin level was tested by Biotest Labs with <1 EU/ml.

Microelectrode Array (MEA) Measurements

Primary Cell Isolation

Neonatal rats were sacrificed by decapitation and hearts were rapidly excised and washed in $Ca^{2+}$ free balanced salt solution. The ventricles were minced into 1-2 $mm^3$ pieces and dissociated into single cell suspension by repeated digestion with proteolytic enzymes. Each digestion, enhanced with gentle shaking, lasted for 15-20 minutes. Then myocytes were mechanically dispersed by triturating. The undigested masses and first few digestion fractions were discarded after filtering through a cell strainer. Collected cells suspension was mixed with serum for enzyme deactivation, centrifuged, and re-suspended in culturing media. Cells were additionally incubated with 10 μg/ml of DNAse for 10 min at 37° C. For fibroblasts separation and myocytes enrichment two 1.5 hrs pre-plating steps (incubation of cell suspension in 75 $cm^2$ flasks) were performed. After pre-plating, slowly attaching myocytes were separated from quickly attaching fibroblasts, collected, counted, re-suspended, and plated in pretreated MEAs (at −500000 cells/ml, −180000 cells/$cm^2$). Each MEA had ~64 electrodes spaced ~100 μm and covering a total area of approximately 0.5 $mm^2$.

NRVMs were cultured with Norepinephrine and Bromodeoxyuridine (BrDu) for 2 days, than with BrDu for 2 more days, until synchronized spontaneously beating cell monolayers were formed, than maintained in serum free culture media (contained Insulin, BSA, and Vitamin $B_{12}$) preconditioned on cultured fibroblasts.

AAV Transduction

Transfection experiments with serial virus titers were performed twice.

During the first experiment, transfections of myocytes in MEA chambers were carried out on 5th day in culture at the following titers: $10^{11}$, $10^{10}$, $10^9$, $10^8$ vg/ml of B-AAV1-HCN4st1 and non transduction negative control (5 arrays for each condition).

During the second experiment, in addition to B-AAV1-HCN4st1 and negative control, a control of B-AAV1-empty particles was included.

MEA System

The day before transduction, and then each following day, electrograms for each culture were recorded with MEA system and microscopic fluorescence and bright field images of each array were taken with Leica inverted microscope at 10× magnification. Cultures were monitored for about 2 weeks, after which MEA recordings were processed using "MC Rack" Multi Channel Systems Software and analyzed in Microsoft Excel; microscopic images were processed with "ImageJ" software.

NRVM cultures showing signs of degradation were rapidly assessed for apoptosis with Vibrant Apoptosis Assay Kit #5 (Invitrogen, Carlsbbad, Calif., USA) based on fluorescence detection of the compacted state of the chromatin in apoptotic cells.

Results

HCN4st1, st2 and st3 Evaluation by Patch Clamp.

Figure 8:
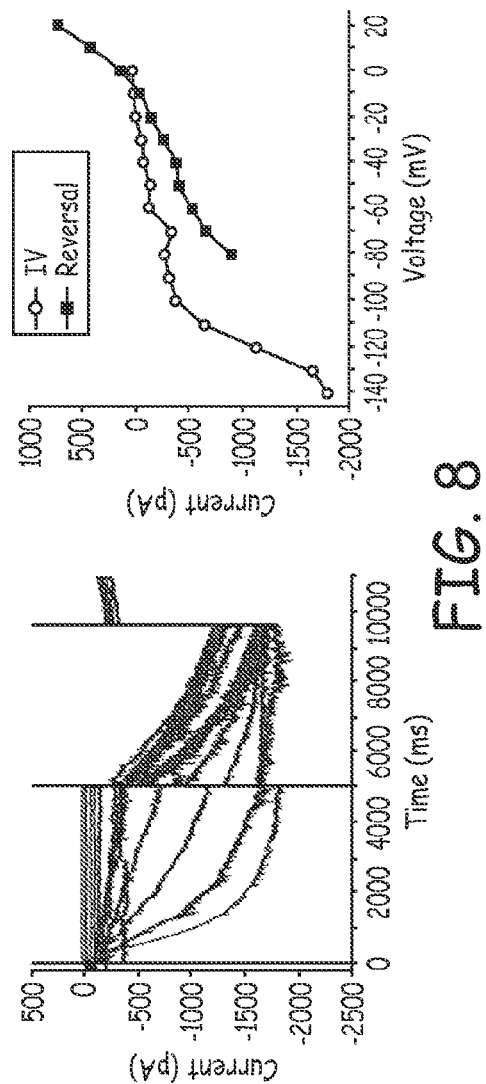
FIG. 8. Confirmation of functionality of HCN4st1 using patch clamp experiments. The panel on the left shows current responses as the cell membrane is pulsed to increasing hyperpolarizing voltages from a positive holding potential at which HCN4 channels are closed. The right panel shows the current-voltage relationship using two different pulse protocols. The electrophysiology of the channel, including reversal potential, is unaltered compared to its wild typed (wtHCN4) and truncated (HCN4t) counterparts.

We have expressed three HCN4st constructs individually in HEK293 cells by Fugene 6 transfection and performed whole-cell patch clamp experiments to assess their electrophysiology function. Our experiments suggested that only HCN4st1 remained indistinguishable from the HCN4t, thus suggesting that truncation at N-terminus of 213 amino acids does not compromise HCN4 function (FIG. 8). When using HEK293 cells HCN4st2 and HCN4st3 did not lead to functional HCN4 current, indicating that these constructs may not function properly in HEK293 cells, or that further modification on these two deletions may be needed. HCN4st1 gene contains only 1575 bp nucleotides, well within the packaging capacity of scAAV vector system, and has both the C-terminus and N-terminus truncated.

B-AAV1-HCN4st1 in Vitro Evaluation by MEA

Figure 9:
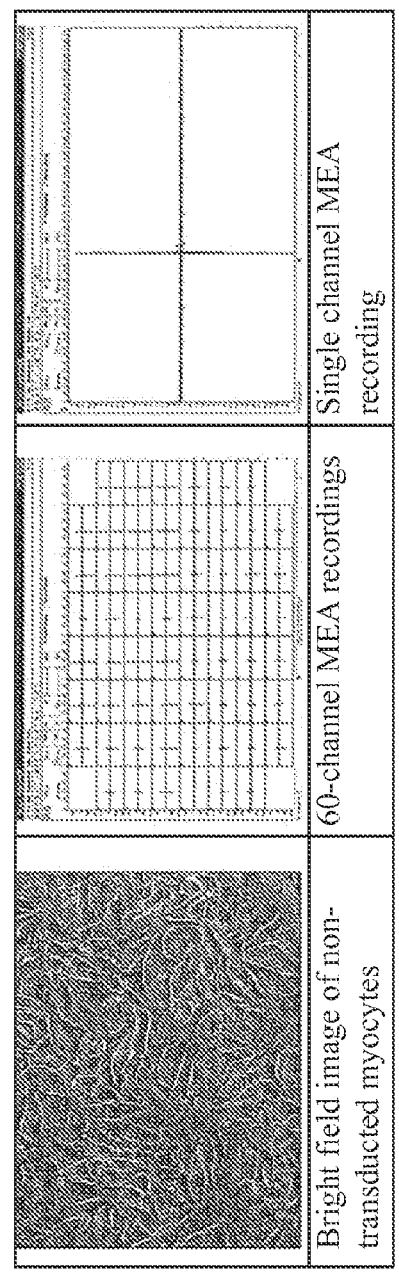
FIG. 9. Cell image and recordings obtained using a microelectrode array (MEA) of non-transduced neo-natal rat ventricular myocytes (NRVMs).

Non transduced control NRVM cells demonstrated stable (~20-40 BPM) beating rates and overall uniform healthy appearance during the two week observation period (FIG. 9).

Figure 10:
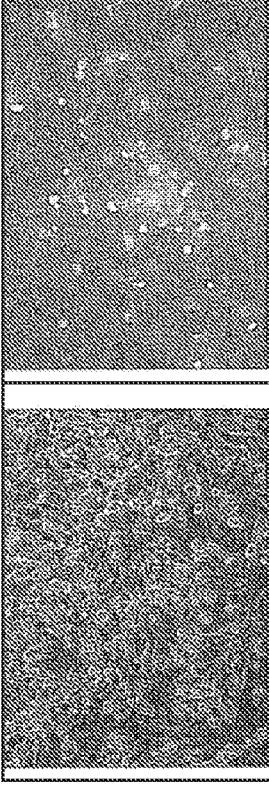
FIG. 10. Cell image and MEA recordings obtained from NRVM cells transduced with $10^{11}$ vg/ml of B-AAV1-HCN4st1 virus.

NRVM cells transduced with $10^{11}$ vg/ml of B-AAV1-HCN4st1 were not beating by the next day after transduction and rapidly degraded showing the signs of apoptosis (FIG. 10).

For the next lower titer $-10^{10}$ vg/ml NRVM cells reached the maximum of beating rate ~115 BPM by day 3 after transduction, and then degraded by day 7.

For the $10^9$ vg/ml titer, NRVM cells reached maximum of beating rate ~130-160 BPM by the day 6 and degraded by the day 10.

Figure 11:
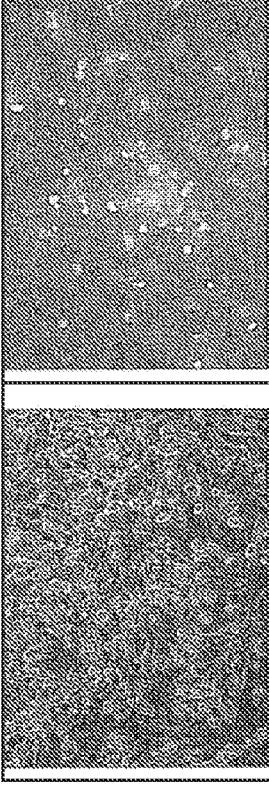
FIG. 11. MEA recordings obtained from NRVMs transduced with $10^{10}$–$10^8$ vg/ml of B-AAV1-HCN4st1 virus.
Figure 12:
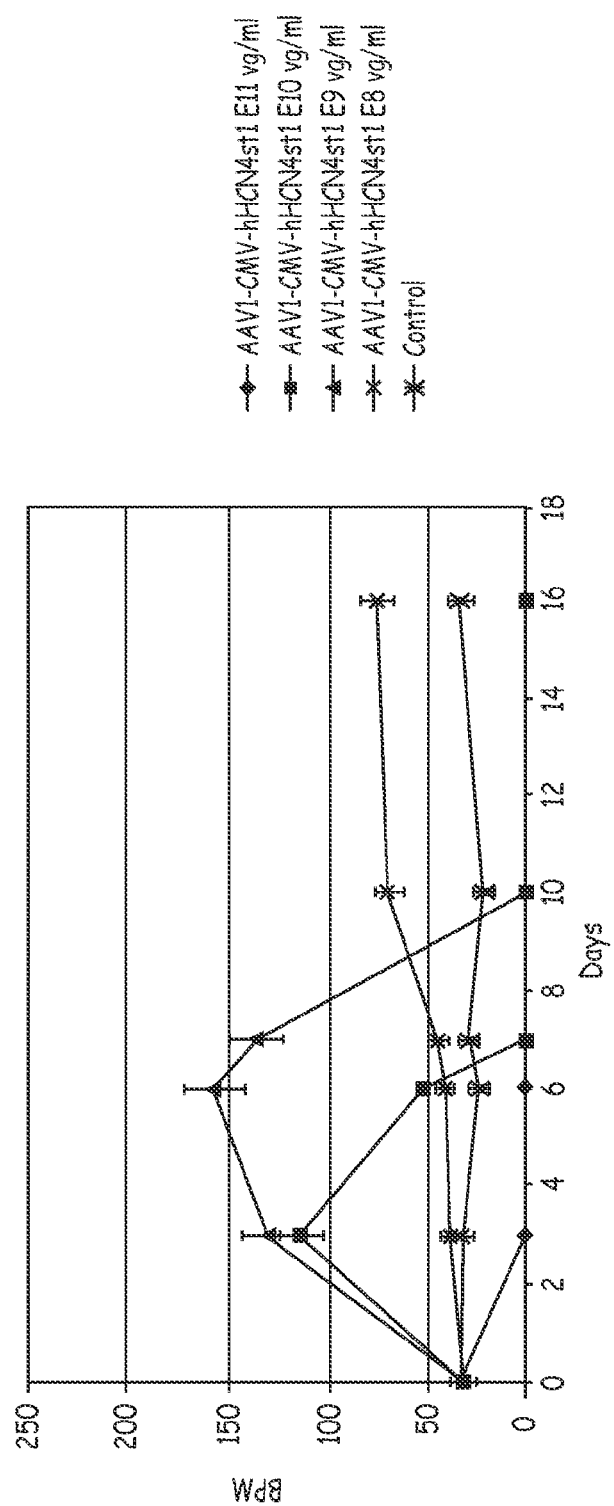
FIG. 12. Time course of NRVMs beating rates following transduction with B-AAV1-HCN4st1 at various doses.

For the lowest tested $10^8$ vg/ml titer, NRVM cells reached beating rate ~75 BPM by the day 10 and did not show signs of degradation (FIG. 11, FIG. 12).

Figure 13:
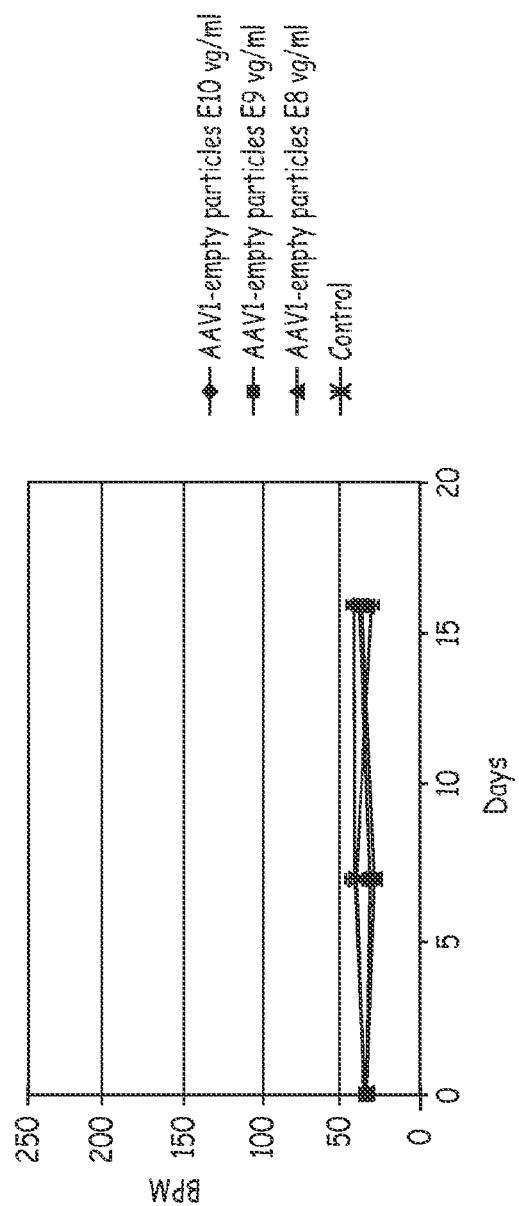
FIG. 13. Time course of NRVMs beating rates after transduction with B-AAV1-empty vector at various doses.
Figure 14:
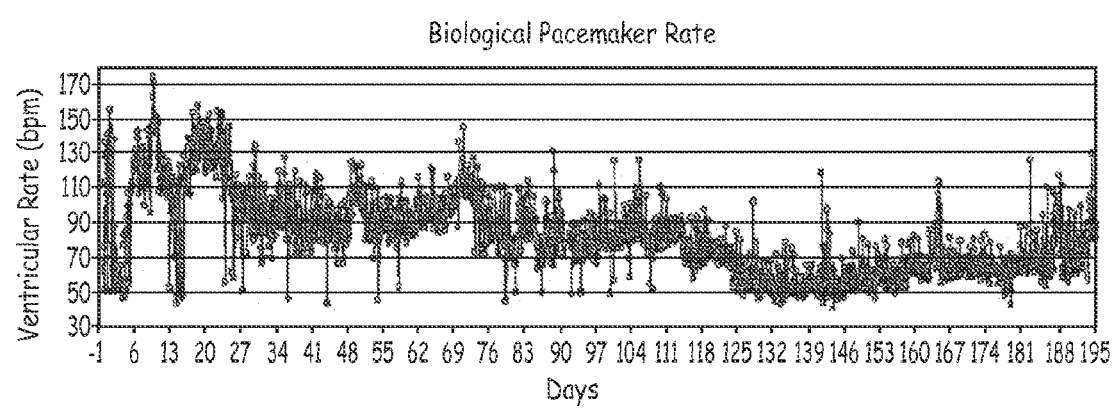
FIG. 14. Biological pacemaker from AV node ablated canine injected with hHCN4st1 gene.

NRVM cells transduced with B-AAV1-empty particles did not show any signs of degradation and any noticeable rate increase compared to non transduced controls (FIG. 13).

Overall, neonatal rat ventricular myocytes transduced with B-AAV1-HCN4st1 showed increased induced beating. At higher titers ($10^{11}$, $10^{10}$, $10^9$ vg/ml), B-AAV1-HCN4st1 caused cell degradation via apoptosis. At lower titer ($10^8$ vg/ml), B-AAV1-HCN4st1 was safe and reached induced beating rate at ~75 BPM.

Example 2

AAV1-HCN4-mediated biological pacemaker paces the canine heart with AV block over 7 months and responds well to autonomic challenges Implantation of an electronic pacemaker is necessary for a patient with severe bradycardia; however, while effectively improving the lives of many patients, such therapy has several limitations including hardware complications, limited battery life and lack of response to autonomic and physiologic demands on hearts. Compared to its counterpart, a biological pacemaker is a conceptually attractive alternative to electronic pacemakers.

This study was to test whether using adeno-associate virus-1 (AAV1) with truncated human HCN4 (hHCN4tr) would create a long-term (>6 months) and sustained (nearly 100% biologically induced pacing) biological pacemaker in the left ventricle (LV) of canines with atrioventricular (AV) nodal block.

Canines (n=3) with neutralizing anti-AAV1 antibodies (NAb) at a titer≤1:40 serum dilution were selected. After complete AV block, the AAV1-hHCN4tr vectors were epicardially injected into the LV apex using a side-hole needle as described in Hiniduma-Lokuge et al. (PCT Publication No. WO/2008/055001). An electrical pacemaker (VVI 50 bpm) was implanted for backup pacing and recording of the electrocardiograms every two hours. During the follow-up monitoring, drug and exercise challenges were performed. Twenty-four hour Holter monitoring and pacemaker log record checks were also performed.

All canines demonstrated biological pacemaker activities 3 days after AAV1-hHCN4tr injection. The biological pacemaker in two canines with NAb at a titer of 1:40 diminished 3 weeks after the gene transfer presumably due to the pre-existing immunity to AAV1. However, the canine with NAb at a titer of 1:20 has exhibited sustained biological pacing activities at a range of 60-150 bpm over 7 months at the time of this abstract submission (FIG. 15). The electrical pacemaker intervened at 50 bpm when spontaneous ventricular rate fell below at that rate, triggering for <2% of the beats. The biological pacemaker responded well to drugs, such as isoproterenol and metoprolol, and also showed physiological diurnal variations and responses to exercise.

Conclusion: LV epicardial injection with AAV1-hHCN4tr creates long-term (over 7 months) and sustained (nearly 100% biologically induced pacing) biological pacemaker activities in a complete AV block canine model. Interestingly, such biological pacemaker responds well to autonomic challenges and physiological exercise.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for treating a cardiac pacing condition, the method comprising administering to a subject in need thereof an effective amount of an isolated polynucleotide sequence, the polynucleotide sequence encoding a truncated human hyperpolarization-activated and cyclic nucleotide-gated (HCN) polypeptide having channel activity,
   wherein the truncated human HCN polypeptide comprises a N-terminal region truncation comprising the deletion from the N terminal amino acid up to, but not including, the amino acids of the S1α helical segment of the HCN polypeptide;
   wherein the truncated human HCN polypeptide begins with an amino acid residue selected from amino acid 92 up to amino acid 214 of SEQ ID NO:8;
   wherein the encoded truncated human HCN polypeptide comprises at least amino acids 214-723 of SEQ ID NO:8 and conservative substitutions thereof; and
   wherein the encoded truncated human HCN polypeptide demonstrates hyperpolarization-activated and cyclic nucleotide-gated channel activity unaltered from the wild type human HCN polypeptide.

2. The method of claim 1 wherein the HCN polynucleotide is DNA.

3. The method of claim 1 wherein the HCN polynucleotide is RNA.

4. The method of claim 1 wherein the HCN polynucleotide is present in a genetically modified cell.

5. The method of claim 4 wherein the HCN polynucleotide is integrated in genomic DNA of the genetically modified cell.

6. The method of claim 4 wherein the genetically modified cell comprises an extra-chromosomal vector which comprises the HCN polynucleotide.

7. The method of claim 1 wherein the administering comprises introduction of the HCN polynucleotide into cardiac atrium cells or cardiac ventricle cells.

8. The method of claim 1 wherein the administering comprises use of a syringe.

9. The method of claim 1 wherein the administering comprises use of a catheter.

10. The method of claim 1 wherein the HCN polynucleotide is present in a vector.

11. The method of claim 10 wherein the vector is a viral vector, a transposon vector, or a plasmid vector.

12. The method of claim 11 wherein the viral vector is a single strand adeno-associated virus or a self complementary adeno-associated virus.

13. The method of claim 1, wherein the truncated human HCN polypeptide further comprises a C-terminal region truncation.

14. The method of claim 13, wherein the C-terminal region truncation comprises deletion of the C terminal amino acids after the cyclic nucleotide-binding domain (CNBD).

15. The method claim 1, wherein the truncated human HCN polypeptide further comprises mutations of the S3-S4 linker region.

16. The method of claim 15, wherein the S3-S4 linker region mutation is selected from the group consisting of T360A, Δ363-367, T360A+Δ363-367, TRI360-362AGM, TRI360-362KGM, T360A+I362M, T360A+Δ365-367, E365G, E365A, R361G, TR360-361AA, I362C, I362S, I362T, and TRI360-362AGM+Δ363-367.

17. The method of claim 14, wherein the truncated human HCN polypeptide further comprises mutations of the S3-S4 linker region.

18. The method of claim 17, wherein the S3-S4 linker region mutation is selected from the group consisting of T360A, Δ363-367, T360A+Δ363-367, TRI360-362AGM, TRI360-362KGM, T360A+I362M, T360A+Δ365-367, E365G, E365A, R361G, TR360-361AA, I362C, I362S, I362T, and TRI360-362AGM+Δ363-367.

19. The method of claim 14, wherein the HCN polynucleotide is present in a self complementary adeno-associated viral (scAAV) vector.

20. The method of claim 1, wherein the HCN polynucleotide is present in a self complementary adeno-associated viral (scAAV) vector.

* * * * *

SEQUENCE LISTING

<160> NUMBER OF SEQ ID NOS: 31

<210> SEQ ID NO 1
<211> LENGTH: 2673
<212> TYPE: DNA
<213> ORGANISM: human
<220> FEATURE:
<221> NAME/KEY: CDS
<222> LOCATION: (1)..(2673)

<400> SEQUENCE: 1

```
atg gaa gga ggc ggc aag ccc aac tct tcg tct aac agc cgg gac gat      48
Met Glu Gly Gly Gly Lys Pro Asn Ser Ser Ser Asn Ser Arg Asp Asp
1               5                   10                  15 ggc aac agc gtc ttc ccc gcc aag gcg tcc gcg acg ggc gcg ggg ccg      96
Gly Asn Ser Val Phe Pro Ala Lys Ala Ser Ala Thr Gly Ala Gly Pro
                20                  25                  30 gcc gcg gcc gag aag cgc ctg ggc acc ccg ccg ggg ggc ggg gcc          144
Ala Ala Ala Glu Lys Arg Leu Gly Thr Pro Pro Gly Gly Gly Ala
            35                  40                  45 ggc gcg aag gag cac ggc aac tcc gtg tgc ttc aag gtg gac ggc ggt      192
Gly Ala Lys Glu His Gly Asn Ser Val Cys Phe Lys Val Asp Gly Gly
        50                  55                  60 ggc ggt ggt ggc ggc ggc ggc ggc ggc gag gag ccg gcg ggg ggc          240
Gly Gly Gly Gly Gly Gly Gly Gly Gly Glu Glu Pro Ala Gly Gly
65                  70                  75                  80 ttc gaa gac gcc gag ggg ccc cgg cgg cag tac ggc ttc atg cag agg      288
Phe Glu Asp Ala Glu Gly Pro Arg Arg Gln Tyr Gly Phe Met Gln Arg
                85                  90                  95 cag ttc acc tcc atg ctg cag ccc ggg gtc aac aaa ttc tcc ctc cgc      336
Gln Phe Thr Ser Met Leu Gln Pro Gly Val Asn Lys Phe Ser Leu Arg
                100                 105                 110 atg ttt ggg agc cag aag gcg gtg gaa aag gag cag gaa agg gtt aaa      384
Met Phe Gly Ser Gln Lys Ala Val Glu Lys Glu Gln Glu Arg Val Lys
            115                 120                 125 act gca ggc ttc tgg att atc cac cct tac agt gat ttc agg ttt tac      432
Thr Ala Gly Phe Trp Ile Ile His Pro Tyr Ser Asp Phe Arg Phe Tyr
        130                 135                 140 tgg gat tta ata atg ctt ata atg atg gtt gga aat cta gtc atc ata      480
Trp Asp Leu Ile Met Leu Ile Met Met Val Gly Asn Leu Val Ile Ile
145                 150                 155                 160 cca gtt gga atc aca ttc ttt aca gag caa aca aca aca cca tgg att      528
Pro Val Gly Ile Thr Phe Phe Thr Glu Gln Thr Thr Thr Pro Trp Ile
                165                 170                 175 att ttc aat gtg gca tca gat aca gtt ttc cta ttg gac ctg atc atg      576
Ile Phe Asn Val Ala Ser Asp Thr Val Phe Leu Leu Asp Leu Ile Met
            180                 185                 190 aat ttt agg act ggg act gtc aat gaa gac agt tct gaa atc atc ctg      624
Asn Phe Arg Thr Gly Thr Val Asn Glu Asp Ser Ser Glu Ile Ile Leu
        195                 200                 205 gac ccc aaa gtg atc aag atg aat tat tta aaa agc tgg ttt gtg gtt      672
Asp Pro Lys Val Ile Lys Met Asn Tyr Leu Lys Ser Trp Phe Val Val
    210                 215                 220 gac ttc atc tca tcc atc cca gtg gat tat atc ttt ctt att gta gaa      720
Asp Phe Ile Ser Ser Ile Pro Val Asp Tyr Ile Phe Leu Ile Val Glu
225                 230                 235                 240 aaa gga atg gat tct gaa gtt tac aag aca gcc agg gca ctt cgc att      768
Lys Gly Met Asp Ser Glu Val Tyr Lys Thr Ala Arg Ala Leu Arg Ile
                245                 250                 255 gtg agg ttt aca aaa att ctc agt ctc ttg cgt tta tta cga ctt tca      816
```

```
Val Arg Phe Thr Lys Ile Leu Ser Leu Leu Arg Leu Leu Arg Leu Ser
                260                 265                 270 agg tta att aga tac ata cat caa tgg gaa gag ata ttc cac atg aca    864
Arg Leu Ile Arg Tyr Ile His Gln Trp Glu Glu Ile Phe His Met Thr
            275                 280                 285 tat gat ctc gcc agt gca gtg gtg aga att ttt aat ctc atc ggc atg    912
Tyr Asp Leu Ala Ser Ala Val Val Arg Ile Phe Asn Leu Ile Gly Met
        290                 295                 300 atg ctg ctc ctg tgc cac tgg gat ggt tgt ctt cag ttc tta gta cca    960
Met Leu Leu Leu Cys His Trp Asp Gly Cys Leu Gln Phe Leu Val Pro
305                 310                 315                 320 cta ctg cag gac ttc cca cca gat tgc tgg gtg tct tta aat gaa atg   1008
Leu Leu Gln Asp Phe Pro Pro Asp Cys Trp Val Ser Leu Asn Glu Met
                325                 330                 335 gtt aat gat tct tgg gga aag cag tat tca tac gca ctc ttc aaa gct   1056
Val Asn Asp Ser Trp Gly Lys Gln Tyr Ser Tyr Ala Leu Phe Lys Ala
            340                 345                 350 atg agt cac atg ctg tgc att ggg tat gga gcc caa gcc cca gtc agc   1104
Met Ser His Met Leu Cys Ile Gly Tyr Gly Ala Gln Ala Pro Val Ser
        355                 360                 365 atg tct gac ctc tgg att acc atg ctg agc atg atc gtc ggg gcc acc   1152
Met Ser Asp Leu Trp Ile Thr Met Leu Ser Met Ile Val Gly Ala Thr
370                 375                 380 tgc tat gcc atg ttt gtc ggc cat gcc acc gct tta atc cag tct ctg   1200
Cys Tyr Ala Met Phe Val Gly His Ala Thr Ala Leu Ile Gln Ser Leu
385                 390                 395                 400 gat tct tcg agg cgg cag tat caa gag aag tat aag caa gtg gaa caa   1248
Asp Ser Ser Arg Arg Gln Tyr Gln Glu Lys Tyr Lys Gln Val Glu Gln
                405                 410                 415 tac atg tca ttc cat aag tta cca gct gat atg cgt cag aag ata cat   1296
Tyr Met Ser Phe His Lys Leu Pro Ala Asp Met Arg Gln Lys Ile His
            420                 425                 430 gat tac tat gaa cac aga tac caa ggc aaa atc ttt gat gag gaa aat   1344
Asp Tyr Tyr Glu His Arg Tyr Gln Gly Lys Ile Phe Asp Glu Glu Asn
        435                 440                 445 att ctc aat gaa ctc aat gat cct ctg aga gag gag ata gtc aac ttc   1392
Ile Leu Asn Glu Leu Asn Asp Pro Leu Arg Glu Glu Ile Val Asn Phe
450                 455                 460 aac tgt cgg aaa ctg gtg gct aca atg cct tta ttt gct aat gcg gat   1440
Asn Cys Arg Lys Leu Val Ala Thr Met Pro Leu Phe Ala Asn Ala Asp
465                 470                 475                 480 cct aat ttt gtg act gcc atg ctg agc aag ttg aga ttt gag gtg ttt   1488
Pro Asn Phe Val Thr Ala Met Leu Ser Lys Leu Arg Phe Glu Val Phe
                485                 490                 495 caa cct gga gat tat atc ata cga gaa gga gcc gtg ggt aaa aaa atg   1536
Gln Pro Gly Asp Tyr Ile Ile Arg Glu Gly Ala Val Gly Lys Lys Met
            500                 505                 510 tat ttc att caa cac ggt gtt gct ggt gtc att aca aaa tcc agt aaa   1584
Tyr Phe Ile Gln His Gly Val Ala Gly Val Ile Thr Lys Ser Ser Lys
        515                 520                 525 gaa atg aag ctg aca gat ggc tct tac ttt gga gag att tgc ctg ctg   1632
Glu Met Lys Leu Thr Asp Gly Ser Tyr Phe Gly Glu Ile Cys Leu Leu
530                 535                 540 acc aaa gga cgt cgt act gcc agt gtt cga gct gat aca tat tgt cgt   1680
Thr Lys Gly Arg Arg Thr Ala Ser Val Arg Ala Asp Thr Tyr Cys Arg
545                 550                 555                 560 ctt tac tca ctt tcc gtg gac aat ttc aac gag gtc ctg gag gaa tat   1728
Leu Tyr Ser Leu Ser Val Asp Asn Phe Asn Glu Val Leu Glu Glu Tyr
                565                 570                 575 cca atg atg agg aga gcc ttt gag aca gtt gcc att gac cga cta gat   1776
```

```
        Pro Met Met Arg Arg Ala Phe Glu Thr Val Ala Ile Asp Arg Leu Asp
                    580                 585                 590 cga ata gga aag aaa aat tca att ctt ctg caa aag ttc cag aag gat      1824
        Arg Ile Gly Lys Lys Asn Ser Ile Leu Leu Gln Lys Phe Gln Lys Asp
                    595                 600                 605 ctg aac act ggt gtt ttc aac aat cag gag aac gaa atc ctc aag cag      1872
        Leu Asn Thr Gly Val Phe Asn Asn Gln Glu Asn Glu Ile Leu Lys Gln
                    610                 615                 620 att gtg aaa cat gac agg gag atg gtg cag gca atc gct ccc atc aat      1920
        Ile Val Lys His Asp Arg Glu Met Val Gln Ala Ile Ala Pro Ile Asn
        625                 630                 635                 640 tat cct caa atg aca acc ctg aat tcc aca tcg tct act acg acc ccg      1968
        Tyr Pro Gln Met Thr Thr Leu Asn Ser Thr Ser Ser Thr Thr Thr Pro
                            645                 650                 655 acc tcc cgc atg agg aca caa tct cca ccg gtg tac aca gcg acc agc      2016
        Thr Ser Arg Met Arg Thr Gln Ser Pro Pro Val Tyr Thr Ala Thr Ser
                        660                 665                 670 ctg tct cac agc aac ctg cac tcc ccc agt ccc agc aca cag acc ccc      2064
        Leu Ser His Ser Asn Leu His Ser Pro Ser Pro Ser Thr Gln Thr Pro
                    675                 680                 685 cag cca tca gcc atc ctg tca ccc tgc tcc tac acc acc gcg gtc tgc      2112
        Gln Pro Ser Ala Ile Leu Ser Pro Cys Ser Tyr Thr Thr Ala Val Cys
                690                 695                 700 agc cct cct gta cag agc cct ctg gcc gct cga act ttc cac tat gcc      2160
        Ser Pro Pro Val Gln Ser Pro Leu Ala Ala Arg Thr Phe His Tyr Ala
        705                 710                 715                 720 tcc ccc acc gcc tcc cag ctg tca ctc atg caa cag cag ccg cag cag      2208
        Ser Pro Thr Ala Ser Gln Leu Ser Leu Met Gln Gln Gln Pro Gln Gln
                            725                 730                 735 cag gta cag cag tcc cag ccg ccg cag act cag cca cag cag ccg tcc      2256
        Gln Val Gln Gln Ser Gln Pro Pro Gln Thr Gln Pro Gln Gln Pro Ser
                        740                 745                 750 ccg cag cca cag aca cct ggc agc tcc acg ccg aaa aat gaa gtg cac      2304
        Pro Gln Pro Gln Thr Pro Gly Ser Ser Thr Pro Lys Asn Glu Val His
                    755                 760                 765 aag agc acg cag gcg ctt cac aac acc aac ctg acc cgg gaa gtc agg      2352
        Lys Ser Thr Gln Ala Leu His Asn Thr Asn Leu Thr Arg Glu Val Arg
                770                 775                 780 cca ctc tcc gcc tcg cag ccc tcg ctg ccc cat gag gtg tcc act ctg      2400
        Pro Leu Ser Ala Ser Gln Pro Ser Leu Pro His Glu Val Ser Thr Leu
        785                 790                 795                 800 att tcc aga cct cat ccc act gtg ggc gag tcc ctg gcc tcc atc cct      2448
        Ile Ser Arg Pro His Pro Thr Val Gly Glu Ser Leu Ala Ser Ile Pro
                            805                 810                 815 caa ccc gtg acg gcg gtc ccc gga acg ggc ctt cag gca ggg ggc agg      2496
        Gln Pro Val Thr Ala Val Pro Gly Thr Gly Leu Gln Ala Gly Gly Arg
                        820                 825                 830 agc act gtc ccg cag cgc gtc acc ctc ttc cga cag atg tcg tcg gga      2544
        Ser Thr Val Pro Gln Arg Val Thr Leu Phe Arg Gln Met Ser Ser Gly
                    835                 840                 845 gcc atc ccc ccg aac cga gga gtc cct cca gca ccc cct cca cca gca      2592
        Ala Ile Pro Pro Asn Arg Gly Val Pro Pro Ala Pro Pro Pro Pro Ala
                850                 855                 860 gct gct ctt cca aga gaa tct tcc tca gtc tta aac aca gac cca gac      2640
        Ala Ala Leu Pro Arg Glu Ser Ser Ser Val Leu Asn Thr Asp Pro Asp
        865                 870                 875                 880 gca gaa aag cca cga ttt gct tca aat tta tga                          2673
        Ala Glu Lys Pro Arg Phe Ala Ser Asn Leu
                            885                 890
```

```
<210> SEQ ID NO 2
<211> LENGTH: 890
<212> TYPE: PRT
<213> ORGANISM: human

<400> SEQUENCE: 2

Met Glu Gly Gly Gly Lys Pro Asn Ser Ser Ser Asn Ser Arg Asp Asp
1               5                   10                  15

Gly Asn Ser Val Phe Pro Ala Lys Ala Ser Ala Thr Gly Ala Gly Pro
            20                  25                  30

Ala Ala Ala Glu Lys Arg Leu Gly Thr Pro Pro Gly Gly Gly Gly Ala
        35                  40                  45

Gly Ala Lys Glu His Gly Asn Ser Val Cys Phe Lys Val Asp Gly Gly
    50                  55                  60

Gly Gly Gly Gly Gly Gly Gly Gly Glu Glu Pro Ala Gly Gly
65                  70                  75                  80

Phe Glu Asp Ala Glu Gly Pro Arg Arg Gln Tyr Gly Phe Met Gln Arg
                85                  90                  95

Gln Phe Thr Ser Met Leu Gln Pro Gly Val Asn Lys Phe Ser Leu Arg
            100                 105                 110

Met Phe Gly Ser Gln Lys Ala Val Glu Lys Glu Gln Glu Arg Val Lys
        115                 120                 125

Thr Ala Gly Phe Trp Ile Ile His Pro Tyr Ser Asp Phe Arg Phe Tyr
    130                 135                 140

Trp Asp Leu Ile Met Leu Ile Met Met Val Gly Asn Leu Val Ile Ile
145                 150                 155                 160

Pro Val Gly Ile Thr Phe Phe Thr Glu Gln Thr Thr Thr Pro Trp Ile
                165                 170                 175

Ile Phe Asn Val Ala Ser Asp Thr Val Phe Leu Leu Asp Leu Ile Met
            180                 185                 190

Asn Phe Arg Thr Gly Thr Val Asn Glu Asp Ser Ser Glu Ile Ile Leu
        195                 200                 205

Asp Pro Lys Val Ile Lys Met Asn Tyr Leu Lys Ser Trp Phe Val Val
    210                 215                 220

Asp Phe Ile Ser Ser Ile Pro Val Asp Tyr Ile Phe Leu Ile Val Glu
225                 230                 235                 240

Lys Gly Met Asp Ser Glu Val Tyr Lys Thr Ala Arg Ala Leu Arg Ile
                245                 250                 255

Val Arg Phe Thr Lys Ile Leu Ser Leu Leu Arg Leu Leu Arg Leu Ser
            260                 265                 270

Arg Leu Ile Arg Tyr Ile His Gln Trp Glu Glu Ile Phe His Met Thr
        275                 280                 285

Tyr Asp Leu Ala Ser Ala Val Val Arg Ile Phe Asn Leu Ile Gly Met
    290                 295                 300

Met Leu Leu Leu Cys His Trp Asp Gly Cys Leu Gln Phe Leu Val Pro
305                 310                 315                 320

Leu Leu Gln Asp Phe Pro Pro Asp Cys Trp Val Ser Leu Asn Glu Met
                325                 330                 335

Val Asn Asp Ser Trp Gly Lys Gln Tyr Ser Tyr Ala Leu Phe Lys Ala
            340                 345                 350

Met Ser His Met Leu Cys Ile Gly Tyr Gly Ala Gln Ala Pro Val Ser
        355                 360                 365

Met Ser Asp Leu Trp Ile Thr Met Leu Ser Met Ile Val Gly Ala Thr
    370                 375                 380

Cys Tyr Ala Met Phe Val Gly His Ala Thr Ala Leu Ile Gln Ser Leu
```

-continued

```
            385                 390                 395                 400
Asp Ser Ser Arg Arg Gln Tyr Gln Glu Lys Tyr Lys Gln Val Glu Gln
                405                 410                 415

Tyr Met Ser Phe His Lys Leu Pro Ala Asp Met Arg Gln Lys Ile His
                420                 425                 430

Asp Tyr Tyr Glu His Arg Tyr Gln Gly Lys Ile Phe Asp Glu Glu Asn
                435                 440                 445

Ile Leu Asn Glu Leu Asn Asp Pro Leu Arg Glu Glu Ile Val Asn Phe
450                 455                 460

Asn Cys Arg Lys Leu Val Ala Thr Met Pro Leu Phe Ala Asn Ala Asp
465                 470                 475                 480

Pro Asn Phe Val Thr Ala Met Leu Ser Lys Leu Arg Phe Glu Val Phe
                485                 490                 495

Gln Pro Gly Asp Tyr Ile Ile Arg Glu Gly Ala Val Gly Lys Lys Met
                500                 505                 510

Tyr Phe Ile Gln His Gly Val Ala Gly Val Ile Thr Lys Ser Ser Lys
                515                 520                 525

Glu Met Lys Leu Thr Asp Gly Ser Tyr Phe Gly Glu Ile Cys Leu Leu
                530                 535                 540

Thr Lys Gly Arg Arg Thr Ala Ser Val Arg Ala Asp Thr Tyr Cys Arg
545                 550                 555                 560

Leu Tyr Ser Leu Ser Val Asp Asn Phe Asn Glu Val Leu Glu Glu Tyr
                565                 570                 575

Pro Met Met Arg Arg Ala Phe Glu Thr Val Ala Ile Asp Arg Leu Asp
                580                 585                 590

Arg Ile Gly Lys Lys Asn Ser Ile Leu Leu Gln Lys Phe Gln Lys Asp
                595                 600                 605

Leu Asn Thr Gly Val Phe Asn Asn Gln Glu Asn Glu Ile Leu Lys Gln
                610                 615                 620

Ile Val Lys His Asp Arg Glu Met Val Gln Ala Ile Ala Pro Ile Asn
625                 630                 635                 640

Tyr Pro Gln Met Thr Thr Leu Asn Ser Thr Ser Ser Thr Thr Thr Pro
                645                 650                 655

Thr Ser Arg Met Arg Thr Gln Ser Pro Pro Val Tyr Thr Ala Thr Ser
                660                 665                 670

Leu Ser His Ser Asn Leu His Ser Pro Ser Pro Ser Thr Gln Thr Pro
                675                 680                 685

Gln Pro Ser Ala Ile Leu Ser Pro Cys Ser Tyr Thr Thr Ala Val Cys
                690                 695                 700

Ser Pro Pro Val Gln Ser Pro Leu Ala Ala Arg Thr Phe His Tyr Ala
705                 710                 715                 720

Ser Pro Thr Ala Ser Gln Leu Ser Leu Met Gln Gln Gln Pro Gln Gln
                725                 730                 735

Gln Val Gln Gln Ser Gln Pro Pro Gln Thr Gln Pro Gln Pro Gln Ser
                740                 745                 750

Pro Gln Pro Gln Thr Pro Gly Ser Ser Thr Pro Lys Asn Glu Val His
                755                 760                 765

Lys Ser Thr Gln Ala Leu His Asn Thr Asn Leu Thr Arg Glu Val Arg
                770                 775                 780

Pro Leu Ser Ala Ser Gln Pro Ser Leu Pro His Glu Val Ser Thr Leu
785                 790                 795                 800

Ile Ser Arg Pro His Pro Thr Val Gly Glu Ser Leu Ala Ser Ile Pro
                805                 810                 815
```

-continued

```
Gln Pro Val Thr Ala Val Pro Gly Thr Gly Leu Gln Ala Gly Gly Arg
            820                 825                 830

Ser Thr Val Pro Gln Arg Val Thr Leu Phe Arg Gln Met Ser Ser Gly
        835                 840                 845

Ala Ile Pro Pro Asn Arg Gly Val Pro Ala Pro Pro Pro Ala
850                 855                 860

Ala Ala Leu Pro Arg Glu Ser Ser Val Leu Asn Thr Asp Pro Asp
865                 870                 875                 880

Ala Glu Lys Pro Arg Phe Ala Ser Asn Leu
                885                 890

<210> SEQ ID NO 3
<211> LENGTH: 2670
<212> TYPE: DNA
<213> ORGANISM: human
<220> FEATURE:
<221> NAME/KEY: CDS
<222> LOCATION: (1)..(2670)

<400> SEQUENCE: 3
```

| | | |
|---|---|---|
| atg gac gcg cgc ggg ggc ggg cgg ccc ggg gag agc ccg ggc gcg<br>Met Asp Ala Arg Gly Gly Gly Arg Pro Gly Glu Ser Pro Gly Ala<br>1                  5                  10                 15 | 48 |
| acc ccc gcg ccg ggg ccg ccg ccg ccg ccc gcg ccc ccc caa<br>Thr Pro Ala Pro Gly Pro Pro Pro Pro Pro Ala Pro Pro Gln<br>           20                    25                  30 | 96 |
| cag cag ccg ccg ccg ccg ccg ccg ccc gcg ccc ccc ccg ggc ccc ggg<br>Gln Gln Pro Pro Pro Pro Pro Pro Pro Ala Pro Pro Gly Pro Gly<br>              35                  40                 45 | 144 |
| ccc gcg ccc ccc cag cac ccg ccc cgg gcc gag gcg ttg ccc ccg gag<br>Pro Ala Pro Pro Gln His Pro Pro Arg Ala Glu Ala Leu Pro Pro Glu<br>50                  55                  60 | 192 |
| gcg gcg gat gag ggc ggc ccg cgg ggc cgg ctc cgc agc cgc gac agc<br>Ala Ala Asp Glu Gly Gly Pro Arg Gly Arg Leu Arg Ser Arg Asp Ser<br>65                  70                  75                  80 | 240 |
| tcg tgc ggc cgc ccc ggc acc ccg ggc gcg gcg agc acg gcc aag ggc<br>Ser Cys Gly Arg Pro Gly Thr Pro Gly Ala Ala Ser Thr Ala Lys Gly<br>              85                  90                 95 | 288 |
| agc ccg aac ggc gag tgc ggg cgc ggc gag ccg cag tgc agc ccc gcg<br>Ser Pro Asn Gly Glu Cys Gly Arg Gly Glu Pro Gln Cys Ser Pro Ala<br>                 100                105               110 | 336 |
| ggg ccc gag ggc ccg gcg cgg ggg ccc aag gtg tcg ttc tcg tgc cgc<br>Gly Pro Glu Gly Pro Ala Arg Gly Pro Lys Val Ser Phe Ser Cys Arg<br>               115                120               125 | 384 |
| ggg gcg gcc tcg ggg ccc gcg ccg ggg ccg ggg ccg gcg gag gag gcg<br>Gly Ala Ala Ser Gly Pro Ala Pro Gly Pro Gly Pro Ala Glu Glu Ala<br>      130                135                140 | 432 |
| ggc agc gag gag gcg ggc ccg gcg ggg gag ccg cgc ggc agc cag gcc<br>Gly Ser Glu Glu Ala Gly Pro Ala Gly Glu Pro Arg Gly Ser Gln Ala<br>145                  150                155               160 | 480 |
| agc ttc atg cag cgc cag ttc ggc gcg ctc ctg cag ccg ggc gtc aac<br>Ser Phe Met Gln Arg Gln Phe Gly Ala Leu Leu Gln Pro Gly Val Asn<br>               165                170               175 | 528 |
| aag ttc tcg ctg cgg atg ttc ggc agc cag aag gcc gtg gag cgc gag<br>Lys Phe Ser Leu Arg Met Phe Gly Ser Gln Lys Ala Val Glu Arg Glu<br>            180                185               190 | 576 |
| cag gag cgc gtc aag tcg gcg ggg gcc tgg atc atc cac ccg tac agc<br>Gln Glu Arg Val Lys Ser Ala Gly Ala Trp Ile Ile His Pro Tyr Ser<br>               195                200               205 | 624 |
| gac ttc agg ttc tac tgg gac ttc acc atg ctg ctg ttc atg gtg gga<br>Asp Phe Arg Phe Tyr Trp Asp Phe Thr Met Leu Leu Phe Met Val Gly | 672 |

```
                  210                 215                 220
aac ctc atc atc atc cca gtg ggc atc acc ttc ttc aag gat gag acc       720
Asn Leu Ile Ile Ile Pro Val Gly Ile Thr Phe Phe Lys Asp Glu Thr
225                 230                 235                 240 act gcc ccg tgg atc gtg ttc aac gtg gtc tcg gac acc ttc ttc ctc       768
Thr Ala Pro Trp Ile Val Phe Asn Val Val Ser Asp Thr Phe Phe Leu
                    245                 250                 255 atg gac ctg gtg ttg aac ttc cgc acc ggc att gtg atc gag gac aac       816
Met Asp Leu Val Leu Asn Phe Arg Thr Gly Ile Val Ile Glu Asp Asn
                260                 265                 270 acg gag atc atc ctg gac ccc gag aag atc aag aag aag tat ctg cgc       864
Thr Glu Ile Ile Leu Asp Pro Glu Lys Ile Lys Lys Lys Tyr Leu Arg
            275                 280                 285 acg tgg ttc gtg gtg gac ttc gtg tcc tcc atc ccc gtg gac tac atc       912
Thr Trp Phe Val Val Asp Phe Val Ser Ser Ile Pro Val Asp Tyr Ile
        290                 295                 300 ttc ctt atc gtg gag aag ggc att gac tcc gag gtc tac aag acg gca       960
Phe Leu Ile Val Glu Lys Gly Ile Asp Ser Glu Val Tyr Lys Thr Ala
305                 310                 315                 320 cgc gcc ctg cgc atc gtg cgc ttc acc aag atc ctc agc ctc ctg cgg      1008
Arg Ala Leu Arg Ile Val Arg Phe Thr Lys Ile Leu Ser Leu Leu Arg
                    325                 330                 335 ctg ctg cgc ctc tca cgc ctg atc cgc tac atc cat cag tgg gag gag      1056
Leu Leu Arg Leu Ser Arg Leu Ile Arg Tyr Ile His Gln Trp Glu Glu
                340                 345                 350 atc ttc cac atg acc tat gac ctg gcc agc gcg gtg atg agg atc tgc      1104
Ile Phe His Met Thr Tyr Asp Leu Ala Ser Ala Val Met Arg Ile Cys
            355                 360                 365 aat ctc atc agc atg atg ctg ctg ctc tgc cac tgg gac ggc tgc ctg      1152
Asn Leu Ile Ser Met Met Leu Leu Leu Cys His Trp Asp Gly Cys Leu
        370                 375                 380 cag ttc ctg gtg cct atg ctg cag gac ttc ccg cgc aac tgc tgg gtg      1200
Gln Phe Leu Val Pro Met Leu Gln Asp Phe Pro Arg Asn Cys Trp Val
385                 390                 395                 400 tcc atc aat ggc atg gtg aac cac tcg tgg agt gaa ctg tac tcc ttc      1248
Ser Ile Asn Gly Met Val Asn His Ser Trp Ser Glu Leu Tyr Ser Phe
                    405                 410                 415 gca ctc ttc aag gcc atg agc cac atg ctg tgc atc ggg tac ggc cgg      1296
Ala Leu Phe Lys Ala Met Ser His Met Leu Cys Ile Gly Tyr Gly Arg
                420                 425                 430 cag gcg ccc gag agc atg acg gac atc tgg ctg acc atg ctc agc atg      1344
Gln Ala Pro Glu Ser Met Thr Asp Ile Trp Leu Thr Met Leu Ser Met
            435                 440                 445 att gtg ggt gcc acc tgc tac gcc atg ttc atc ggc cac gcc act gcc      1392
Ile Val Gly Ala Thr Cys Tyr Ala Met Phe Ile Gly His Ala Thr Ala
        450                 455                 460 ctc atc cag tcg ctg gac tcc tcg cgg cgc cag tac cag gag aag tac      1440
Leu Ile Gln Ser Leu Asp Ser Ser Arg Arg Gln Tyr Gln Glu Lys Tyr
465                 470                 475                 480 aag cag gtg gag cag tac atg tcc ttc cac aag ctg cca gct gac ttc      1488
Lys Gln Val Glu Gln Tyr Met Ser Phe His Lys Leu Pro Ala Asp Phe
                    485                 490                 495 cgc cag aag atc cac gac tac tat gag cac cgt tac cag ggc aag atg      1536
Arg Gln Lys Ile His Asp Tyr Tyr Glu His Arg Tyr Gln Gly Lys Met
                500                 505                 510 ttt gac gag gac agc atc ctg ggc gag ctc aac ggg ccc ctg cgg gag      1584
Phe Asp Glu Asp Ser Ile Leu Gly Glu Leu Asn Gly Pro Leu Arg Glu
            515                 520                 525 gag atc gtc aac ttc aac tgc cgg aag ctg gtg gcc tcc atg ccg ctg      1632
Glu Ile Val Asn Phe Asn Cys Arg Lys Leu Val Ala Ser Met Pro Leu
```

-continued

| | | | | | | | | | | | | | | | |
|---|---|---|---|---|---|---|---|---|---|---|---|---|---|---|---|
| | | 530 | | | | 535 | | | | | 540 | | | | |
| ttc | gcc | aac | gcc | gac | ccc | aac | ttc | gtc | acg | gcc | atg | ctg | acc | aag | ctc | 1680 |
| Phe | Ala | Asn | Ala | Asp | Pro | Asn | Phe | Val | Thr | Ala | Met | Leu | Thr | Lys | Leu |
| 545 | | | | 550 | | | | | 555 | | | | | 560 | |
| aag | ttc | gag | gtc | ttc | cag | ccg | ggt | gac | tac | atc | atc | cgc | gaa | ggc | acc | 1728 |
| Lys | Phe | Glu | Val | Phe | Gln | Pro | Gly | Asp | Tyr | Ile | Ile | Arg | Glu | Gly | Thr |
| | | | 565 | | | | | 570 | | | | | 575 | | |
| atc | ggg | aag | aag | atg | tac | ttc | atc | cag | cac | ggc | gtg | gtc | agc | gtg | ctc | 1776 |
| Ile | Gly | Lys | Lys | Met | Tyr | Phe | Ile | Gln | His | Gly | Val | Val | Ser | Val | Leu |
| | | | 580 | | | | | 585 | | | | | 590 | | |
| act | aag | ggc | aac | aag | gag | atg | aag | ctg | tcc | gat | ggc | tcc | tac | ttc | ggg | 1824 |
| Thr | Lys | Gly | Asn | Lys | Glu | Met | Lys | Leu | Ser | Asp | Gly | Ser | Tyr | Phe | Gly |
| | 595 | | | | | 600 | | | | | 605 | | | | |
| gag | atc | tgc | ctg | ctc | acc | cgg | ggc | cgc | cgc | acg | gcg | agc | gtg | cgg | gct | 1872 |
| Glu | Ile | Cys | Leu | Leu | Thr | Arg | Gly | Arg | Arg | Thr | Ala | Ser | Val | Arg | Ala |
| | 610 | | | | | 615 | | | | | 620 | | | | |
| gac | acc | tac | tgc | cgc | ctc | tat | tcg | ctg | agc | gtg | gac | aac | ttc | aac | gag | 1920 |
| Asp | Thr | Tyr | Cys | Arg | Leu | Tyr | Ser | Leu | Ser | Val | Asp | Asn | Phe | Asn | Glu |
| 625 | | | | 630 | | | | | 635 | | | | | 640 | |
| gtg | ctg | gag | gag | tac | ccc | atg | atg | cgg | cgc | gcc | ttc | gag | acg | gtg | gcc | 1968 |
| Val | Leu | Glu | Glu | Tyr | Pro | Met | Met | Arg | Arg | Ala | Phe | Glu | Thr | Val | Ala |
| | | | | 645 | | | | | 650 | | | | | 655 | |
| atc | gac | cgc | ctg | gac | cgc | atc | ggc | aag | aag | aat | tcc | atc | ctc | ctg | cac | 2016 |
| Ile | Asp | Arg | Leu | Asp | Arg | Ile | Gly | Lys | Lys | Asn | Ser | Ile | Leu | Leu | His |
| | | 660 | | | | | 665 | | | | | 670 | | | |
| aag | gtg | cag | cat | gac | ctc | aac | tcg | ggc | gta | ttc | aac | aac | cag | gag | aac | 2064 |
| Lys | Val | Gln | His | Asp | Leu | Asn | Ser | Gly | Val | Phe | Asn | Asn | Gln | Glu | Asn |
| | | 675 | | | | | 680 | | | | | 685 | | | |
| gcc | atc | atc | cag | gag | atc | gtc | aag | tac | gac | cgc | gag | atg | gtg | cag | cag | 2112 |
| Ala | Ile | Ile | Gln | Glu | Ile | Val | Lys | Tyr | Asp | Arg | Glu | Met | Val | Gln | Gln |
| | 690 | | | | | 695 | | | | | 700 | | | | |
| gcc | gag | ctg | ggt | cag | cgc | gtg | ggc | ctc | ttc | ccg | ccg | ccg | ccg | ccg | ccg | 2160 |
| Ala | Glu | Leu | Gly | Gln | Arg | Val | Gly | Leu | Phe | Pro | Pro | Pro | Pro | Pro | Pro |
| 705 | | | | 710 | | | | | 715 | | | | | 720 | |
| ccg | cag | gtc | acc | tcg | gcc | atc | gcc | acg | ctg | cag | cag | gcg | gcg | gcc | atg | 2208 |
| Pro | Gln | Val | Thr | Ser | Ala | Ile | Ala | Thr | Leu | Gln | Gln | Ala | Ala | Ala | Met |
| | | | | 725 | | | | | 730 | | | | | 735 | |
| agc | ttc | tgc | ccg | cag | gtg | gcg | cgg | ccg | ctc | gtg | ggg | ccg | ctg | gcg | ctc | 2256 |
| Ser | Phe | Cys | Pro | Gln | Val | Ala | Arg | Pro | Leu | Val | Gly | Pro | Leu | Ala | Leu |
| | | | 740 | | | | | 745 | | | | | 750 | | |
| ggc | tcg | ccg | cgc | ctc | gtg | cgc | cgc | ccc | ccg | ggg | ccc | gca | cct | gcc | | 2304 |
| Gly | Ser | Pro | Arg | Leu | Val | Arg | Arg | Pro | Pro | Gly | Pro | Ala | Pro | Ala | |
| | | 755 | | | | | 760 | | | | | 765 | | | |
| gcc | gcc | tca | ccc | ggg | ccc | ccg | ccc | ccc | gcc | agc | ccc | ccg | ggc | gcg | ccc | 2352 |
| Ala | Ala | Ser | Pro | Gly | Pro | Pro | Pro | Pro | Ala | Ser | Pro | Pro | Gly | Ala | Pro |
| | 770 | | | | | 775 | | | | | 780 | | | | |
| gcc | agc | ccc | cgg | gca | ccg | cgg | acc | tcg | ccc | tac | ggc | ggc | ctg | ccc | gcc | 2400 |
| Ala | Ser | Pro | Arg | Ala | Pro | Arg | Thr | Ser | Pro | Tyr | Gly | Gly | Leu | Pro | Ala |
| 785 | | | | 790 | | | | | 795 | | | | | 800 | |
| gcc | ccc | ctt | gct | ggg | ccc | gcc | ctg | ccc | gcg | cgc | cgc | ctg | agc | cgc | gcg | 2448 |
| Ala | Pro | Leu | Ala | Gly | Pro | Ala | Leu | Pro | Ala | Arg | Arg | Leu | Ser | Arg | Ala |
| | | | | 805 | | | | | 810 | | | | | 815 | |
| tcg | cgc | cca | ctg | tcc | gcc | tcg | cag | ccc | tcg | ctg | cct | cac | ggc | gcc | ccc | 2496 |
| Ser | Arg | Pro | Leu | Ser | Ala | Ser | Gln | Pro | Ser | Leu | Pro | His | Gly | Ala | Pro |
| | | | 820 | | | | | 825 | | | | | 830 | | |
| ggc | ccc | gcg | gcc | tcc | aca | cgc | ccg | gcc | agc | agc | tcc | aca | ccg | cgc | ttg | 2544 |
| Gly | Pro | Ala | Ala | Ser | Thr | Arg | Pro | Ala | Ser | Ser | Ser | Thr | Pro | Arg | Leu |
| | | 835 | | | | | 840 | | | | | 845 | | | |
| ggg | ccc | acg | ccc | gct | gcc | cgg | gcc | gcc | gcg | ccc | agc | ccg | gac | cgc | agg | 2592 |
| Gly | Pro | Thr | Pro | Ala | Ala | Arg | Ala | Ala | Ala | Pro | Ser | Pro | Asp | Arg | Arg |

```
                            850                   855                   860
        gac tcg gcc tca ccc ggc gcc gcc ggc ggc ctg gac ccc cag gac tcc    2640
        Asp Ser Ala Ser Pro Gly Ala Ala Gly Gly Leu Asp Pro Gln Asp Ser
        865                 870                 875                 880 gcg cgc tcg cgc ctc tcg tcc aac ttg tga                            2670
        Ala Arg Ser Arg Leu Ser Ser Asn Leu
                        885
```

<210> SEQ ID NO 4
<211> LENGTH: 889
<212> TYPE: PRT
<213> ORGANISM: human

<400> SEQUENCE: 4

```
Met Asp Ala Arg Gly Gly Gly Arg Pro Gly Glu Ser Pro Gly Ala
1               5                   10                  15

Thr Pro Ala Pro Gly Pro Pro Pro Pro Pro Ala Pro Pro Gln
            20                  25                  30

Gln Gln Pro Pro Pro Pro Pro Ala Pro Pro Gly Pro Gly
                35                  40                  45

Pro Ala Pro Pro Gln His Pro Arg Ala Glu Ala Leu Pro Pro Glu
50                  55                  60

Ala Ala Asp Glu Gly Gly Pro Arg Gly Arg Leu Arg Ser Arg Asp Ser
65                  70                  75                  80

Ser Cys Gly Arg Pro Gly Thr Pro Gly Ala Ala Ser Thr Ala Lys Gly
                85                  90                  95

Ser Pro Asn Gly Glu Cys Gly Arg Gly Glu Pro Gln Cys Ser Pro Ala
                100                 105                 110

Gly Pro Glu Gly Pro Ala Arg Gly Pro Lys Val Ser Phe Ser Cys Arg
                115                 120                 125

Gly Ala Ala Ser Gly Pro Ala Pro Gly Pro Gly Pro Ala Glu Glu Ala
                130                 135                 140

Gly Ser Glu Glu Ala Gly Pro Ala Gly Glu Pro Arg Gly Ser Gln Ala
145                 150                 155                 160

Ser Phe Met Gln Arg Gln Phe Gly Ala Leu Leu Gln Pro Gly Val Asn
                165                 170                 175

Lys Phe Ser Leu Arg Met Phe Gly Ser Gln Lys Ala Val Glu Arg Glu
                180                 185                 190

Gln Glu Arg Val Lys Ser Ala Gly Ala Trp Ile Ile His Pro Tyr Ser
                195                 200                 205

Asp Phe Arg Phe Tyr Trp Asp Phe Thr Met Leu Leu Phe Met Val Gly
                210                 215                 220

Asn Leu Ile Ile Ile Pro Val Gly Ile Thr Phe Phe Lys Asp Glu Thr
225                 230                 235                 240

Thr Ala Pro Trp Ile Val Phe Asn Val Val Ser Asp Thr Phe Phe Leu
                245                 250                 255

Met Asp Leu Val Leu Asn Phe Arg Thr Gly Ile Val Ile Glu Asp Asn
                260                 265                 270

Thr Glu Ile Ile Leu Asp Pro Glu Lys Ile Lys Lys Lys Tyr Leu Arg
                275                 280                 285

Thr Trp Phe Val Val Asp Phe Val Ser Ser Ile Pro Val Asp Tyr Ile
                290                 295                 300

Phe Leu Ile Val Glu Lys Gly Ile Asp Ser Glu Val Tyr Lys Thr Ala
305                 310                 315                 320

Arg Ala Leu Arg Ile Val Arg Phe Thr Lys Ile Leu Ser Leu Leu Arg
                325                 330                 335
```

```
Leu Leu Arg Leu Ser Arg Leu Ile Arg Tyr Ile His Gln Trp Glu Glu
                340                 345                 350

Ile Phe His Met Thr Tyr Asp Leu Ala Ser Ala Val Met Arg Ile Cys
                355                 360                 365

Asn Leu Ile Ser Met Met Leu Leu Cys His Trp Asp Gly Cys Leu
            370                 375                 380

Gln Phe Leu Val Pro Met Leu Gln Asp Phe Pro Arg Asn Cys Trp Val
385                 390                 395                 400

Ser Ile Asn Gly Met Val Asn His Ser Trp Ser Glu Leu Tyr Ser Phe
                405                 410                 415

Ala Leu Phe Lys Ala Met Ser His Met Leu Cys Ile Gly Tyr Gly Arg
                420                 425                 430

Gln Ala Pro Glu Ser Met Thr Asp Ile Trp Leu Thr Met Leu Ser Met
                435                 440                 445

Ile Val Gly Ala Thr Cys Tyr Ala Met Phe Ile Gly His Ala Thr Ala
                450                 455                 460

Leu Ile Gln Ser Leu Asp Ser Ser Arg Arg Gln Tyr Gln Glu Lys Tyr
465                 470                 475                 480

Lys Gln Val Glu Gln Tyr Met Ser Phe His Lys Leu Pro Ala Asp Phe
                485                 490                 495

Arg Gln Lys Ile His Asp Tyr Tyr Glu His Arg Tyr Gln Gly Lys Met
                500                 505                 510

Phe Asp Glu Asp Ser Ile Leu Gly Glu Leu Asn Gly Pro Leu Arg Glu
                515                 520                 525

Glu Ile Val Asn Phe Asn Cys Arg Lys Leu Val Ala Ser Met Pro Leu
                530                 535                 540

Phe Ala Asn Ala Asp Pro Asn Phe Val Thr Ala Met Leu Thr Lys Leu
545                 550                 555                 560

Lys Phe Glu Val Phe Gln Pro Gly Asp Tyr Ile Ile Arg Glu Gly Thr
                565                 570                 575

Ile Gly Lys Lys Met Tyr Phe Ile Gln His Gly Val Val Ser Val Leu
                580                 585                 590

Thr Lys Gly Asn Lys Glu Met Lys Leu Ser Asp Gly Ser Tyr Phe Gly
                595                 600                 605

Glu Ile Cys Leu Leu Thr Arg Gly Arg Arg Thr Ala Ser Val Arg Ala
                610                 615                 620

Asp Thr Tyr Cys Arg Leu Tyr Ser Leu Ser Val Asp Asn Phe Asn Glu
625                 630                 635                 640

Val Leu Glu Glu Tyr Pro Met Met Arg Arg Ala Phe Glu Thr Val Ala
                645                 650                 655

Ile Asp Arg Leu Asp Arg Ile Gly Lys Lys Asn Ser Ile Leu Leu His
                660                 665                 670

Lys Val Gln His Asp Leu Asn Ser Gly Val Phe Asn Asn Gln Glu Asn
                675                 680                 685

Ala Ile Ile Gln Glu Ile Val Lys Tyr Asp Arg Glu Met Val Gln Gln
                690                 695                 700

Ala Glu Leu Gly Gln Arg Val Gly Leu Phe Pro Pro Pro Pro Pro Pro
705                 710                 715                 720

Pro Gln Val Thr Ser Ala Ile Ala Thr Leu Gln Gln Ala Ala Ala Met
                725                 730                 735

Ser Phe Cys Pro Gln Val Ala Arg Pro Leu Val Gly Pro Leu Ala Leu
                740                 745                 750

Gly Ser Pro Arg Leu Val Arg Arg Pro Pro Pro Gly Pro Ala Pro Ala
```

-continued

```
                   755                 760                 765
Ala Ala Ser Pro Gly Pro Pro Pro Ala Ser Pro Pro Gly Ala Pro
    770                 775                 780

Ala Ser Pro Arg Ala Pro Arg Thr Ser Pro Tyr Gly Gly Leu Pro Ala
785                 790                 795                 800

Ala Pro Leu Ala Gly Pro Ala Leu Pro Ala Arg Arg Leu Ser Arg Ala
                805                 810                 815

Ser Arg Pro Leu Ser Ala Ser Gln Pro Ser Leu Pro His Gly Ala Pro
                820                 825                 830

Gly Pro Ala Ala Ser Thr Arg Pro Ala Ser Ser Ser Thr Pro Arg Leu
                835                 840                 845

Gly Pro Thr Pro Ala Ala Arg Ala Ala Pro Ser Pro Asp Arg Arg
                850                 855                 860

Asp Ser Ala Ser Pro Gly Ala Ala Gly Gly Leu Asp Pro Gln Asp Ser
865                 870                 875                 880

Ala Arg Ser Arg Leu Ser Ser Asn Leu
                885

<210> SEQ ID NO 5
<211> LENGTH: 2325
<212> TYPE: DNA
<213> ORGANISM: human
<220> FEATURE:
<221> NAME/KEY: CDS
<222> LOCATION: (1)..(2325)

<400> SEQUENCE: 5 atg gag gca gag cag cgg ccg gcg gcg ggg gcc agc gaa ggg gcg acc       48
Met Glu Ala Glu Gln Arg Pro Ala Ala Gly Ala Ser Glu Gly Ala Thr
 1               5                  10                  15 cct gga ctg gag gcg gtg cct ccc gtt gct ccc ccg cct gcg acc gcg       96
Pro Gly Leu Glu Ala Val Pro Pro Val Ala Pro Pro Pro Ala Thr Ala
                20                  25                  30 gcc tca ggt ccg atc ccc aaa tct ggg cct gag cct aag agg agg cac      144
Ala Ser Gly Pro Ile Pro Lys Ser Gly Pro Glu Pro Lys Arg Arg His
            35                  40                  45 ctt ggg acg ctg ctc cag cct acg gtc aac aag ttc tcc ctt cgg gtg      192
Leu Gly Thr Leu Leu Gln Pro Thr Val Asn Lys Phe Ser Leu Arg Val
        50                  55                  60 ttc ggc agc cac aaa gca gtg gaa atc gag cag gag cgg gtg aag tca      240
Phe Gly Ser His Lys Ala Val Glu Ile Glu Gln Glu Arg Val Lys Ser
65                  70                  75                  80 gcg ggg gcc tgg atc atc cac ccc tac agc gac ttc cgg ttt tac tgg      288
Ala Gly Ala Trp Ile Ile His Pro Tyr Ser Asp Phe Arg Phe Tyr Trp
                85                  90                  95 gac ctg atc atg ctg ctg ctg atg gtg ggg aac ctc atc gtc ctg cct      336
Asp Leu Ile Met Leu Leu Leu Met Val Gly Asn Leu Ile Val Leu Pro
            100                 105                 110 gtg ggc atc acc ttc ttc aag gag gag aac tcc ccg cct tgg atc gtc      384
Val Gly Ile Thr Phe Phe Lys Glu Glu Asn Ser Pro Pro Trp Ile Val
        115                 120                 125 ttc aac gta ttg tct gat act ttc ttc cta ctg gat ctg gtg ctc aac      432
Phe Asn Val Leu Ser Asp Thr Phe Phe Leu Leu Asp Leu Val Leu Asn
    130                 135                 140 ttc cga acg ggc atc gtg gtg gag gag ggt gct gag atc ctg ctg gca      480
Phe Arg Thr Gly Ile Val Val Glu Glu Gly Ala Glu Ile Leu Leu Ala
145                 150                 155                 160 ccg cgg gcc atc cgc acg cgc tac ctg cgc acc tgg ttc ctg gtt gac      528
Pro Arg Ala Ile Arg Thr Arg Tyr Leu Arg Thr Trp Phe Leu Val Asp
                165                 170                 175
```

```
ctc atc tct tct atc cct gtg gat tac atc ttc cta gtg gtg gag ctg        576
Leu Ile Ser Ser Ile Pro Val Asp Tyr Ile Phe Leu Val Val Glu Leu
        180                 185                 190 gag cca cgg ttg gac gct gag gtc tac aaa acg gca cgg gcc cta cgc        624
Glu Pro Arg Leu Asp Ala Glu Val Tyr Lys Thr Ala Arg Ala Leu Arg
    195                 200                 205 atc gtt cgc ttc acc aag atc cta agc ctg ctg agg ctg ctc cgc ctc        672
Ile Val Arg Phe Thr Lys Ile Leu Ser Leu Leu Arg Leu Leu Arg Leu
210                 215                 220 tcc cgc ctc atc cgc tac ata cac cag tgg gag gag atc ttt cac atg        720
Ser Arg Leu Ile Arg Tyr Ile His Gln Trp Glu Glu Ile Phe His Met
225                 230                 235                 240 acc tat gac ctg gcc agt gct gtg gtt cgc atc ttc aac ctc att ggg        768
Thr Tyr Asp Leu Ala Ser Ala Val Val Arg Ile Phe Asn Leu Ile Gly
            245                 250                 255 atg atg ctg ctg cta tgt cac tgg gat ggc tgt ctg cag ttc ctg gtg        816
Met Met Leu Leu Leu Cys His Trp Asp Gly Cys Leu Gln Phe Leu Val
        260                 265                 270 ccc atg ctg cag gac ttc cct ccc gac tgc tgg gtc tcc atc aac cac        864
Pro Met Leu Gln Asp Phe Pro Pro Asp Cys Trp Val Ser Ile Asn His
    275                 280                 285 atg gtg aac cac tcg tgg ggc cgc cag tat tcc cat gcc ctg ttc aag        912
Met Val Asn His Ser Trp Gly Arg Gln Tyr Ser His Ala Leu Phe Lys
290                 295                 300 gcc atg agc cac atg ctg tgc att ggc tat ggg cag cag gca cct gta        960
Ala Met Ser His Met Leu Cys Ile Gly Tyr Gly Gln Gln Ala Pro Val
305                 310                 315                 320 ggc atg ccc gac gtc tgg ctc acc atg ctc agc atg atc gta ggt gcc       1008
Gly Met Pro Asp Val Trp Leu Thr Met Leu Ser Met Ile Val Gly Ala
            325                 330                 335 aca tgc tac gcc atg ttc atc ggc cat gcc acg gca ctc atc cag tcc       1056
Thr Cys Tyr Ala Met Phe Ile Gly His Ala Thr Ala Leu Ile Gln Ser
        340                 345                 350 ctg gac tct tcc cgg cgt cag tac cag gag aag tac aag cag gtg gag       1104
Leu Asp Ser Ser Arg Arg Gln Tyr Gln Glu Lys Tyr Lys Gln Val Glu
    355                 360                 365 cag tac atg tcc ttc cac aag ctg cca gca gac acg cgg cag cgc atc       1152
Gln Tyr Met Ser Phe His Lys Leu Pro Ala Asp Thr Arg Gln Arg Ile
370                 375                 380 cac gag tac tat gag cac cgc tac cag ggc aag atg ttc gat gag gaa       1200
His Glu Tyr Tyr Glu His Arg Tyr Gln Gly Lys Met Phe Asp Glu Glu
385                 390                 395                 400 agc atc ctg ggc gag ctg agc gag ccg ctt cgc gag gag atc att aac       1248
Ser Ile Leu Gly Glu Leu Ser Glu Pro Leu Arg Glu Glu Ile Ile Asn
            405                 410                 415 ttc acc tgt cgg ggc ctg gtg gcc cac atg ccg ctg ttt gcc cat gcc       1296
Phe Thr Cys Arg Gly Leu Val Ala His Met Pro Leu Phe Ala His Ala
        420                 425                 430 gac ccc agc ttc gtc act gca gtt ctc acc aag ctg cgc ttt gag gtc       1344
Asp Pro Ser Phe Val Thr Ala Val Leu Thr Lys Leu Arg Phe Glu Val
    435                 440                 445 ttc cag ccg ggg gat ctc gtg gtg cgt gag ggc tcc gtg ggg agg aag       1392
Phe Gln Pro Gly Asp Leu Val Val Arg Glu Gly Ser Val Gly Arg Lys
450                 455                 460 atg tac ttc atc cag cat ggg ctg ctc agt gtg ctg gcc cgc ggc gcc       1440
Met Tyr Phe Ile Gln His Gly Leu Leu Ser Val Leu Ala Arg Gly Ala
465                 470                 475                 480 cgg gac aca cgc ctc acc gat gga tcc tac ttt ggg gag atc tgc ctg       1488
Arg Asp Thr Arg Leu Thr Asp Gly Ser Tyr Phe Gly Glu Ile Cys Leu
            485                 490                 495
```

| | | | | | | | | | | | | | | | | |
|---|---|---|---|---|---|---|---|---|---|---|---|---|---|---|---|---|
| cta | act | agg | ggc | cgg | cgc | aca | gcc | agt | gtt | cgg | gct | gac | acc | tac | tgc | 1536 |
| Leu | Thr | Arg | Gly | Arg | Arg | Thr | Ala | Ser | Val | Arg | Ala | Asp | Thr | Tyr | Cys | |
| | | 500 | | | | | 505 | | | | | 510 | | | | |
| cgc | ctt | tac | tca | ctc | agc | gtg | gac | cat | ttc | aat | gct | gtg | ctt | gag | gag | 1584 |
| Arg | Leu | Tyr | Ser | Leu | Ser | Val | Asp | His | Phe | Asn | Ala | Val | Leu | Glu | Glu | |
| | | 515 | | | | | 520 | | | | | 525 | | | | |
| ttc | ccc | atg | atg | cgc | cgg | gcc | ttt | gag | act | gtg | gcc | atg | gat | cgg | ctg | 1632 |
| Phe | Pro | Met | Met | Arg | Arg | Ala | Phe | Glu | Thr | Val | Ala | Met | Asp | Arg | Leu | |
| | 530 | | | | | 535 | | | | | 540 | | | | | |
| ctc | cgc | atc | ggc | aag | aag | aat | tcc | ata | ctg | cag | cgg | aag | cgc | tcc | gag | 1680 |
| Leu | Arg | Ile | Gly | Lys | Lys | Asn | Ser | Ile | Leu | Gln | Arg | Lys | Arg | Ser | Glu | |
| 545 | | | | 550 | | | | | 555 | | | | | 560 | | |
| cca | agt | cca | ggc | agc | agt | ggt | ggc | atc | atg | gag | cag | cac | ttg | gtg | caa | 1728 |
| Pro | Ser | Pro | Gly | Ser | Ser | Gly | Gly | Ile | Met | Glu | Gln | His | Leu | Val | Gln | |
| | | | 565 | | | | | 570 | | | | | 575 | | | |
| cat | gac | aga | gac | atg | gct | cgg | ggt | gtt | cgg | ggt | cgg | gcc | ccg | agc | aca | 1776 |
| His | Asp | Arg | Asp | Met | Ala | Arg | Gly | Val | Arg | Gly | Arg | Ala | Pro | Ser | Thr | |
| | | 580 | | | | | 585 | | | | | 590 | | | | |
| gga | gct | cag | ctt | agt | gga | aag | cca | gta | ctg | tgg | gag | cca | ctg | gta | cat | 1824 |
| Gly | Ala | Gln | Leu | Ser | Gly | Lys | Pro | Val | Leu | Trp | Glu | Pro | Leu | Val | His | |
| | | 595 | | | | | 600 | | | | | 605 | | | | |
| gcg | ccc | ctt | cag | gca | gct | gct | gtg | acc | tcc | aat | gtg | gcc | att | gcc | ctg | 1872 |
| Ala | Pro | Leu | Gln | Ala | Ala | Ala | Val | Thr | Ser | Asn | Val | Ala | Ile | Ala | Leu | |
| | 610 | | | | | 615 | | | | | 620 | | | | | |
| act | cat | cag | cgg | ggc | cct | ctg | ccc | ctc | tcc | cct | gac | tct | cca | gcc | acc | 1920 |
| Thr | His | Gln | Arg | Gly | Pro | Leu | Pro | Leu | Ser | Pro | Asp | Ser | Pro | Ala | Thr | |
| 625 | | | | 630 | | | | | 635 | | | | | 640 | | |
| ctc | ctt | gct | cgc | tct | gct | tgg | cgc | tca | gca | ggc | tct | cca | gct | tcc | ccg | 1968 |
| Leu | Leu | Ala | Arg | Ser | Ala | Trp | Arg | Ser | Ala | Gly | Ser | Pro | Ala | Ser | Pro | |
| | | | | 645 | | | | | 650 | | | | | 655 | | |
| ctg | gtg | ccc | gtc | cga | gct | ggc | cca | tgg | gca | tcc | acc | tcc | cgc | ctg | ccc | 2016 |
| Leu | Val | Pro | Val | Arg | Ala | Gly | Pro | Trp | Ala | Ser | Thr | Ser | Arg | Leu | Pro | |
| | | | 660 | | | | | 665 | | | | | 670 | | | |
| gcc | cca | cct | gcc | cga | acc | ctg | cac | gcc | agc | cta | tcc | cgg | gca | ggg | cgc | 2064 |
| Ala | Pro | Pro | Ala | Arg | Thr | Leu | His | Ala | Ser | Leu | Ser | Arg | Ala | Gly | Arg | |
| | | 675 | | | | | 680 | | | | | 685 | | | | |
| tcc | cag | gtc | tcc | ctg | ctg | ggt | ccc | cct | cca | gga | gga | ggt | gga | cgg | cgg | 2112 |
| Ser | Gln | Val | Ser | Leu | Leu | Gly | Pro | Pro | Pro | Gly | Gly | Gly | Gly | Arg | Arg | |
| | 690 | | | | | 695 | | | | | 700 | | | | | |
| cta | gga | cct | cgg | ggc | cgc | cca | ctc | tca | gcc | tcc | caa | ccc | tct | ctg | cct | 2160 |
| Leu | Gly | Pro | Arg | Gly | Arg | Pro | Leu | Ser | Ala | Ser | Gln | Pro | Ser | Leu | Pro | |
| 705 | | | | 710 | | | | | 715 | | | | | 720 | | |
| cag | cgg | gca | aca | ggc | gat | ggc | tct | cct | ggg | cgt | aag | gga | tca | gga | agt | 2208 |
| Gln | Arg | Ala | Thr | Gly | Asp | Gly | Ser | Pro | Gly | Arg | Lys | Gly | Ser | Gly | Ser | |
| | | | | 725 | | | | | 730 | | | | | 735 | | |
| gag | cgg | ctg | cct | ccc | tca | ggg | ctc | ctg | gcc | aaa | cct | cca | agg | aca | gcc | 2256 |
| Glu | Arg | Leu | Pro | Pro | Ser | Gly | Leu | Leu | Ala | Lys | Pro | Pro | Arg | Thr | Ala | |
| | | | 740 | | | | | 745 | | | | | 750 | | | |
| cag | ccc | ccc | agg | cca | cca | gtg | cct | gag | cca | gcc | aca | ccc | cgg | ggt | ctc | 2304 |
| Gln | Pro | Pro | Arg | Pro | Pro | Val | Pro | Glu | Pro | Ala | Thr | Pro | Arg | Gly | Leu | |
| | | 755 | | | | | 760 | | | | | 765 | | | | |
| cag | ctt | tct | gcc | aac | atg | taa | | | | | | | | | | 2325 |
| Gln | Leu | Ser | Ala | Asn | Met | | | | | | | | | | | |
| | 770 | | | | | | | | | | | | | | | |

```
<210> SEQ ID NO 6
<211> LENGTH: 774
<212> TYPE: PRT
<213> ORGANISM: human

<400> SEQUENCE: 6
```

```
Met Glu Ala Glu Gln Arg Pro Ala Ala Gly Ala Ser Glu Gly Ala Thr
1               5                   10                  15

Pro Gly Leu Glu Ala Val Pro Val Ala Pro Pro Ala Thr Ala
            20              25              30

Ala Ser Gly Pro Ile Pro Lys Ser Gly Pro Glu Pro Lys Arg Arg His
        35                  40                  45

Leu Gly Thr Leu Leu Gln Pro Thr Val Asn Lys Phe Ser Leu Arg Val
    50                  55                  60

Phe Gly Ser His Lys Ala Val Glu Ile Glu Gln Glu Arg Val Lys Ser
65              70                  75                  80

Ala Gly Ala Trp Ile Ile His Pro Tyr Ser Asp Phe Arg Phe Tyr Trp
                85                  90                  95

Asp Leu Ile Met Leu Leu Leu Met Val Gly Asn Leu Ile Val Leu Pro
                100                 105                 110

Val Gly Ile Thr Phe Phe Lys Glu Glu Asn Ser Pro Pro Trp Ile Val
            115                 120                 125

Phe Asn Val Leu Ser Asp Thr Phe Phe Leu Leu Asp Leu Val Leu Asn
    130                 135                 140

Phe Arg Thr Gly Ile Val Glu Glu Gly Ala Glu Ile Leu Leu Ala
145             150                 155                 160

Pro Arg Ala Ile Arg Thr Arg Tyr Leu Arg Thr Trp Phe Leu Val Asp
                165                 170                 175

Leu Ile Ser Ser Ile Pro Val Asp Tyr Ile Phe Leu Val Val Glu Leu
            180                 185                 190

Glu Pro Arg Leu Asp Ala Glu Val Tyr Lys Thr Ala Arg Ala Leu Arg
        195                 200                 205

Ile Val Arg Phe Thr Lys Ile Leu Ser Leu Leu Arg Leu Leu Arg Leu
    210                 215                 220

Ser Arg Leu Ile Arg Tyr Ile His Gln Trp Glu Glu Ile Phe His Met
225             230                 235                 240

Thr Tyr Asp Leu Ala Ser Ala Val Val Arg Ile Phe Asn Leu Ile Gly
            245                 250                 255

Met Met Leu Leu Leu Cys His Trp Asp Gly Cys Leu Gln Phe Leu Val
        260                 265                 270

Pro Met Leu Gln Asp Phe Pro Pro Asp Cys Trp Val Ser Ile Asn His
    275                 280                 285

Met Val Asn His Ser Trp Gly Arg Gln Tyr Ser His Ala Leu Phe Lys
    290                 295                 300

Ala Met Ser His Met Leu Cys Ile Gly Tyr Gly Gln Gln Ala Pro Val
305             310                 315                 320

Gly Met Pro Asp Val Trp Leu Thr Met Leu Ser Met Ile Val Gly Ala
            325                 330                 335

Thr Cys Tyr Ala Met Phe Ile Gly His Ala Thr Ala Leu Ile Gln Ser
            340                 345                 350

Leu Asp Ser Ser Arg Arg Gln Tyr Gln Glu Lys Tyr Lys Gln Val Glu
        355                 360                 365

Gln Tyr Met Ser Phe His Lys Leu Pro Ala Asp Thr Arg Gln Arg Ile
    370                 375                 380

His Glu Tyr Tyr Glu His Arg Tyr Gln Gly Lys Met Phe Asp Glu Glu
385             390                 395                 400

Ser Ile Leu Gly Glu Leu Ser Glu Pro Leu Arg Glu Glu Ile Ile Asn
            405                 410                 415

Phe Thr Cys Arg Gly Leu Val Ala His Met Pro Leu Phe Ala His Ala
```

```
                420             425             430
Asp Pro Ser Phe Val Thr Ala Val Leu Thr Lys Leu Arg Phe Glu Val
        435                 440                 445

Phe Gln Pro Gly Asp Leu Val Val Arg Glu Gly Ser Val Gly Arg Lys
    450                 455                 460

Met Tyr Phe Ile Gln His Gly Leu Leu Ser Val Leu Ala Arg Gly Ala
465                 470                 475                 480

Arg Asp Thr Arg Leu Thr Asp Gly Ser Tyr Phe Gly Glu Ile Cys Leu
                485                 490                 495

Leu Thr Arg Gly Arg Arg Thr Ala Ser Val Arg Ala Asp Thr Tyr Cys
            500                 505                 510

Arg Leu Tyr Ser Leu Ser Val Asp His Phe Asn Ala Val Leu Glu Glu
        515                 520                 525

Phe Pro Met Met Arg Arg Ala Phe Glu Thr Val Ala Met Asp Arg Leu
    530                 535                 540

Leu Arg Ile Gly Lys Lys Asn Ser Ile Leu Gln Arg Lys Arg Ser Glu
545                 550                 555                 560

Pro Ser Pro Gly Ser Ser Gly Gly Ile Met Glu Gln His Leu Val Gln
                565                 570                 575

His Asp Arg Asp Met Ala Arg Gly Val Arg Gly Arg Ala Pro Ser Thr
            580                 585                 590

Gly Ala Gln Leu Ser Gly Lys Pro Val Leu Trp Glu Pro Leu Val His
        595                 600                 605

Ala Pro Leu Gln Ala Ala Val Thr Ser Asn Val Ala Ile Ala Leu
    610                 615                 620

Thr His Gln Arg Gly Pro Leu Pro Leu Ser Pro Asp Ser Pro Ala Thr
625                 630                 635                 640

Leu Leu Ala Arg Ser Ala Trp Arg Ser Ala Gly Ser Pro Ala Ser Pro
                645                 650                 655

Leu Val Pro Val Arg Ala Gly Pro Trp Ala Ser Thr Ser Arg Leu Pro
            660                 665                 670

Ala Pro Pro Ala Arg Thr Leu His Ala Ser Leu Ser Arg Ala Gly Arg
        675                 680                 685

Ser Gln Val Ser Leu Leu Gly Pro Pro Gly Gly Gly Arg Arg
    690                 695                 700

Leu Gly Pro Arg Gly Arg Pro Leu Ser Ala Ser Gln Pro Ser Leu Pro
705                 710                 715                 720

Gln Arg Ala Thr Gly Asp Gly Ser Pro Gly Arg Lys Gly Ser Gly Ser
                725                 730                 735

Glu Arg Leu Pro Pro Ser Gly Leu Leu Ala Lys Pro Pro Arg Thr Ala
            740                 745                 750

Gln Pro Pro Arg Pro Val Pro Glu Pro Ala Thr Pro Arg Gly Leu
        755                 760                 765

Gln Leu Ser Ala Asn Met
        770

<210> SEQ ID NO 7
<211> LENGTH: 3612
<212> TYPE: DNA
<213> ORGANISM: human
<220> FEATURE:
<221> NAME/KEY: CDS
<222> LOCATION: (1)..(3612)

<400> SEQUENCE: 7 atg gac aag ctg ccg ccg tcc atg cgc aag cgg ctc tac agc ctc ccg        48
```

```
Met Asp Lys Leu Pro Pro Ser Met Arg Lys Arg Leu Tyr Ser Leu Pro
1               5                   10                  15 cag cag gtg ggg gcc aag gcg tgg atc atg gac gag gaa gag gac gcc        96
Gln Gln Val Gly Ala Lys Ala Trp Ile Met Asp Glu Glu Glu Asp Ala
            20                  25                  30 gag gag gag ggg gcc ggg ggc cgc caa gac ccc agc cgc agg agc atc       144
Glu Glu Glu Gly Ala Gly Gly Arg Gln Asp Pro Ser Arg Arg Ser Ile
        35                  40                  45 cgg ctg cgg cca ctg ccc tcg ccc tcc ccc tcg gcg gcc gcg ggt ggc       192
Arg Leu Arg Pro Leu Pro Ser Pro Ser Pro Ser Ala Ala Ala Gly Gly
    50                  55                  60 acg gag tcc cgg agc tcg gcc ctc ggg gca gcg gac agc gaa ggg ccg       240
Thr Glu Ser Arg Ser Ser Ala Leu Gly Ala Ala Asp Ser Glu Gly Pro
65                  70                  75                  80 gcc cgc ggc gcg ggc aag tcc agc acg aac ggc gac tgc agg cgc ttc       288
Ala Arg Gly Ala Gly Lys Ser Ser Thr Asn Gly Asp Cys Arg Arg Phe
                85                  90                  95 cgc ggg agc ctg gcc tcg ctg ggc agc cgg ggc ggc ggc agc ggc ggc       336
Arg Gly Ser Leu Ala Ser Leu Gly Ser Arg Gly Gly Gly Ser Gly Gly
            100                 105                 110 acg ggg agc ggc agc agt cac gga cac ctg cat gac tcc gcg gag gag       384
Thr Gly Ser Gly Ser Ser His Gly His Leu His Asp Ser Ala Glu Glu
        115                 120                 125 cgg cgg ctc atc gcc gag ggc gac gcg tcc ccc ggc gag gac agg acg       432
Arg Arg Leu Ile Ala Glu Gly Asp Ala Ser Pro Gly Glu Asp Arg Thr
    130                 135                 140 ccc cca ggc ctg gcg gcc gag ccc gag cgc ccc ggc gcc tcg gcg cag       480
Pro Pro Gly Leu Ala Ala Glu Pro Glu Arg Pro Gly Ala Ser Ala Gln
145                 150                 155                 160 ccc gca gcc tcg ccg ccg ccc cag cag cca ccg cag ccg gcc tcc           528
Pro Ala Ala Ser Pro Pro Pro Gln Gln Pro Pro Gln Pro Ala Ser
                165                 170                 175 gcc tcc tgc gag cag ccc tcg gtg gac acc gct atc aaa gtg gag gga       576
Ala Ser Cys Glu Gln Pro Ser Val Asp Thr Ala Ile Lys Val Glu Gly
            180                 185                 190 ggc gcg gct gcc ggc gac cag atc ctc ccg gag gcc gag gtg cgc ctg       624
Gly Ala Ala Ala Gly Asp Gln Ile Leu Pro Glu Ala Glu Val Arg Leu
        195                 200                 205 ggc cag gcc ggc ttc atg cag cgc cag ttc ggg gcc atg ctc caa ccc       672
Gly Gln Ala Gly Phe Met Gln Arg Gln Phe Gly Ala Met Leu Gln Pro
    210                 215                 220 ggg gtc aac aaa ttc tcc cta agg atg ttc ggc agc cag aaa gcc gtg       720
Gly Val Asn Lys Phe Ser Leu Arg Met Phe Gly Ser Gln Lys Ala Val
225                 230                 235                 240 gag cgc gaa cag gag agg gtc aag tcg gcc gga ttt tgg att atc cac       768
Glu Arg Glu Gln Glu Arg Val Lys Ser Ala Gly Phe Trp Ile Ile His
                245                 250                 255 ccc tac agt gac ttc aga ttt tac tgg gac ctg acc atg ctg ctg ctg       816
Pro Tyr Ser Asp Phe Arg Phe Tyr Trp Asp Leu Thr Met Leu Leu Leu
            260                 265                 270 atg gtg gga aac ctg att atc att cct gtg ggc atc acc ttc ttc aag       864
Met Val Gly Asn Leu Ile Ile Ile Pro Val Gly Ile Thr Phe Phe Lys
        275                 280                 285 gat gag aac acc aca ccc tgg att gtc ttc aat gtg gtg tca gac aca       912
Asp Glu Asn Thr Thr Pro Trp Ile Val Phe Asn Val Val Ser Asp Thr
    290                 295                 300 ttc ttc ctc atc gac ttg gtc ctc aac ttc cgc aca ggg atc gtg gtg       960
Phe Phe Leu Ile Asp Leu Val Leu Asn Phe Arg Thr Gly Ile Val Val
305                 310                 315                 320 gag gac aac aca gag atc atc ctg gac ccg cag cgg att aaa atg aag      1008
```

```
                    -continued

Glu Asp Asn Thr Glu Ile Ile Leu Asp Pro Gln Arg Ile Lys Met Lys
                325                 330                 335 tac ctg aaa agc tgg ttc atg gta gat ttc att tcc tcc atc ccc gtg         1056
Tyr Leu Lys Ser Trp Phe Met Val Asp Phe Ile Ser Ser Ile Pro Val
            340                 345                 350 gac tac atc ttc ctc att gtg gag aca cgc atc gac tcg gag gtc tac         1104
Asp Tyr Ile Phe Leu Ile Val Glu Thr Arg Ile Asp Ser Glu Val Tyr
        355                 360                 365 aag act gcc cgg gcc ctg cgc att gtc cgc ttc acg aag atc ctc agc         1152
Lys Thr Ala Arg Ala Leu Arg Ile Val Arg Phe Thr Lys Ile Leu Ser
    370                 375                 380 ctc tta cgc ctg tta cgc ctc tcc cgc ctc att cga tat att cac cag         1200
Leu Leu Arg Leu Leu Arg Leu Ser Arg Leu Ile Arg Tyr Ile His Gln
385                 390                 395                 400 tgg gaa gag atc ttc cac atg acc tac gac ctg gcc agc gcc gtg gtg         1248
Trp Glu Glu Ile Phe His Met Thr Tyr Asp Leu Ala Ser Ala Val Val
                405                 410                 415 cgc atc gtg aac ctc atc ggc atg atg ctc ctc tgc cac tgg gac             1296
Arg Ile Val Asn Leu Ile Gly Met Met Leu Leu Leu Cys His Trp Asp
            420                 425                 430 ggc tgc ctg cag ttc ctg gta ccc atg cta cag gac ttc cct gac gac         1344
Gly Cys Leu Gln Phe Leu Val Pro Met Leu Gln Asp Phe Pro Asp Asp
        435                 440                 445 tgc tgg gtg tcc atc aac aac atg gtg aac aac tcc tgg ggg aag cag         1392
Cys Trp Val Ser Ile Asn Asn Met Val Asn Asn Ser Trp Gly Lys Gln
    450                 455                 460 tac tcc tac gcg ctc ttc aag gcc atg agc cac atg ctg tgc atc ggc         1440
Tyr Ser Tyr Ala Leu Phe Lys Ala Met Ser His Met Leu Cys Ile Gly
465                 470                 475                 480 tac ggg cgg cag gcg ccc gtg ggc atg tcc gac gtc tgg ctc acc atg         1488
Tyr Gly Arg Gln Ala Pro Val Gly Met Ser Asp Val Trp Leu Thr Met
                485                 490                 495 ctc agc atg atc gtg ggt gcc acc tgc tac gcc atg ttc att ggc cac         1536
Leu Ser Met Ile Val Gly Ala Thr Cys Tyr Ala Met Phe Ile Gly His
            500                 505                 510 gcc act gcc ctc atc cag tcc ctg gac tcc tcc cgg cgc cag tac cag         1584
Ala Thr Ala Leu Ile Gln Ser Leu Asp Ser Ser Arg Arg Gln Tyr Gln
        515                 520                 525 gaa aag tac aag cag gtg gag cag tac atg tcc ttt cac aag ctc ccg         1632
Glu Lys Tyr Lys Gln Val Glu Gln Tyr Met Ser Phe His Lys Leu Pro
    530                 535                 540 ccc gac acc cgg cag cgc atc cac gac tac tac gag cac cgc tac cag         1680
Pro Asp Thr Arg Gln Arg Ile His Asp Tyr Tyr Glu His Arg Tyr Gln
545                 550                 555                 560 ggc aag atg ttc gac gag gag agc atc ctg ggc gag cta agc gag ccc         1728
Gly Lys Met Phe Asp Glu Glu Ser Ile Leu Gly Glu Leu Ser Glu Pro
                565                 570                 575 ctg cgg gag gag atc atc aac ttt aac tgt cgg aag ctg gtg gcc tcc         1776
Leu Arg Glu Glu Ile Ile Asn Phe Asn Cys Arg Lys Leu Val Ala Ser
            580                 585                 590 atg cca ctg ttt gcc aat gcg gac ccc aac ttc gtg acg tcc atg ctg         1824
Met Pro Leu Phe Ala Asn Ala Asp Pro Asn Phe Val Thr Ser Met Leu
        595                 600                 605 acc aag ctg cgt ttc gag gtc ttc cag cct ggg gac tac atc atc cgg         1872
Thr Lys Leu Arg Phe Glu Val Phe Gln Pro Gly Asp Tyr Ile Ile Arg
    610                 615                 620 gaa ggc acc att ggc aag aag atg tac ttc atc cag cat ggc gtg gtc         1920
Glu Gly Thr Ile Gly Lys Lys Met Tyr Phe Ile Gln His Gly Val Val
625                 630                 635                 640 agc gtg ctc acc aag ggc aac aag gag acc aag ctg gcc gac ggc tcc         1968
```

```
Ser Val Leu Thr Lys Gly Asn Lys Glu Thr Lys Leu Ala Asp Gly Ser
                645                 650                 655 tac ttt gga gag atc tgc ctg ctg acc cgg ggc cgg cgc aca gcc agc       2016
Tyr Phe Gly Glu Ile Cys Leu Leu Thr Arg Gly Arg Arg Thr Ala Ser
            660                 665                 670 gtg agg gcc gac acc tac tgc cgc ctc tac tcg ctg agc gtg gac aac       2064
Val Arg Ala Asp Thr Tyr Cys Arg Leu Tyr Ser Leu Ser Val Asp Asn
        675                 680                 685 ttc aat gag gtg ctg gag gag tac ccc atg atg cga agg gcc ttc gag       2112
Phe Asn Glu Val Leu Glu Glu Tyr Pro Met Met Arg Arg Ala Phe Glu
    690                 695                 700 acc gtg gcg ctg gac cgc ctg gac cgc att ggc aag aag aac tcc atc       2160
Thr Val Ala Leu Asp Arg Leu Asp Arg Ile Gly Lys Lys Asn Ser Ile
705                 710                 715                 720 ctc ctc cac aaa gtc cag cac gac ctc aac tcc ggc gtc ttc aac tac       2208
Leu Leu His Lys Val Gln His Asp Leu Asn Ser Gly Val Phe Asn Tyr
                725                 730                 735 cag gag aat gag atc atc cag cag att gtg cag cat gac cgg gag atg       2256
Gln Glu Asn Glu Ile Ile Gln Gln Ile Val Gln His Asp Arg Glu Met
            740                 745                 750 gcc cac tgc gcg cac cgc gtc cag gct gct gcc tct gcc acc cca acc       2304
Ala His Cys Ala His Arg Val Gln Ala Ala Ala Ser Ala Thr Pro Thr
        755                 760                 765 ccc acg ccc gtc atc tgg acc ccg ctg atc cag gca cca ctg cag gct       2352
Pro Thr Pro Val Ile Trp Thr Pro Leu Ile Gln Ala Pro Leu Gln Ala
    770                 775                 780 gcc gct gcc acc act tct gtg gcc ata gcc ctc acc cac cac cct cgc       2400
Ala Ala Ala Thr Thr Ser Val Ala Ile Ala Leu Thr His His Pro Arg
785                 790                 795                 800 ctg cct gct gcc atc ttc cgc cct ccc cca gga tct ggg ctg ggc aac       2448
Leu Pro Ala Ala Ile Phe Arg Pro Pro Pro Gly Ser Gly Leu Gly Asn
                805                 810                 815 ctc ggt gcc ggg cag acg cca agg cac ctg aaa cgg ctg cag tcc ctg       2496
Leu Gly Ala Gly Gln Thr Pro Arg His Leu Lys Arg Leu Gln Ser Leu
            820                 825                 830 atc cct tct gcg ctg ggc tcc gcc tcg ccc gcc agc agc ccg tcc cag       2544
Ile Pro Ser Ala Leu Gly Ser Ala Ser Pro Ala Ser Ser Pro Ser Gln
        835                 840                 845 gtg gac aca ccg tct tca tcc tcc ttc cac atc caa cag ctg gct gga       2592
Val Asp Thr Pro Ser Ser Ser Ser Phe His Ile Gln Gln Leu Ala Gly
    850                 855                 860 ttc tct gcc ccc gct gga ctg agc cca ctc ctg ccc tca tcc agc tcc       2640
Phe Ser Ala Pro Ala Gly Leu Ser Pro Leu Leu Pro Ser Ser Ser Ser
865                 870                 875                 880 tcc cca ccc ccc ggg gcc tgt ggc tcc ccc tcg gct ccc aca cca tca       2688
Ser Pro Pro Pro Gly Ala Cys Gly Ser Pro Ser Ala Pro Thr Pro Ser
                885                 890                 895 gct ggc gta gcc gcc acc acc ata gcc ggg ttt ggc cac ttc cac aag       2736
Ala Gly Val Ala Ala Thr Thr Ile Ala Gly Phe Gly His Phe His Lys
            900                 905                 910 gcg ctg ggt ggc tcc ctg tcc tcc tcc gac tct ccc ctg ctc acc ccg       2784
Ala Leu Gly Gly Ser Leu Ser Ser Ser Asp Ser Pro Leu Leu Thr Pro
        915                 920                 925 ctg cag cca ggc gcc cgc tcc ccg cag gct gcc cag cca tct ccc gcg       2832
Leu Gln Pro Gly Ala Arg Ser Pro Gln Ala Ala Gln Pro Ser Pro Ala
    930                 935                 940 cca ccc ggg gcc cgg gga ggc ctg gga ctc ccg gag cac ttc ctg cca       2880
Pro Pro Gly Ala Arg Gly Gly Leu Gly Leu Pro Glu His Phe Leu Pro
945                 950                 955                 960 ccc cca ccc tca tcc aga tcc ccg tca tct agc ccc ggg cag ctg ggc       2928
```

-continued

```
              Pro Pro Pro Ser Ser Arg Ser Pro Ser Ser Ser Pro Gly Gln Leu Gly
                           965                 970                 975 cag cct ccc ggg gag ttg tcc cta ggt ctg gcc act ggc cca ctg agc          2976
Gln Pro Pro Gly Glu Leu Ser Leu Gly Leu Ala Thr Gly Pro Leu Ser
            980                 985                 990 acg cca gag aca ccc cca cgg cag cct gag ccg ccg tcc ctt gtg gca          3024
Thr Pro Glu Thr Pro Pro Arg Gln Pro Glu Pro Pro Ser Leu Val Ala
            995                 1000                1005 ggg gcc tct ggg ggg gct tcc cct gta ggc ttt act ccc cga gga              3069
Gly Ala Ser Gly Gly Ala Ser Pro Val Gly Phe Thr Pro Arg Gly
        1010                1015                1020 ggt ctc agc ccc cct ggc cac agc cca ggc ccc aga acc ttc                  3114
Gly Leu Ser Pro Pro Gly His Ser Pro Gly Pro Arg Thr Phe
        1025                1030                1035 ccg agt gcc ccg ccc cgg gcc tct ggc tcc cac gga tcc ttg ctc              3159
Pro Ser Ala Pro Pro Arg Ala Ser Gly Ser His Gly Ser Leu Leu
        1040                1045                1050 ctg cca cct gca tcc agc ccc cca ccc cag gtc ccc cag cgc                  3204
Leu Pro Pro Ala Ser Ser Pro Pro Pro Gln Val Pro Gln Arg
        1055                1060                1065 cgg ggc aca ccc ccg ctc acc ccc ggc cgc ctc acc cag gac ctc              3249
Arg Gly Thr Pro Pro Leu Thr Pro Gly Arg Leu Thr Gln Asp Leu
        1070                1075                1080 aag ctc atc tcc gcg tct cag cca gcc ctg cct cag gac ggg gcg              3294
Lys Leu Ile Ser Ala Ser Gln Pro Ala Leu Pro Gln Asp Gly Ala
        1085                1090                1095 cag act ctc cgc aga gcc tcc ccg cac tcc tca ggg gag tcc atg              3339
Gln Thr Leu Arg Arg Ala Ser Pro His Ser Ser Gly Glu Ser Met
        1100                1105                1110 gct gcc ttc ccg ctc ttc ccc agg gct ggg ggt ggc agc ggg ggc              3384
Ala Ala Phe Pro Leu Phe Pro Arg Ala Gly Gly Gly Ser Gly Gly
        1115                1120                1125 agt ggg agc agc ggg ggc ctc ggt ccc cct ggg agg ccc tat ggt              3429
Ser Gly Ser Ser Gly Gly Leu Gly Pro Pro Gly Arg Pro Tyr Gly
        1130                1135                1140 gcc atc ccc ggc cag cac gtc act ctg cct cgg aag aca tcc tca              3474
Ala Ile Pro Gly Gln His Val Thr Leu Pro Arg Lys Thr Ser Ser
        1145                1150                1155 ggt tct ttg cca ccc cct ctg tct ttg ttt ggg gca aga gcc acc              3519
Gly Ser Leu Pro Pro Pro Leu Ser Leu Phe Gly Ala Arg Ala Thr
        1160                1165                1170 tct tct ggg ggg ccc cct ctg act gct gga ccc cag agg gaa cct              3564
Ser Ser Gly Gly Pro Pro Leu Thr Ala Gly Pro Gln Arg Glu Pro
        1175                1180                1185 ggg gcc agg cct gag cca gtg cgc tcc aaa ctg cca tcc aat cta              3609
Gly Ala Arg Pro Glu Pro Val Arg Ser Lys Leu Pro Ser Asn Leu
        1190                1195                1200 tga                                                                      3612
```

<210> SEQ ID NO 8
<211> LENGTH: 1203
<212> TYPE: PRT
<213> ORGANISM: human

<400> SEQUENCE: 8

Met Asp Lys Leu Pro Pro Ser Met Arg Lys Arg Leu Tyr Ser Leu Pro
1               5                   10                  15

Gln Gln Val Gly Ala Lys Ala Trp Ile Met Asp Glu Glu Glu Asp Ala
            20                  25                  30

Glu Glu Glu Gly Ala Gly Gly Arg Gln Asp Pro Ser Arg Arg Ser Ile

```
                    35                  40                  45
Arg Leu Arg Pro Leu Pro Ser Pro Ser Pro Ser Ala Ala Gly Gly
 50                  55                  60

Thr Glu Ser Arg Ser Ser Ala Leu Gly Ala Ala Asp Ser Glu Gly Pro
 65                  70                  75                  80

Ala Arg Gly Ala Gly Lys Ser Ser Thr Asn Gly Asp Cys Arg Arg Phe
                 85                  90                  95

Arg Gly Ser Leu Ala Ser Leu Gly Ser Arg Gly Gly Ser Gly Gly
                100                 105                 110

Thr Gly Ser Gly Ser Ser His Gly His Leu His Asp Ser Ala Glu Glu
                115                 120                 125

Arg Arg Leu Ile Ala Glu Gly Asp Ala Ser Pro Gly Glu Asp Arg Thr
130                 135                 140

Pro Pro Gly Leu Ala Ala Glu Pro Glu Arg Pro Gly Ala Ser Ala Gln
145                 150                 155                 160

Pro Ala Ala Ser Pro Pro Pro Gln Gln Pro Pro Gln Pro Ala Ser
                165                 170                 175

Ala Ser Cys Glu Gln Pro Ser Val Asp Thr Ala Ile Lys Val Glu Gly
                180                 185                 190

Gly Ala Ala Ala Gly Asp Gln Ile Leu Pro Glu Ala Glu Val Arg Leu
                195                 200                 205

Gly Gln Ala Gly Phe Met Gln Arg Gln Phe Gly Ala Met Leu Gln Pro
210                 215                 220

Gly Val Asn Lys Phe Ser Leu Arg Met Phe Gly Ser Gln Lys Ala Val
225                 230                 235                 240

Glu Arg Glu Gln Glu Arg Val Lys Ser Ala Gly Phe Trp Ile Ile His
                245                 250                 255

Pro Tyr Ser Asp Phe Arg Phe Tyr Trp Asp Leu Thr Met Leu Leu Leu
                260                 265                 270

Met Val Gly Asn Leu Ile Ile Ile Pro Val Gly Ile Thr Phe Phe Lys
                275                 280                 285

Asp Glu Asn Thr Thr Pro Trp Ile Val Phe Asn Val Val Ser Asp Thr
290                 295                 300

Phe Phe Leu Ile Asp Leu Val Leu Asn Phe Arg Thr Gly Ile Val Val
305                 310                 315                 320

Glu Asp Asn Thr Glu Ile Ile Leu Asp Pro Gln Arg Ile Lys Met Lys
                325                 330                 335

Tyr Leu Lys Ser Trp Phe Met Val Asp Phe Ile Ser Ser Ile Pro Val
                340                 345                 350

Asp Tyr Ile Phe Leu Ile Val Glu Thr Arg Ile Asp Ser Glu Val Tyr
                355                 360                 365

Lys Thr Ala Arg Ala Leu Arg Ile Val Arg Phe Thr Lys Ile Leu Ser
370                 375                 380

Leu Leu Arg Leu Leu Arg Leu Ser Arg Leu Ile Arg Tyr Ile His Gln
385                 390                 395                 400

Trp Glu Glu Ile Phe His Met Thr Tyr Asp Leu Ala Ser Ala Val Val
                405                 410                 415

Arg Ile Val Asn Leu Ile Gly Met Met Leu Leu Leu Cys His Trp Asp
                420                 425                 430

Gly Cys Leu Gln Phe Leu Val Pro Met Leu Gln Asp Phe Pro Asp Asp
                435                 440                 445

Cys Trp Val Ser Ile Asn Asn Met Val Asn Asn Ser Trp Gly Lys Gln
450                 455                 460
```

```
Tyr Ser Tyr Ala Leu Phe Lys Ala Met Ser His Met Leu Cys Ile Gly
465                 470                 475                 480

Tyr Gly Arg Gln Ala Pro Val Gly Met Ser Asp Val Trp Leu Thr Met
                485                 490                 495

Leu Ser Met Ile Val Gly Ala Thr Cys Tyr Ala Met Phe Ile Gly His
            500                 505                 510

Ala Thr Ala Leu Ile Gln Ser Leu Asp Ser Ser Arg Arg Gln Tyr Gln
        515                 520                 525

Glu Lys Tyr Lys Gln Val Glu Gln Tyr Met Ser Phe His Lys Leu Pro
    530                 535                 540

Pro Asp Thr Arg Gln Arg Ile His Asp Tyr Tyr Glu His Arg Tyr Gln
545                 550                 555                 560

Gly Lys Met Phe Asp Glu Glu Ser Ile Leu Gly Glu Leu Ser Glu Pro
                565                 570                 575

Leu Arg Glu Glu Ile Ile Asn Phe Asn Cys Arg Lys Leu Val Ala Ser
            580                 585                 590

Met Pro Leu Phe Ala Asn Ala Asp Pro Asn Phe Val Thr Ser Met Leu
        595                 600                 605

Thr Lys Leu Arg Phe Glu Val Phe Gln Pro Gly Asp Tyr Ile Ile Arg
    610                 615                 620

Glu Gly Thr Ile Gly Lys Lys Met Tyr Phe Ile Gln His Gly Val Val
625                 630                 635                 640

Ser Val Leu Thr Lys Gly Asn Lys Glu Thr Lys Leu Ala Asp Gly Ser
                645                 650                 655

Tyr Phe Gly Glu Ile Cys Leu Leu Thr Arg Gly Arg Arg Thr Ala Ser
            660                 665                 670

Val Arg Ala Asp Thr Tyr Cys Arg Leu Tyr Ser Leu Ser Val Asp Asn
        675                 680                 685

Phe Asn Glu Val Leu Glu Glu Tyr Pro Met Met Arg Arg Ala Phe Glu
    690                 695                 700

Thr Val Ala Leu Asp Arg Leu Asp Arg Ile Gly Lys Lys Asn Ser Ile
705                 710                 715                 720

Leu Leu His Lys Val Gln His Asp Leu Asn Ser Gly Val Phe Asn Tyr
                725                 730                 735

Gln Glu Asn Glu Ile Ile Gln Gln Ile Val Gln His Asp Arg Glu Met
            740                 745                 750

Ala His Cys Ala His Arg Val Gln Ala Ala Ala Ser Ala Thr Pro Thr
        755                 760                 765

Pro Thr Pro Val Ile Trp Thr Pro Leu Ile Gln Ala Pro Leu Gln Ala
    770                 775                 780

Ala Ala Ala Thr Thr Ser Val Ala Ile Ala Leu Thr His His Pro Arg
785                 790                 795                 800

Leu Pro Ala Ala Ile Phe Arg Pro Pro Gly Ser Gly Leu Gly Asn
                805                 810                 815

Leu Gly Ala Gly Gln Thr Pro Arg His Leu Lys Arg Leu Gln Ser Leu
            820                 825                 830

Ile Pro Ser Ala Leu Gly Ser Ala Ser Pro Ala Ser Ser Pro Ser Gln
        835                 840                 845

Val Asp Thr Pro Ser Ser Ser Phe His Ile Gln Gln Leu Ala Gly
    850                 855                 860

Phe Ser Ala Pro Ala Gly Leu Ser Pro Leu Leu Pro Ser Ser Ser
865                 870                 875                 880

Ser Pro Pro Pro Gly Ala Cys Gly Ser Pro Ser Ala Pro Thr Pro Ser
                885                 890                 895
```

```
Ala Gly Val Ala Ala Thr Thr Ile Ala Gly Phe Gly His Phe His Lys
            900                 905                 910

Ala Leu Gly Gly Ser Leu Ser Ser Asp Ser Pro Leu Leu Thr Pro
        915                 920                 925

Leu Gln Pro Gly Ala Arg Ser Pro Gln Ala Ala Gln Pro Ser Pro Ala
    930                 935                 940

Pro Pro Gly Ala Arg Gly Gly Leu Gly Leu Pro Glu His Phe Leu Pro
945                 950                 955                 960

Pro Pro Pro Ser Ser Arg Ser Pro Ser Ser Pro Gly Gln Leu Gly
            965                 970                 975

Gln Pro Pro Gly Glu Leu Ser Leu Gly Leu Ala Thr Gly Pro Leu Ser
        980                 985                 990

Thr Pro Glu Thr Pro Pro Arg Gln  Pro Glu Pro Ser  Leu Val Ala
        995                 1000                1005

Gly Ala  Ser Gly Gly Ala Ser  Pro Val Gly Phe Thr  Pro Arg Gly
        1010                1015                1020

Gly Leu  Ser Pro Pro Gly His  Ser Pro Gly Pro Pro  Arg Thr Phe
        1025                1030                1035

Pro Ser  Ala Pro Pro Arg Ala  Ser Gly Ser His Gly  Ser Leu Leu
        1040                1045                1050

Leu Pro  Pro Ala Ser Ser Pro  Pro Pro Gln Val  Pro Gln Arg
        1055                1060                1065

Arg Gly  Thr Pro Pro Leu Thr  Pro Gly Arg Leu Thr  Gln Asp Leu
        1070                1075                1080

Lys Leu  Ile Ser Ala Ser Gln  Pro Ala Leu Pro Gln  Asp Gly Ala
        1085                1090                1095

Gln Thr  Leu Arg Arg Ala Ser  Pro His Ser Ser Gly  Glu Ser Met
        1100                1105                1110

Ala Ala  Phe Pro Leu Phe Pro  Arg Ala Gly Gly  Ser Gly Gly
        1115                1120                1125

Ser Gly  Ser Ser Gly Gly Leu  Gly Pro Pro Gly Arg  Pro Tyr Gly
        1130                1135                1140

Ala Ile  Pro Gly Gln His Val  Thr Leu Pro Arg Lys  Thr Ser Ser
        1145                1150                1155

Gly Ser  Leu Pro Pro Pro Leu  Ser Leu Phe Gly Ala  Arg Ala Thr
        1160                1165                1170

Ser Ser  Gly Gly Pro Pro Leu  Thr Ala Gly Pro Gln  Arg Glu Pro
        1175                1180                1185

Gly Ala  Arg Pro Glu Pro Val  Arg Ser Lys Leu Pro  Ser Asn Leu
        1190                1195                1200

<210> SEQ ID NO 9
<211> LENGTH: 9
<212> TYPE: PRT
<213> ORGANISM: artificial
<220> FEATURE:
<223> OTHER INFORMATION: region linking the S3 and S4 segment of HCN

<400> SEQUENCE: 9

Glu Thr Arg Ile Asp Ser Glu Val Tyr
1               5

<210> SEQ ID NO 10
<211> LENGTH: 9
<212> TYPE: PRT
<213> ORGANISM: artificial
<220> FEATURE:
```

```
<223> OTHER INFORMATION: region linking the S3 and S4 segment of HCN

<400> SEQUENCE: 10

Glu Ala Arg Ile Asp Ser Glu Val Tyr
1               5

<210> SEQ ID NO 11
<211> LENGTH: 4
<212> TYPE: PRT
<213> ORGANISM: artificial
<220> FEATURE:
<223> OTHER INFORMATION: region linking the S3 and S4 segment of HCN

<400> SEQUENCE: 11

Glu Thr Arg Ile
1

<210> SEQ ID NO 12
<211> LENGTH: 4
<212> TYPE: PRT
<213> ORGANISM: artificial
<220> FEATURE:
<223> OTHER INFORMATION: region linking the S3 and S4 segment of HCN

<400> SEQUENCE: 12

Glu Ala Arg Ile
1

<210> SEQ ID NO 13
<211> LENGTH: 9
<212> TYPE: PRT
<213> ORGANISM: artificial
<220> FEATURE:
<223> OTHER INFORMATION: region linking the S3 and S4 segment of HCN

<400> SEQUENCE: 13

Glu Ala Gly Met Asp Ser Glu Val Tyr
1               5

<210> SEQ ID NO 14
<211> LENGTH: 9
<212> TYPE: PRT
<213> ORGANISM: artificial
<220> FEATURE:
<223> OTHER INFORMATION: region linking the S3 and S4 segment of HCN

<400> SEQUENCE: 14

Glu Lys Gly Met Asp Ser Glu Val Tyr
1               5

<210> SEQ ID NO 15
<211> LENGTH: 9
<212> TYPE: PRT
<213> ORGANISM: artificial
<220> FEATURE:
<223> OTHER INFORMATION: region linking the S3 and S4 segment of HCN

<400> SEQUENCE: 15

Glu Ala Arg Met Asp Ser Glu Val Tyr
1               5

<210> SEQ ID NO 16
<211> LENGTH: 6
<212> TYPE: PRT
<213> ORGANISM: artificial
<220> FEATURE:
<223> OTHER INFORMATION: region linking the S3 and S4 segment of HCN
```

```
<400> SEQUENCE: 16

Glu Ala Arg Ile Asp Ser
1               5

<210> SEQ ID NO 17
<211> LENGTH: 9
<212> TYPE: PRT
<213> ORGANISM: artificial
<220> FEATURE:
<223> OTHER INFORMATION: region linking the S3 and S4 segment of HCN

<400> SEQUENCE: 17

Glu Thr Arg Ile Asp Ser Gly Val Tyr
1               5

<210> SEQ ID NO 18
<211> LENGTH: 9
<212> TYPE: PRT
<213> ORGANISM: artificial
<220> FEATURE:
<223> OTHER INFORMATION: region linking the S3 and S4 segment of HCN

<400> SEQUENCE: 18

Glu Thr Arg Ile Asp Ser Ala Val Tyr
1               5

<210> SEQ ID NO 19
<211> LENGTH: 9
<212> TYPE: PRT
<213> ORGANISM: artificial
<220> FEATURE:
<223> OTHER INFORMATION: region linking the S3 and S4 segment of HCN

<400> SEQUENCE: 19

Glu Thr Gly Ile Asp Ser Glu Val Tyr
1               5

<210> SEQ ID NO 20
<211> LENGTH: 9
<212> TYPE: PRT
<213> ORGANISM: artificial
<220> FEATURE:
<223> OTHER INFORMATION: region linking the S3 and S4 segment of HCN

<400> SEQUENCE: 20

Glu Ala Ala Ile Asp Ser Glu Val Tyr
1               5

<210> SEQ ID NO 21
<211> LENGTH: 9
<212> TYPE: PRT
<213> ORGANISM: artificial
<220> FEATURE:
<223> OTHER INFORMATION: region linking the S3 and S4 segment of HCN

<400> SEQUENCE: 21

Glu Thr Arg Cys Asp Ser Glu Val Tyr
1               5

<210> SEQ ID NO 22
<211> LENGTH: 9
<212> TYPE: PRT
<213> ORGANISM: artificial
<220> FEATURE:
<223> OTHER INFORMATION: region linking the S3 and S4 segment of HCN

<400> SEQUENCE: 22
```

Glu Thr Arg Ser Asp Ser Glu Val Tyr
1               5

<210> SEQ ID NO 23
<211> LENGTH: 9
<212> TYPE: PRT
<213> ORGANISM: artificial
<220> FEATURE:
<223> OTHER INFORMATION: region linking the S3 and S4 segment of HCN

<400> SEQUENCE: 23

Glu Thr Arg Thr Asp Ser Glu Val Tyr
1               5

<210> SEQ ID NO 24
<211> LENGTH: 4
<212> TYPE: PRT
<213> ORGANISM: artificial
<220> FEATURE:
<223> OTHER INFORMATION: region linking the S3 and S4 segment of HCN

<400> SEQUENCE: 24

Glu Ala Gly Met
1

<210> SEQ ID NO 25
<211> LENGTH: 36
<212> TYPE: DNA
<213> ORGANISM: artificial
<220> FEATURE:
<223> OTHER INFORMATION: synthetic oligonucleotide primer

<400> SEQUENCE: 25
atagcgcgaa ttcccgccat gcagcgccag ttcggg                            36

<210> SEQ ID NO 26
<211> LENGTH: 34
<212> TYPE: DNA
<213> ORGANISM: artificial
<220> FEATURE:
<223> OTHER INFORMATION: synthetic oligonucleotide primer

<400> SEQUENCE: 26
atagcgcgaa ttcccgccat gctccaaccc gggg                              34

<210> SEQ ID NO 27
<211> LENGTH: 37
<212> TYPE: DNA
<213> ORGANISM: artificial
<220> FEATURE:
<223> OTHER INFORMATION: synthetic oligonucleotide primer

<400> SEQUENCE: 27
atagcgcgaa ttcccgccat gttcggcagc cagaaag                           37

<210> SEQ ID NO 28
<211> LENGTH: 21
<212> TYPE: DNA
<213> ORGANISM: artificial
<220> FEATURE:
<223> OTHER INFORMATION: synthetic oligonucleotide primer

<400> SEQUENCE: 28
cggcggatcc cctagagata t                                            21

<210> SEQ ID NO 29
<211> LENGTH: 32

<210> SEQ ID NO 29
<211> LENGTH: 32
<212> TYPE: DNA
<213> ORGANISM: artificial
<220> FEATURE:
<223> OTHER INFORMATION: synthetic oligonucleotide primer

<400> SEQUENCE: 29
agcagaagct gatctcagag gaggacctgc tt                                    32

<210> SEQ ID NO 30
<211> LENGTH: 2358
<212> TYPE: DNA
<213> ORGANISM: artificial
<220> FEATURE:
<223> OTHER INFORMATION: HCN4 - MyC fusion

<400> SEQUENCE: 30

| | | | | | |
|---|---|---|---|---|---|
| agtcgacggt | accgcgggcc | cagcttggta | ccgagctcgg | atccactagt | aacggccgcc | 60 |
| agtgtgctgg | aattccgcct | cgccatggac | aagctgccgc | cgtccatgcg | caagcggctc | 120 |
| tacagcctcc | cgcagcaggt | gggggccaag | gcgtggatca | tggacgagga | agaggacgcc | 180 |
| gaggaggagg | gggccggggg | ccgccaagac | cccagccgca | ggagcatccg | gctgcggcca | 240 |
| ctgccctcgc | cctccccctc | ggcggccgcg | gtggcacgg | agtcccggag | ctcggccctc | 300 |
| ggggcagcgg | acagcgaagg | gccggcccgc | ggcgcgggca | gtccagcac | gaacggcgac | 360 |
| tgcaggcgct | ccgcgggag | cctggcctcg | ctgggcagcc | ggggcggcgg | cagcggcggc | 420 |
| acggggagcg | gcagcagtca | cggacacctg | catgactccg | cggaggagcg | gcggctcatc | 480 |
| gccgagggcg | acgcgtcccc | cggcgaggac | aggacgcccc | caggcctggc | ggccgagccc | 540 |
| gagcgccccg | gcgcctcggc | gcagcccgca | gcctcgccgc | cgccgcccca | gcagccaccg | 600 |
| cagccggcct | ccgcctcctg | cgagcagccc | tcggtggaca | ccgctatcaa | agtgggagga | 660 |
| ggcgcggctg | ccggcgacca | gatcctcccg | gaggccgagg | tgcgcctggg | ccaggccggc | 720 |
| ttcatgcagc | gccagttcgg | ggccatgctc | caacccgggg | tcaacaaatt | ctccctaagg | 780 |
| atgttcggca | gccagaaagc | cgtggagcgc | gaacaggaga | gggtcaagtc | ggccggattt | 840 |
| tggattatcc | acccctacag | tgacttcaga | ttttactggg | acctgaccat | gctgctgctg | 900 |
| atggtgggaa | acctgattat | cattcctgtg | ggcatcacct | tcttcaagga | tgagaacacc | 960 |
| acaccctgga | ttgtcttcaa | tgtggtgtca | gacacattct | tcctcatcga | cttggtcctc | 1020 |
| aacttccgca | cagggatcgt | ggtggaggac | aacacagaga | tcatcctgga | cccgcagcgg | 1080 |
| attaaaatga | agtacctgaa | aagctggttc | atggtagatt | catttcctc | catcccgtg | 1140 |
| gactacatct | tcctcattgt | ggagacacgc | atcgactcgg | aggtctacaa | gactgcccgg | 1200 |
| gccctgcgca | ttgtccgctt | cacgaagatc | ctcagcctct | tacgcctgtt | acgcctctcc | 1260 |
| cgcctcattc | gatatattca | ccagtgggaa | gagatcttcc | acatgaccta | cgacctggcc | 1320 |
| agcgccgtgg | tgcgcatcgt | gaacctcatc | ggcatgatgc | tcctgctctg | ccactgggac | 1380 |
| ggctgcctgc | agttcctggt | acccatgcta | caggacttcc | ctgacgactg | ctgggtgtcc | 1440 |
| atcaacaaca | tggtgaacaa | ctcctggggg | aagcagtact | cctacgcgct | cttcaaggcc | 1500 |
| atgagccaca | tgctgtgcat | cggctacggg | cggcaggcgc | ccgtgggcat | gtccgacgtc | 1560 |
| tggctcacca | tgctcagcat | gatcgtgggt | gccacctgct | acgccatgtt | cattggccac | 1620 |
| gccactgccc | tcatccagtc | cctggactcc | tcccggcgcc | agtaccagga | aaagtacaag | 1680 |
| caggtggagc | agtacatgtc | ctttcacaag | ctcccgcccg | acacccggca | gcgcatccac | 1740 |
| gactactacg | agcaccgcta | ccagggcaag | atgttcgacg | aggagagcat | cctgggcgag | 1800 |
| ctaagcgagc | ccctgcggga | ggagatcatc | aactttaact | gtcggaagct | ggtggcctcc | 1860 |

```
atgccactgt tgccaatgc ggaccccaac ttcgtgacgt ccatgctgac caagctgcgt   1920
ttcgaggtct tccagcctgg ggactacatc atccgggaag gcaccattgg caagaagatg   1980
tacttcatcc agcatggcgt ggtcagcgtg ctcaccaagg caacaaggag accaagctg    2040 gccgacggct cctactttgg agagatctgc ctgctgaccc ggggccggcg cacagccagc   2100
gtgagggccg acacctactg ccgcctctac tcgctgagcg tggacaactt caatgaggtg   2160
ctggaggagt accccatgat gcgaagggcc ttcgagaccg tggcgctgga ccgcctggac   2220
cgcattggca agaagaactc catcctcctc cacaaagtcc agcacgacct caactccggc   2280
gtcttcaact accaggagca gaagctgatc tcagaggagg acctgctttg agcctgatat   2340
ctctagggga tccgcccc                                                  2358
```

<210> SEQ ID NO 31
<211> LENGTH: 783
<212> TYPE: PRT
<213> ORGANISM: artificial
<220> FEATURE:
<223> OTHER INFORMATION: HCN4 - MyC fusion

<400> SEQUENCE: 31

```
Ser Arg Arg Tyr Arg Gly Pro Ser Leu Val Pro Ser Ser Asp Pro Leu
1               5                   10                  15

Val Thr Ala Ala Ser Val Leu Glu Phe Arg Leu Ala Met Asp Lys Leu
            20                  25                  30

Pro Pro Ser Met Arg Lys Arg Leu Tyr Ser Leu Pro Gln Gln Val Gly
        35                  40                  45

Ala Lys Ala Trp Ile Met Asp Glu Glu Glu Asp Ala Glu Glu Glu Gly
    50                  55                  60

Ala Gly Gly Arg Gln Asp Pro Ser Arg Arg Ser Ile Arg Leu Arg Pro
65                  70                  75                  80

Leu Pro Ser Pro Ser Pro Ser Ala Ala Ala Gly Gly Thr Glu Ser Arg
                85                  90                  95

Ser Ser Ala Leu Gly Ala Ala Asp Ser Glu Gly Pro Ala Arg Gly Ala
            100                 105                 110

Gly Lys Ser Ser Thr Asn Gly Asp Cys Arg Arg Phe Arg Gly Ser Leu
        115                 120                 125

Ala Ser Leu Gly Ser Arg Gly Gly Gly Ser Gly Gly Thr Gly Ser Gly
    130                 135                 140

Ser Ser His Gly His Leu His Asp Ser Ala Glu Glu Arg Arg Leu Ile
145                 150                 155                 160

Ala Glu Gly Asp Ala Ser Pro Gly Glu Asp Arg Thr Pro Pro Gly Leu
                165                 170                 175

Ala Ala Glu Pro Glu Arg Pro Gly Ala Ser Ala Gln Pro Ala Ala Ser
            180                 185                 190

Pro Pro Pro Pro Gln Gln Pro Pro Gln Pro Ala Ser Ala Ser Cys Glu
        195                 200                 205

Gln Pro Ser Val Asp Thr Ala Ile Lys Val Glu Gly Gly Ala Ala Ala
    210                 215                 220

Gly Asp Gln Ile Leu Pro Glu Ala Glu Val Arg Leu Gly Gln Ala Gly
225                 230                 235                 240

Phe Met Gln Arg Gln Phe Gly Ala Met Leu Gln Pro Gly Val Asn Lys
                245                 250                 255

Phe Ser Leu Arg Met Phe Gly Ser Gln Lys Ala Val Glu Arg Glu Gln
            260                 265                 270
```

```
Glu Arg Val Lys Ser Ala Gly Phe Trp Ile Ile His Pro Tyr Ser Asp
        275                 280                 285

Phe Arg Phe Tyr Trp Asp Leu Thr Met Leu Leu Met Val Gly Asn
290                 295                 300

Leu Ile Ile Ile Pro Val Gly Ile Thr Phe Phe Lys Asp Glu Asn Thr
305                 310                 315                 320

Thr Pro Trp Ile Val Phe Asn Val Val Ser Asp Thr Phe Phe Leu Ile
                325                 330                 335

Asp Leu Val Leu Asn Phe Arg Thr Gly Ile Val Val Glu Asp Asn Thr
                340                 345                 350

Glu Ile Ile Leu Asp Pro Gln Arg Ile Lys Met Lys Tyr Leu Lys Ser
                355                 360                 365

Trp Phe Met Val Asp Phe Ile Ser Ser Ile Pro Val Asp Tyr Ile Phe
370                 375                 380

Leu Ile Val Glu Thr Arg Ile Asp Ser Glu Val Tyr Lys Thr Ala Arg
385                 390                 395                 400

Ala Leu Arg Ile Val Arg Phe Thr Lys Ile Leu Ser Leu Leu Arg Leu
                405                 410                 415

Leu Arg Leu Ser Arg Leu Ile Arg Tyr Ile His Gln Trp Glu Glu Ile
                420                 425                 430

Phe His Met Thr Tyr Asp Leu Ala Ser Ala Val Val Arg Ile Val Asn
                435                 440                 445

Leu Ile Gly Met Met Leu Leu Leu Cys His Trp Asp Gly Cys Leu Gln
450                 455                 460

Phe Leu Val Pro Met Leu Gln Asp Phe Pro Asp Asp Cys Trp Val Ser
465                 470                 475                 480

Ile Asn Asn Met Val Asn Asn Ser Trp Gly Lys Gln Tyr Ser Tyr Ala
                485                 490                 495

Leu Phe Lys Ala Met Ser His Met Leu Cys Ile Gly Tyr Gly Arg Gln
                500                 505                 510

Ala Pro Val Gly Met Ser Asp Val Trp Leu Thr Met Leu Ser Met Ile
                515                 520                 525

Val Gly Ala Thr Cys Tyr Ala Met Phe Ile Gly His Ala Thr Ala Leu
530                 535                 540

Ile Gln Ser Leu Asp Ser Ser Arg Arg Gln Tyr Gln Glu Lys Tyr Lys
545                 550                 555                 560

Gln Val Glu Gln Tyr Met Ser Phe His Lys Leu Pro Pro Asp Thr Arg
                565                 570                 575

Gln Arg Ile His Asp Tyr Tyr Glu His Arg Tyr Gln Gly Lys Met Phe
                580                 585                 590

Asp Glu Glu Ser Ile Leu Gly Glu Leu Ser Glu Pro Leu Arg Glu Glu
                595                 600                 605

Ile Ile Asn Phe Asn Cys Arg Lys Leu Val Ala Ser Met Pro Leu Phe
610                 615                 620

Ala Asn Ala Asp Pro Asn Phe Val Thr Ser Met Leu Thr Lys Leu Arg
625                 630                 635                 640

Phe Glu Val Phe Gln Pro Gly Asp Tyr Ile Ile Arg Glu Gly Thr Ile
                645                 650                 655

Gly Lys Lys Met Tyr Phe Ile Gln His Gly Val Val Ser Val Leu Thr
                660                 665                 670

Lys Gly Asn Lys Glu Thr Lys Leu Ala Asp Gly Ser Tyr Phe Gly Glu
                675                 680                 685

Ile Cys Leu Leu Thr Arg Gly Arg Arg Thr Ala Ser Val Arg Ala Asp
                690                 695                 700
```

```
Thr Tyr Cys Arg Leu Tyr Ser Leu Ser Val Asp Asn Phe Asn Glu Val
705                 710                 715                 720

Leu Glu Glu Tyr Pro Met Met Arg Arg Ala Phe Glu Thr Val Ala Leu
                725                 730                 735

Asp Arg Leu Asp Arg Ile Gly Lys Lys Asn Ser Ile Leu Leu His Lys
            740                 745                 750

Val Gln His Asp Leu Asn Ser Gly Val Phe Asn Tyr Gln Glu Gln Lys
        755                 760                 765

Leu Ile Ser Glu Glu Asp Leu Leu Ala Tyr Leu Gly Ile Arg Pro
    770                 775                 780
```